(12) United States Patent
Meisel et al.

(10) Patent No.: US 9,988,427 B2
(45) Date of Patent: Jun. 5, 2018

(54) ERYTHROPOIETIN VARIANTS

(75) Inventors: Andreas Meisel, Berlin (DE); Josef Priller, Berlin (DE); Christel Bonnas, Berlin (DE); Ulrich Dirnagl, Berlin (DE)

(73) Assignee: CHARITE UNIVERSITAETSMEDIZEN-BERLIN, Berlin (DE)

( * ) Notice: Subject to any disclaimer, the term of this patent is extended or adjusted under 35 U.S.C. 154(b) by 734 days.

(21) Appl. No.: 12/334,995

(22) Filed: Dec. 15, 2008

(65) Prior Publication Data

US 2011/0008363 A1 Jan. 13, 2011

Related U.S. Application Data

(63) Continuation of application No. 11/914,368, filed as application No. PCT/EP2006/004564 on May 15, 2006, now abandoned.

(30) Foreign Application Priority Data

May 13, 2005 (EP) .................................... 05010473

(51) Int. Cl.
C07K 14/505 (2006.01)
A61K 38/18 (2006.01)
A61K 38/00 (2006.01)

(52) U.S. Cl.
CPC ............ *C07K 14/505* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,704,355 A | 11/1987 | Berstein | |
| 4,798,824 A | 1/1989 | Belzer et al. | |
| 5,888,774 A * | 3/1999 | Delcuve | 435/69.6 |
| 6,531,121 B2 * | 3/2003 | Brines et al. | 424/85.1 |
| 6,974,684 B2 * | 12/2005 | Anderson | C07K 14/705 435/69.1 |
| 7,129,390 B2 * | 10/2006 | Ivarie et al. | 800/19 |
| 7,309,687 B1 * | 12/2007 | Brines et al. | 514/7.7 |
| 2003/0130197 A1 | 7/2003 | Smith-Swintosky et al. | |
| 2003/0232347 A1 * | 12/2003 | Anderson | C07K 14/705 435/6.14 |
| 2004/0157293 A1 | 8/2004 | Evans et al. | |
| 2005/0287564 A1 * | 12/2005 | Gorman et al. | 435/6 |

FOREIGN PATENT DOCUMENTS

| | | |
|---|---|---|
| WO | 9104014 A1 | 4/1991 |
| WO | 9105867 A1 | 5/1991 |
| WO | 9409257 A1 | 4/1994 |
| WO | 9505465 A1 | 2/1995 |
| WO | 9014307 A1 | 4/1997 |
| WO | 0032772 A1 | 6/2000 |
| WO | 0035475 A2 | 6/2000 |
| WO | 0102017 A2 | 1/2001 |
| WO | 0181405 A2 | 11/2001 |
| WO | 03029291 A2 | 4/2003 |
| WO | 2004003176 A2 | 1/2004 |
| WO | 2004/043382 A | 5/2004 |
| WO | 0220031 A2 | 3/2005 |
| WO | 2005025606 A1 | 3/2005 |
| WO | WO 2005/103076 A | 11/2005 |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Kirsch et al. BMP-2 antagonists emerge from alterations in the low affinity binding epitope for receptor BMPR-II. The EMBO Journal vol. 19(13):3314-3324 (2000).*
Wen et al. Erythropoietin Structure-Function Relationships: High Degree of Sequence Homology Among Mammals. Blood, vol. 82, No. 5: pp. 1507-1516 (1993).*
Jacobs, K., et al.; "Isolation and characterization of genomic and cDNA clones of human erythropoietin"; Nature; Feb. 1985; pp. 806-810; vol. 313; Nature Publishing Group.
Lin, F-K, et al.; "Cloning and expression of the human erythropoietin gene"; Proc. Natl. Acad. Sci. USA; Nov. 1985; pp. 7580-7584; vol. 82.
Kim, C., et al.; "Codon optimization for high-level expression of human erythropoietin (EPO) in mammalian cells"; GENE; 1997; pp. 293-301; vol. 199; Elsevier Science B.V.
Cheetham et al., NMR structure of human erythropoietin and a comparison with its receptor bound conformation, Nat. Struct. Biol., 5: 861-866, 1998.
Erbayraktar et al., Asialoerythropoietin is a nonerythropoietic cytokine with broad neuroprotective activity in vivo, PNAS, 100(11):6741-6746, 2003.
Parsa et al., A novel protective effect of erythropoietin in the infarcted heart, J. Clin. Invest., 112: 999-1007, 2003.
Ruscher et al., Erythropoietin is a paracrine mediator of ischemic tolerance in the brain: evidence from an in vitro model, J. Neurosci., 22: 10291-10301,2002.
Wen et al., Erythropoietin Structure-Function Relationships: Identification of Functionally Important Domains, The Journal of Biological Chemistry, 269(36):22839-22846, 1994.

(Continued)

*Primary Examiner* — Elizabeth C. Kemmerer
*Assistant Examiner* — Regina M DeBerry
(74) *Attorney, Agent, or Firm* — Acuity Law Group, PC; Michael A. Whittaker

(57) ABSTRACT

The present invention relates to novel endogenous variants of erythropoietin (EPO) and their use for treatment or prevention of a condition associated with tissue damage due to cell death (apoptosis, necrosis) and inflammation, in particular for neuroprotection, e.g. treatment of acute (for example stroke) and chronic disease (for example ALS) of the nervous system.

2 Claims, 21 Drawing Sheets

(56) References Cited

OTHER PUBLICATIONS

Figure 4:
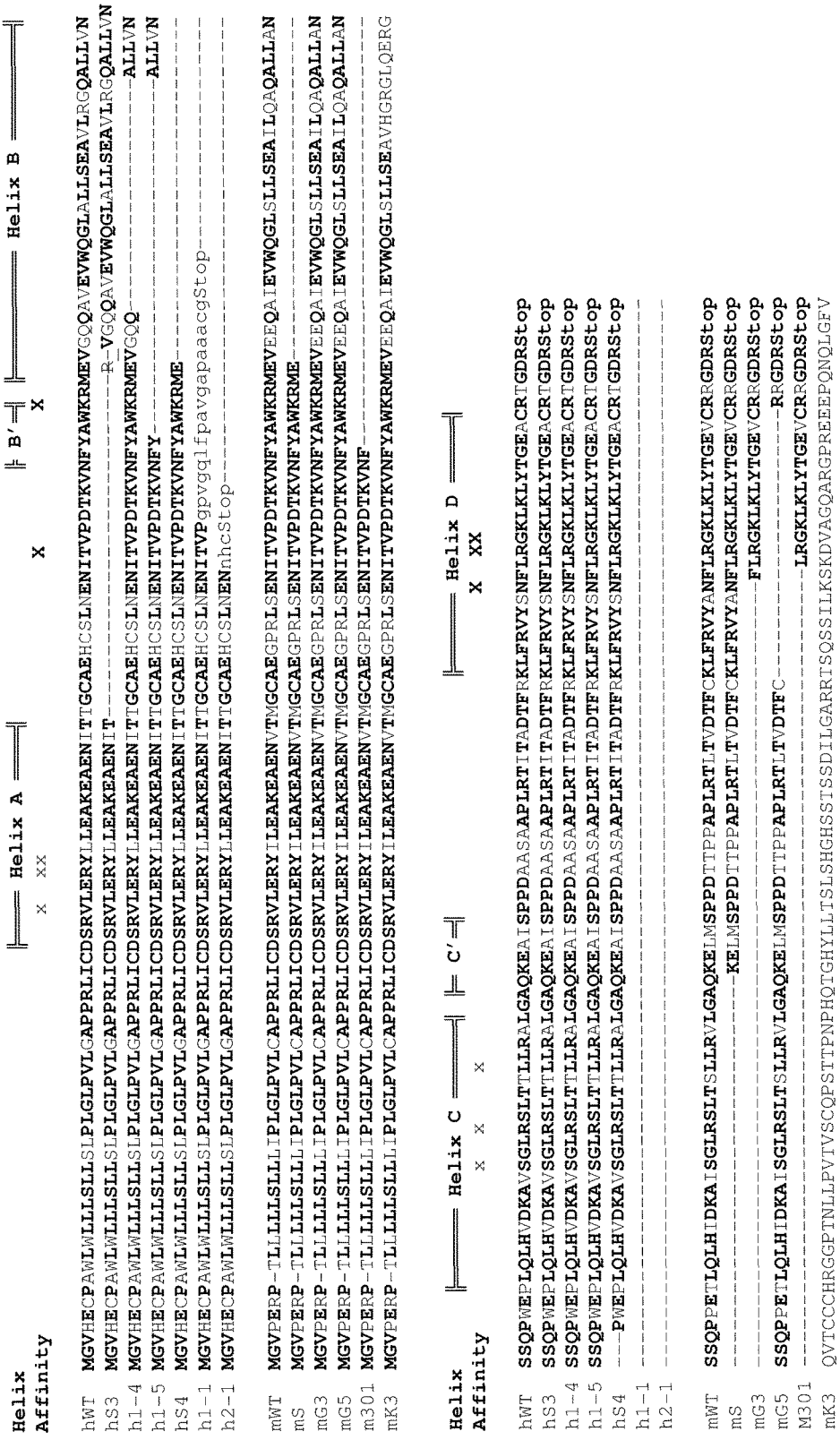

Database Geneseq [online], Database Accession No. AAY43803, Feb. 11, 2000 [retrieved Sep. 8, 2006], Retrieved from http://www.ebi.ac.uk/cgi-bin/epo/epofetch?AAY43803.
2nd Office Action dated Jul. 17, 2012 issued by the Japanese Patent Office in Japanese patent application No. 2008-510513 (in Japanese).
2nd Office Action dated Jul. 17, 2012 issued by the Japanese Patent Office in Japanese patent application No. 2008-510513 (English Translation).
Boissel et al., Erythropoietin Structure-Function Relationships Mutant Proteins that Test a Model of Tertiary Structure. J Biol Chem. Jul. 25, 1993;268(21):15983-15993.
Campana et al., Identification of a neurotrophic sequence in erythropoietin. Intnl J Molecular Med. 1998:235-241.
Chern et al., Structural role of amino acids 99-110 in recombinant human erythropoietin. Eur J Biochem. 1991;202:225-229.
Grodberg et al., Alanine scanning mutagenesis of human erythropoietin identifies four amino acids which are critical for biological activity. Eur J Biochem. 1993;218:597-601.
Wen et al., Erythropoietin Structure-Function Relationships: High Degree of Sequence Homology Among Mammals. Blood Sep. 1993;82(5):1507-1516.
Wen et al., Erythropoietin Structure-Function Relationships Identification of Functionally Important Domains. J Biol Chem. Sep. 9, 1994;269(36):22839-22846.
Office Action issued by the Korean Intellectual Property Office in Korean Patent Application No. 10-2007-7026286 dated Nov. 19, 2012.
Office Action issued by the Korean Intellectual Property Office in Korean Patent Application No. 10-2007-7026286 dated Nov. 19, 2012—English translation.
Altschul et al., Basic Local Alignment Search Tool. J Mol Biol. Oct. 5, 1990;215(3):403-410.
Bernaudin et al., A Potential Role for Erythropoietin in Focal Permanent Cerebral Ischemia in Mice. J Cereb Blood Flow Metab. Jun. 1999;19(6):643-651.
Bird et al., Single-Chain Antigen-Binding Proteins. Science Oct. 1, 1988;242(4877):423-426.
Brewer, Serum-Free B27/Neurobasal Medium Supports Differentiated Growth of Neurons From the Striatum, Substantia Nigra, Septum, Cerebral Cortex, Cerebellum, and Dentate Gyrus. J Neurosci Res. Dec. 1995;42(5):674-683.
Brines et al., Erythropoietin crosses the blood—brain barrier to protect against experimental brain injury. Proc Natl Acad Sci USA. Sep. 12, 2000;97(19):10526-10531.
Buchwald et al., Long-term, continuous intravenous heparin administration by an implantable infusion pump in ambulatory patients with recurrent venous thrombosis. Surgery Oct. 1980;88(4):507-516.
Carlezon et al., Herpes Simplex Virus-Mediated Gene Transfer As a Tool for Neuropsychiatric Research. Crit Rev Neurobiol. 2000;14(1):47-67.
Carter and Samulski, Adeno-associated viral vectors as gene delivery vehicles (Review). Int J Mol Med. Jul. 2000;6(1):17-27.
Chang and Gay, The Molecular Genetics of Lentiviral Vectors—Current and Future Perspectives. Curr Gene Ther. Sep. 2001;1(3):237-251.
Dirnagl et al., Pathobiology of ischaemic stroke: an integrated view. Trends Neurosci. Sep. 1999;22(9):391-397.

During et al., Controlled Release of Dopamine from a Polymeric Brain Implant: In Vivo Characterization. Ann Neurol. Apr. 1989;25(4):351-356.
Ehrenreich et al., Erythropoietin Therapy for Acute Stroke Is Both Safe and Beneficial. Mol Med. Aug. 2002;8 (8):495-505.
Ehrenreich et al., Erythropoietin: a candidate compound for neuroprotection in schizophrenia. Mol Psychiatry Jan. 2004;9(1):42-54.
Goodson, Dental Applications. Med Appl Controlled Release, 1984;2: 115-138.
Henn and Braus, Structural neuroimaging in schizophrenia an integrative view of neuromorphology. Eur Arch Psychiatry Clin Neurosci.1999;249 Suppl 4:48-56.
Holliger et al., "Diabodies": Small bivalent and bispecific antibody fragments. Proc Natl Acad Sci USA. Jul. 15, 1993;90(14):6444-6448.
Howard et al., Intracerebral drug delivery in rats with lesion-induced memory deficits. J Neurosurg. Jul. 1989;71(1):105-112.
Karlin and Altschul, Applications and statistics for multiple high-scoring segments in molecular sequences. Proc Natl Acad Sci USA Jun. 15, 1993;90(12):5873-5877.
Kobinger et al., Filovirus-pseudotyped lentiviral vector can efficiently and stably transduce airway epithelia in vivo. Nat Biotechnol. Mar. 2001;19(3):225-230.
Langer and Peppas, Chemical and Physical Structure of Polymers as Carriers for Controlled Release of Bioactive Agents: A Review. JMS Rev Macromol Chem Phys. 1983;C23(1):61-126.
Langer, New Methods of Drug Delivery. Science Sep. 28, 1990;249(4976):1527-1533.
Leist et al., Derivatives of Erythropoietin That Are Tissue Protective But Not Erythropoietic. Science Jul. 9, 2004;305(5681):239-242.
Levy et al., Inhibition of calcification of bioprosthetic heart valves by local controlled-release diphosphonate. Science Apr. 12, 1985;228(4696):190-192.
Lindemann et al., Versatile Retrovirus Vector Systems for Regulated Gene Expression In Vitro and In Vivo. Mol Med. Jul. 1997;3(7):466-476.
Morishita et al., Erythropoietin Receptor is Expressed in Rat Hippocampal and Cerebral Cortical Neurons, and Erythropoietin Prevents In Vitro Glutamate-Induced Neuronal Death. Neuroscience Jan. 1997;76(1):105-116.
Prass et al., Hypoxia-Induced Stroke Tolerance in the Mouse Is Mediated by Erythropoietin. Stroke Aug. 2003;34(8):1981-1986.
Saudek et al., A Preliminary Trial of the Programmable Implantable Medication System for Insulin Delivery. N Eng J Med. Aug. 31, 1989;321(9):574-579.
Sefton, Implantable Pumps. CRC Crit Ref Biomed Eng. 1987;14(3):201-240.
Springer et al., VEGF Gene Delivery to Muscle: Potential Role for Vasculogenesis in Adults. Mol Cell. Nov. 1998;2(5):549-558.
Vogeley et al., Disturbed Gyrification of the Prefrontal Region in Male Schizophrenic Patients: A Morphometric Postmortem Study. Am J Psychiatry Jan. 2000;157(1):34-39.
Zhu and D'Andrea , The molecular physiology of erythropoietin and the erythropoietin receptor. Curr Opin Hematol. Mar. 1994;1(2):113-118.
Ruscher et al., Erythropoietin Is a Paracrine Mediator of Ischemic Tolerance in the Brain: Evidence from an In Vitro Model. J Neurosci. Dec. 1, 2002;22(23):10291-10301.
Leist et al., "Derivatives of Erythropoietin That Are Tissue Protective But Not Erythropoietic", Science, 305:239-242(2004).

* cited by examiner

Fig. 1
A
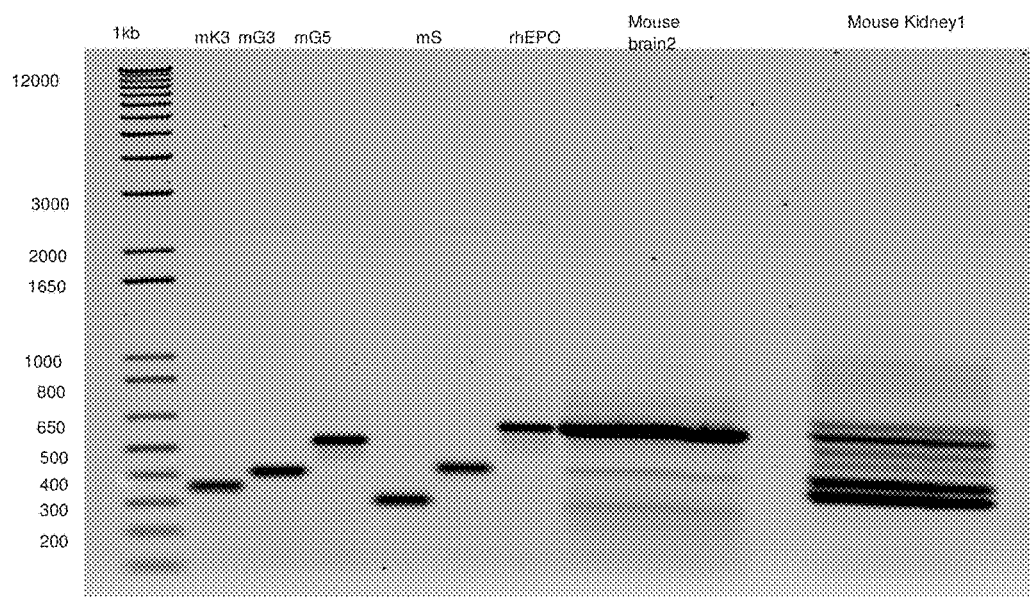
B
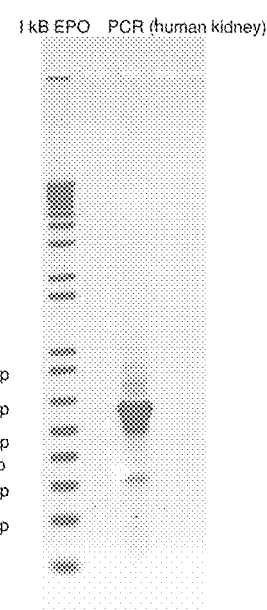

Fig. 2a

```
mEpo    atgggggtgcccgaacgtcccaccctgctgcttttactctccttgctactgattc  55
mS      atgggggtgcccgaacgtcccaccctgctgcttttactctccttgctactgattc  55
mG3     atgggggtgcccgaacgtcccaccctgctgcttttactctccttgctactgattc  55
mG5     atgggggtgcccgaacgtcccaccctgctgcttttactctccttgctactgattc  55
m301    atgggggtgcccgaacgtcccaccctgctgcttttactctccttgctactgattc  55
mK3     atgggggtgcccgaacgtcccaccctgctgcttttactctccttgctactgattc  55 mEpo    ctctgggcctcccagtcctctgtgctcccccacgcctcatctgcgacagtcgagt  110
mS      ctctgggcctcccagtcctctgtgctcccccacgcctcatctgcgacagtcgagt  110
mG3     ctctgggcctcccagtcctctgtgctcccccacgcctcatctgcgacagtcgagt  110
mG5     ctctgggcctcccagtcctctgtgctcccccacgcctcatctgcgacagtcgagt  110
m301    ctctgggcctcccagtcctctgtgctcccccacgcctcatctgcgacagtcgagt  110
mK3     ctctgggcctcccagtcctctgtgctcccccacgcctcatctgcgacagtcgagt  110 mEpo    tctggagaggtacatcttagaggccaaggaggcagaaaatgtcacgatgggttgt  165
mS      tctggagaggtacatcttagaggccaaggaggcagaaaatgtcacgatgggttgt  165
mG3     tctggagaggtacatcttagaggccaaggaggcagaaaatgtcacgatgggttgt  165
mG5     tctggagaggtacatcttagaggccaaggaggcagaaaatgtcacgatgggttgt  165
m301    tctggagaggtacatcttagaggccaaggaggcagaaaatgtcacgatgggttgt  165
mK3     tctggagaggtacatcttagaggccaaggaggcagaaaatgtcacgatgggttgt  165 mEpo    gcagaaggtcccagactgagtgaaaatattacagtcccagataccaaagtcaact  220
mS      gcagaaggtcccagactgagtgaaaatattacagtcccagataccaaagtcaact  220
mG3     gcagaaggtcccagactgagtgaaaatattacagtcccagataccaaagtcaact  220
mG5     gcagaaggtcccagactgagtgaaaatattacagtcccagataccaaagtcaact  220
m301    gcagaaggtcccagactgagtgaaaatattacagtcccagataccaaagtcaact  220
mK3     gcagaaggtcccagactgagtgaaaatattacagtcccagataccaaagtcaact  220 mEpo    tctatgcttggaaaagaatggaggtggaagaacaggccatagaagtttggcaagg  275
mS      tctatgcttggaaaagaatggag--------------------------------  243
mG3     tctatgcttggaaaagaatggaggtggaagaacaggccatagaagtttggcaagg  275
mG5     tctatgcttggaaaagaatggaggtggaagaacaggccatagaagtttggcaagg  275
m301    tc-----------------------------------------------------  222
mK3     tctatgcttggaaaagaatggaggtggaagaacaggccatagaagtttggcaagg  275 mEpo    cctgtccctgctctcagaagccatcctgcaggcccaggccctgctagccaattcc  330
mS      -------------------------------------------------------   -
mG3     cctgtccctgctctcagaagccatcctgcaggcccaggccctgctagccaa----  326
mG5     cctgtccctgctctcagaagccatcctgcaggcccaggccctgctagccaattcc  330
m301    -------------------------------------------------------   -
mK3     cctgtccctgctctcagaagc----------------------------------  296 mEpo    tcccagccaccagagacccttcagcttcatatagacaaagccatcagtggtctac  385
mS      -------------------------------------------------------   -
mG3     -------------------------------------------------------   -
mG5     tcccagccaccagagacccttcagcttcatatagacaaagccatcagtggtctac  385
m301    -------------------------------------------------------   -
mK3     :-----------------------------------------------------;   -
```

Fig. 2b

```
mEpo   gtagcctcacttcactgcttcgggtactgggagctcagaaggaattgatgtcgcc 440
mS     ----------------------------------------aaggaattgatgtcgcc 260
mG3    ---------------------------------------------------------  -
mG5    gtagcctcacttcactgcttcgggtactgggagctcagaaggaattgatgtcgcc 440
m301   ---------------------------------------------------------  -
mK3    ---------------------------------------------------------  - mEpo   tccagataccaccccacctgctccactccgaacactcacagtggatactttctgc 495
mS     tccagataccaccccacctgctccactccgaacactcacagtggatactttctgc 315
mG3    ---------------------------------------------------------  -
mG5    tccagataccaccccacctgctccactccgaacactcacagtggatactttctgc 495
m301   ---------------------------------------------------------  -
mK3    ---------------------------------------------------------  - mEpo   aagctcttccgggtctacgccaacttcctccgggggaaactgaagctgtacacgg 550
mS     aagctcttccgggtctacgccaacttcctccgggggaaactgaagctgtacacgg 370
mG3    ----------------------cttcctccgggggaaactgaagctgtacacgg 358
mG5    a-------------------------------------------------------- 496
m301   ---------------------------ctccgggggaaactgaagctgtacacgg 250
mK3    -----------------------------------------------tgtacacgg 305 mEpo   gagaggtctgcaggagaggggacaggtga 579
mS     gagaggtctgcaggagaggggacaggtga 399
mG3    gagaggtctgcaggagaggggacaggtga 387
mG5    -----------ggagaggggacaggtga 513
m301   gagaggtctgcaggagaggggacaggtga 279
mK3    gagaggtctgcaggagaggggacaggtgacatgctgctgccaccgtggtggaccg 360 mEpo   ---------------------------------------------------------
mK3    acgaacttgctccccgtcactgtgtcatgccaaccctccaccactcccaaccctc 415 mEpo   ---------------------------------------------------------
mK3    atcaaacgggtcattaccttcttaccagtctgtcccatggacactccagcaccag 470 mEpo   ---------------------------------------------------------
mK3    cagtgacatcctcggggccagaagaacttcccagagctccattctgaaatctaaa 525 mEpo   ---------------------------------------------------------
mK3    gatgtcgctggacaagcccgaggccccagagaagaagagcctcagaatcagctcg 580 mEpo   ---------------------------------------------------------
mK3    gatttgtttag 591
```

Fig. 3a

```
hWT   atgggggtgcacgaatgtcctgcctggctgtggcttctcctgtccctgctgtcgctccctctgggcctcccagtc
hS3   atgggggtgcacgaatgtcctgcctggctgtggcttctcctgtccctgctgtcgctccctctgggcctcccagtc
h1-4  atgggggtgcacgaatgtcctgcctggctgtggcttctcctgtccctgctgtcgctccctctgggcctcccagtc
h1-5  atgggggtgcacgaatgtcctgcctggctgtggcttctcctgtccctgctgtcgctccctctgggcctcccagtc
hS4   atgggggtgcacgaatgtcctgcctggctgtggcttctcctgtccctgctgtcgctccctctgggcctcccagtc
h1-1  atgggggtgcacgaatgtcctgcctggctgtggcttctcctgtccctgctgtcgctccctctgggcctcccagtc
h2-1  atgggggtgcacgaatgtcctgcctggctgtggcttctcctgtccctgctgtcgctccctctgggcctcccagtc hWT   ctgggcgccccaccacgcctcatctgtgacagccgagtcctggagaggtacctcttggaggccaaggaggccgag
hS3   ctgggcgccccaccacgcctcatctgtgacagccgagtcctggagaggtacctcttggaggccaaggaggccgag
h1-4  ctgggcgccccaccacgcctcatctgtgacagccgagtcctggagaggtacctcttggaggccaaggaggccgag
h1-5  ctgggcgccccaccacgcctcatctgtgacagccgagtcctggagaggtacctcttggaggccaaggaggccgag
hS4   ctgggcgccccaccacgcctcatctgtgacagccgagtcctggagaggtacctcttggaggccaaggaggccgag
h1-1  ctgggcgccccaccacgcctcatctgtgacagccgagtcctggagaggtacctcttggaggccaaggaggccgag
h2-1  ctgggcgccccaccacgcctcatctgtgacagccgagtcctggagaggtacctcttggaggccaaggaggccgag hWT   aatatcacgacgggctgtgctgaacactgcagcttgaatgagaatatcactgtcccagacaccaaagttaatttc
hS3   aatatcacg----------------------------------------------------------------
h1-4  aatatcacgacgggctgtgctgaacactgcagcttgaatgagaatatcactgtcccagacaccaaagttaatttc
h1-5  aatatcacgacgggctgtgctgaacactgcagcttgaatgagaatatcactgtcccagacaccaaagttaatttc
hS4   aatatcacgacgggctgtgctgaacactgcagcttgaatgagaatatcactgtcccagacaccaaagttaatttc
h1-1  aatatcacgacgggctgtgctgaacactgcagcttgaatgagaatatcactgtcccag----------------
h2-1  aatatcacgacgggctgtgctgaacactgcagcttgaatgagaa----------------------------- hWT   tatgcctggaagaggatggaggtcgggcagcaggccgtagaagtctggcagggcctggccctgctgtcggaagct
hS3   -------------------gtcgggcagcaggccgtagaagtctggcagggcctggccctgctgtcggaagct
h1-4  tatgcctggaagaggatggaggtcgggcagcaggcc-------------------------------------
h1-5  tatgcc-------------------------------------------------------------------
hS4   tatgcctggaagaggatggagccgtgggag-------------------------------------------
h1-1  -------------------------------------------------------------------------
h2-1  ------------------------------------------------------------------------- hWT   gtcctgcggggccaggccctgttggtcaactcttcccagccgtgggagcccctgcagctgcatgtggataaagcc
hS3   gtcctgcggggccaggccctgttggtcaactcttcccagccgtgggagcccctgcagctgcatgtggataaagcc
h1-4  -----------------ctgttggtcaactcttcccagccgtgggagcccctgcagctgcatgtggataaagcc
h1-5  -----------------ctgttggtcaactcttcccagccgtgggagcccctgcagctgcatgtggataaagcc
hS4   ------------------------------------------cccctgcagctgcatgtggataaagcc
h1-1  --------------gccctgttggtcaactcttcccagccgtgggagcccctgcagctgcatgtggataaagcc
h2-1  -------------------------------------------------------------------------

418
hWT   gtcagtggccttcgcagcctcaccactctgcttcgggctctgggagcccagaaggaagccatctcccctccagat
hS3   gtcagtggccttcgcagcctcaccactctgcttcgggctctgggagcccagaaggaagccatctcccctccagat
h1-4  gtcagtggccttcgcagcctcaccactctgcttcgggctctgggagcccagaaggaagccatctcccctccagat
h1-5  gtcagtggccttcgcagcctcaccactctgcttcgggctctgggagcccagaaggaagccatctcccctccagat
hS4   gtcagtggccttcgcagcctcaccactctgcttcgggctctgggagcccagaaggaagccatctcccctccagat
h1-1  gtcagtggccttcgcagcctcaccactctgcttcgggctctgggagcccagaaggaagccatctcccctccagat
h2-1  ------------------------------------------------------------------------- hWT   gcggcctcagctgctccactccgaacaatcactgctgacactttccgcaaactcttccgagtctactccaatttc
hS3   gcggcctcagctgctccactccgaacaatcactgctgacactttccgcaaactcttccgagtctactccaatttc
h1-4  gcggcctcagctgctccactccgaacaatcactgctgacactttccgcaaactcttccgagtctactccaatttc
h1-5  gcggcctcagctgctccactccgaacaatcactgctgacactttccgcaaactcttccgagtctactccaatttc
hS4   gcggcctcagctgctccactccgaacaatcactgctgacactttccgcaaactcttccgagtctactccaatttc
h1-1  gcggcctcagctgctccactccgaacaatcactgctgacactttccgcaaactcttccgagtctactccaatttc
h2-1  --------------------caatcactgctgacactttccgcaaactcttccgagtctactccaatttc
```

Fig 3b

```
hWT  ctccggggaaagctgaagctgtacacaggggaggcctgcaggacaggggacagatga
hS3  ctccggggaaagctgaagctgtacacaggggaggcctgcaggacaggggacagatga
h1-4 ctccggggaaagctgaagctgtacacaggggaggcctgcaggacaggggacagatga
h1-5 ctccggggaaagctgaagctgtacacaggggaggcctgcaggacaggggacagatga
hS4  ctccggggaaagctgaagctgtacacaggggaggcctgcaggacaggggacagatga
h1-1 ctccggggaaagctgaagctgtacacaggggaggcctgcaggacaggggacagatga
h2-1 ctccggggaaagctgaagctgtacacaggggaggcctgcaggacaggggacagatga
```

Fig. 5
A
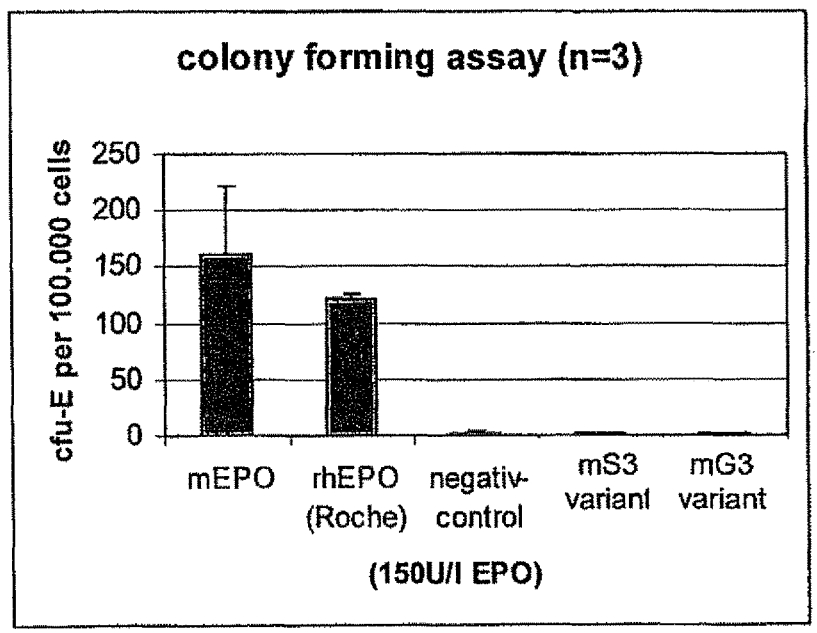
B
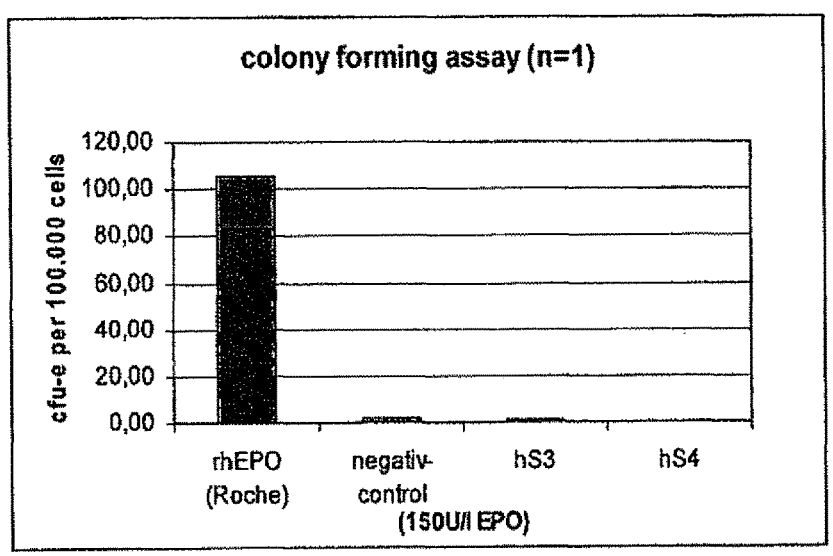

Fig. 7
A
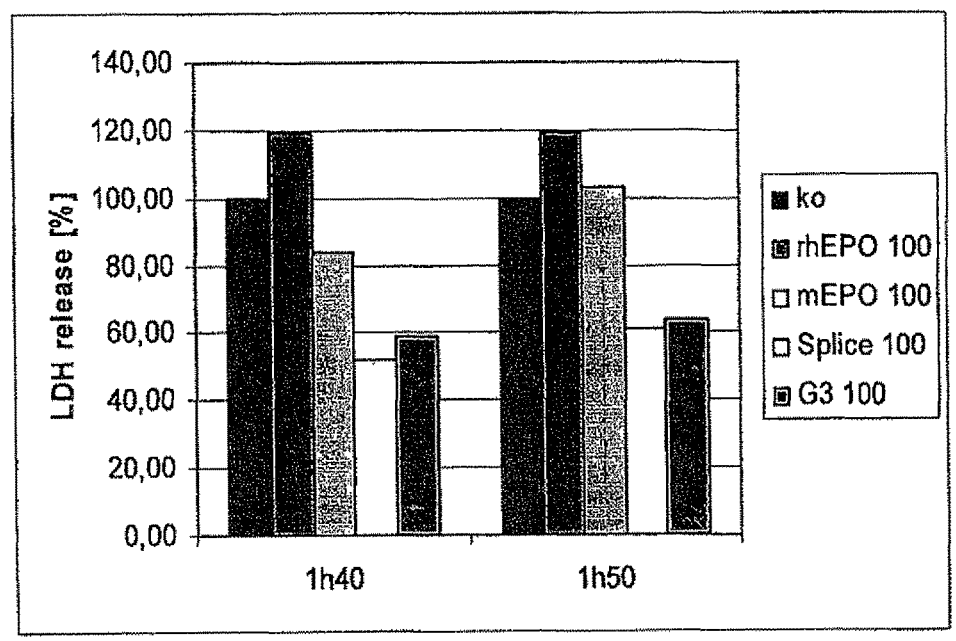
B
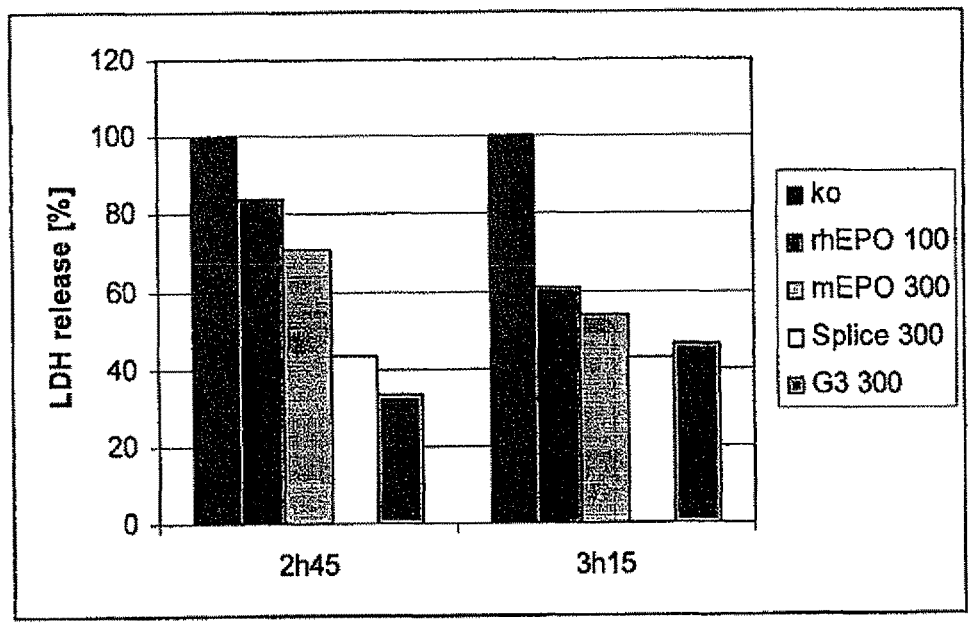

Fig. 8
A
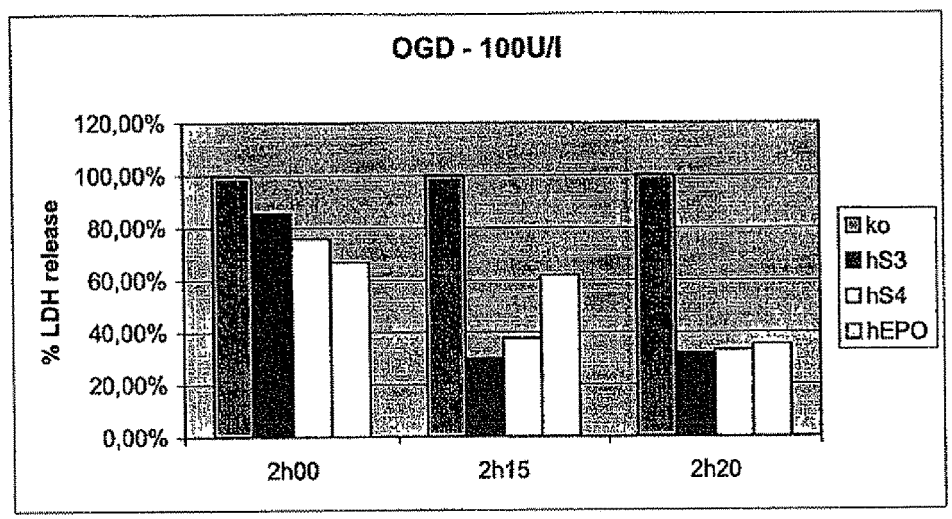
B
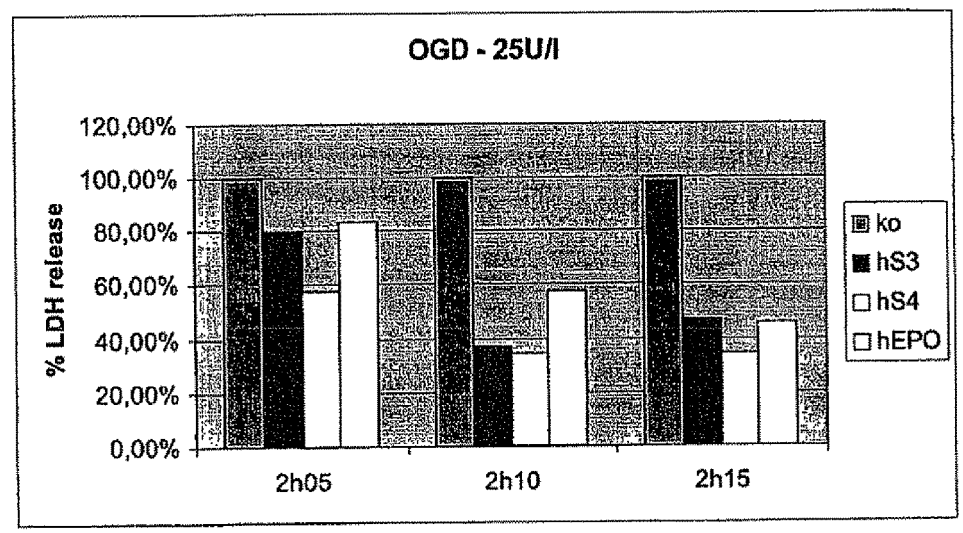

Fig. 9
A
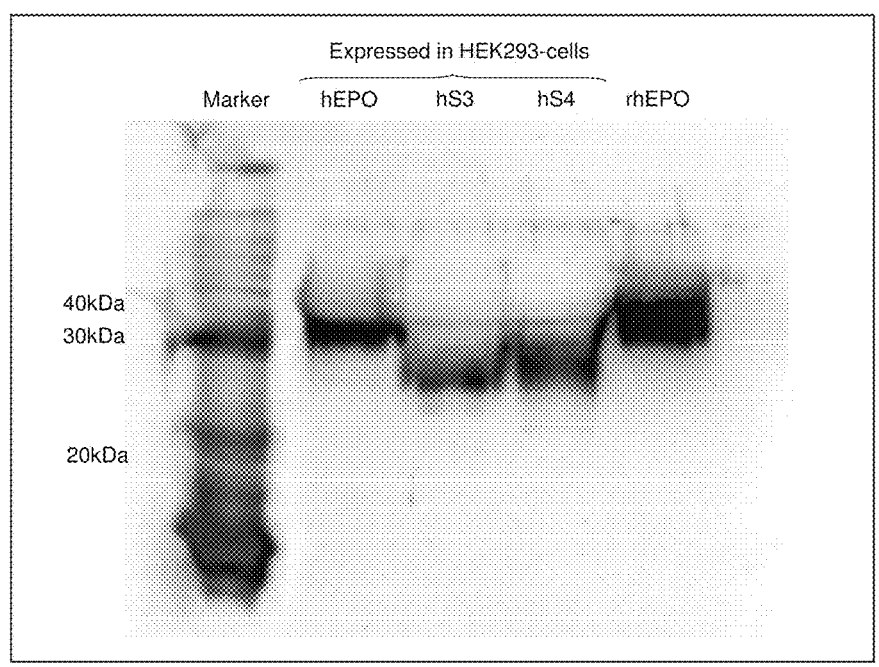
B
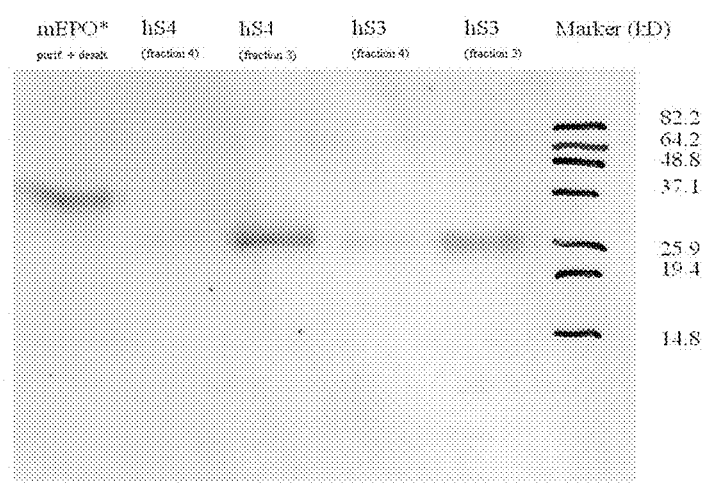

Fig. 15
A
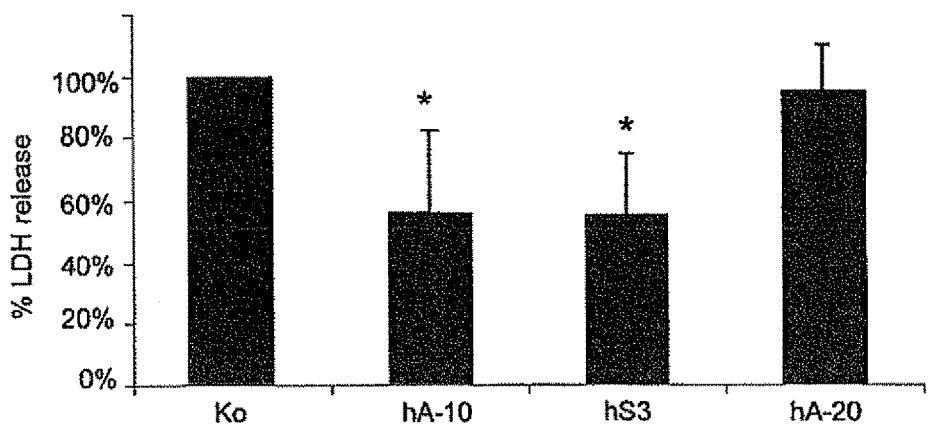
B
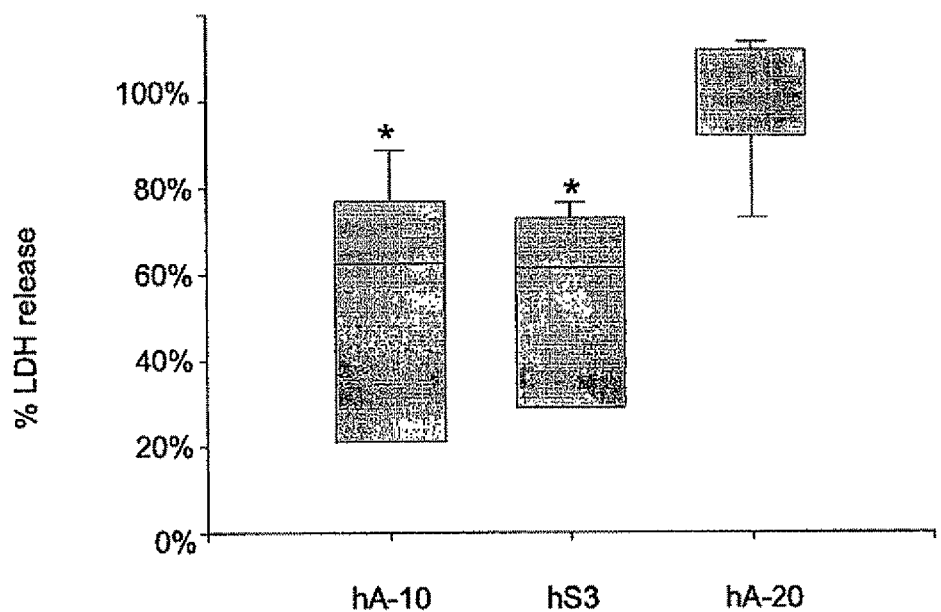

Fig. 17

```
atgggggtgcacgaatgtcctgcctggctgtggcttctcctgtccctgctgtcgctccctctgggcctcccagtc
Atgggggtgcacgaatgtcctgcctggctgtggcttctcctgtccctgctgtcgctccctctgggcctcccagtc
Atgggggtgcacgaatgtcctgcctggctgtggcttctcctgtccctgctgtcgctccctctgggcctcccagtc
Atgggggtgcacgaatgtcctgcctggctgtggcttctcctgtccctgctgtcgctccctctgggcctcccagtc
Atgggggtgcacgaatgtcctgcctggctgtggcttctcctgtccctgctgtcgctccctctgggcctcccagtc
Atgggggtgcacgaatgtcctgcctggctgtggcttctcctgtccctgctgtcgctccctctgggcctcccagtc ctgggcgccccaccacgcctcatctgtgacagccgagtcctggagaggtacctcttggaggccaaggaggccgag
ctgggcgccccaccacgcctcatctgtgacagccgagtcctggagaggtacctcttggaggccaaggaggccgag
ctgggcgccccaccacgcctcatctgtgacagccgagtcctggaggcgtacctcttggaggccaaggaggccgag
ctgggcgccccaccacgcctcatctgtgacagccgagtcctggaggagtacctcttggaggccaaggaggccgag
ctgggcgccccaccacgcctcatctgtgacagccgagtcctggaggagtacctc---------------------
ctgggcgccccaccacgcctcatc---------------------------------------------------- aatatcacgacgggctgtgctgaacactgcagcttgaatgagaatatcactgtcccagacaccaaagttaatttc
aatatcacg-------------------------------------------------------------------
aatatcacg-------------------------------------------------------------------
aatatcacg-------------------------------------------------------------------
----------------------------------------------------------------------------
---------------------------------------------------------------------------- tatgcctggaagaggatggaggtcgggcagcaggccgtagaagtctggcagggcctggccctgctgtcggaagct
----------------------------------------------------------------------------
----------------------------------------------------------------------------
----------------------------------------------------------------------------
----------------------------------------------------------------------------
---------------------------------------------------------------------------- gtcctgcggggccaggccctgttggtcaactcttcccagccgtgggagcccctgcagctgcatgtggataaagcc
----------------------------------------------------------------------------
----------------------------------------------------------------------------
----------------------------------------------------------------------------
----------------------------------------------------------------------------
---------------------------------------------------------------------------- gtcagtggccttcgcagcctcaccactctgcttcgggctctgcgagcccagaaggaagccatctcccctccagat
----------------------------------------------------------------------------
----------------------------------------------------------------------------
----------------------------------------------------------------------------
----------------------------------------------------------------------------
---------------------------------------------------------------------------- gcggcctcagctgctccactccgaacaatcactgctgacactttccgcaaactcttccgagtctactccaatttc
----------------------------------------------------------------------------
----------------------------------------------------------------------------
----------------------------------------------------------------------------
----------------------------------------------------------------------------
---------------------------------------------------------------------------- ctccggggaaagctgaagctgtacacaggggaggcctgcaggacaggggacagatga
----------------------------------------------------------
----------------------------------------------------------
----------------------------------------------------------
----------------------------------------------------------
---------------------------------------------------------- hWT
hA
hAmA
hAmE
hA-10
hA-20
```

Fig. 18 hA (hWT-EPO Helix A) - SEQ ID NO 55 atgggggtgcacgaatgtcctgcctggctgtggcttctcctgtccctgctgtcgctccctct
gggcctcccagtcctgggcgccccaccacgcctcatctgtgacagccgagtcctggagaggt
acctcttggaggccaaggaggccgagaatatcacg hAmA (Mutant Alanin hWT-EPO Helix A) SEQ ID NO 56
atgggggtgcacgaatgtcctgcctggctgtggcttctcctgtccctgctgtcgctccctct
gggcctcccagtcctgggcgccccaccacgcctcatctgtgacagccgagtcctggaggcgt
acctcttggaggccaaggaggccgagaatatcacg hAmE (Mutant Glutamic-Acid hWT-EPO Helix A)  SEQ ID NO 57
atgggggtgcacgaatgtcctgcctggctgtggcttctcctgtccctgctgtcgctccctct
gggcctcccagtcctgggcgccccaccacgcctcatctgtgacagccgagtcctggaggagt
acctcttggaggccaaggaggccgagaatatcacg hA-10 (hWT-EPO Helix A minus 10aa) SEQ ID NO 58
atgggggtgcacgaatgtcctgcctggctgtggcttctcctgtccctgctgtcgctccctct
gggcctcccagtcctgggcgccccaccacgcctcatctgtgacagccgagtcctggagaggt
acctc hA-20 (hWT-EPO Helix A minus 20aa) SEQ ID NO 59
atgggggtgcacgaatgtcctgcctggctgtggcttctcctgtccctgctgtcgctccctct
gggcctcccagtcctgggcgccccaccacgcctcatc

Fig. 19

A - hA DNA without leader:

(hWT-EPO Helix A without leader transport sequence) – SEQ ID NO 60 – (mature exported protein)

5'-gccccaccacgcctcatctgtgacagccgagtcctggagaggtacctcttggaggccaaggaggccgagaatatcacg....-3'

Leader-Sequence (SEQ ID NO 63):

5'-atgggggtgcacgaatgtcctgcctggctgtggcttctcctgtccctgctgtcgctccctctgggcctcccagtcctgggcg-3'

B - hA amino acid without leader:

(hWT-EPO Helix A without leader transport sequence) – SEQ ID NO 61 (mature exported proteins):

APPRLICDSRVLERYL

Leader-Sequence (SEQ ID NO 62): MGVHECPAWLWLLLSLLSLPLGLPVLG

1 …

ERYTHROPOIETIN VARIANTS

This application is a continuation of U.S. patent application Ser. No. 11/914,368, filed Nov. 13, 2007, now abandoned which is a U.S. National Stage Application based on International Patent Application No. PCT/EP2006/004564, filed May 15, 2006, which is based on European Patent Application No. 05010473.3, filed May 13, 2005.

SEQUENCE LISTING

The instant application contains a Sequence Listing which has been submitted in ASCII format via EFS-Web and is hereby incorporated by reference in its entirety. Said ASCII copy, created on Aug. 14, 2014, is named SCH1500US_SequenceListing.txt and is 50 kilobytes in size.

FIELD OF THE INVENTION

The present invention relates to novel endogenous variants of erythropoietin (EPO) and their use for treatment or prevention of a condition associated with tissue damage due to cell death (apoptosis, necrosis) and inflammation, in particular for neuroprotection, e.g. treatment of acute (for example stroke) and chronic disease (for example ALS) of the nervous system.

BACKGROUND OF THE INVENTION

Stroke is a debilitating disease which affects more than 400,000 persons per year in the United States and is the third most common cause of death in the United States. In addition one-half of neurology inpatients have stroke related problems. At current trends, this number is projected to jump to one million per year by the year 2050. When the direct costs (care and treatment) and the indirect costs (lost productivity) of strokes are considered together, strokes put a burden of $43.3 billion per year on the society of the United States alone. About ⅓ of patients die in the first three months, ⅓ remain with severe disabilities, and only ⅓ recover with acceptable outcome. In 1990 cerebrovascular diseases were the second leading cause of death worldwide, killing over 43 million people world wide. Thus, from a public health perspective, stroke is one of the most relevant diseases.

Stroke is characterized by the sudden loss of circulation to an area of the brain, resulting in a corresponding loss of neurologic function. Also called cerebrovascular accident or stroke syndrome, stroke is a nonspecific term encompassing a heterogeneous group of pathophysiologic causes, including thrombosis, embolism, and hemorrhage. Strokes currently are classified as either hemorrhagic or ischemic. Acute ischemic stroke refers to strokes caused by thrombosis or embolism and account for 80% of all strokes.

Ischemic strokes result from blockage of the arteries that supply the brain, most commonly in the branches of the internal carotid arteries. The blockage usually results when a piece of a blood clot (thrombus) or of a fatty deposit (atheroma) due to atherosclerosis breaks off (becoming an embolus), travels through the bloodstream, and lodges in an artery that supplies the brain. Blood clots may form when a fatty deposit in the wall of an artery ruptures. The rupture of such a fatty deposit may also form when a large fatty deposit slows blood flow, reducing it to a trickle. Blood that flows slowly is more likely to clot. Thus, the risk of a clot forming in and blocking a narrowed artery is high. Blood clots may also form in other areas, such as in the heart or on a heart valve. Strokes due to such blood clots are most common among people who have recently had heart surgery and people who have a heart valve disorder or an abnormal heart rhythm (arrhythmia), especially atrial fibrillation. Also, in certain disorders such as an excess of red blood cells (polycythemia), the risk of blood clots is increased because the blood is thickened.

An ischemic stroke can also result, if the blood flow to the brain is reduced, as may occur when a person loses a lot of blood or has very low blood pressure. Occasionally, an ischemic stroke occurs when blood flow to the brain is normal but the blood does not contain enough oxygen. Disorders that reduce the oxygen content of blood include severe anemia (a deficiency of red blood cells), suffocation, and carbon monoxide poisoning. Usually, brain damage in such cases is widespread (diffuse), and coma results. An ischemic stroke can occur, if inflammation or infection narrows blood vessels that supply the brain. Similarly, drugs such as cocaine and amphetamines can cause spasm of the arteries, which can lead to a narrowing of the arteries supplying the brain to such an extent that a stroke is caused.

The brain requires glucose and oxygen to maintain neuronal metabolism and function. The inadequate delivery of oxygen to the brain leads to a hypoxia and ischemia results from insufficient cerebral blood flow. The consequences of cerebral ischemia depend on the degree and the duration of reduced cerebral blood flow. Neurons can tolerate ischemia for 30-60 minutes. If flow is not re-established to the ischemic area, a series of metabolic processes ensue. The neurons become depleted of ATP and switch over to anaerobic glycolysis, a much less efficient pathway. Lactate accumulates and the intracellular pH decreases. Without an adequate supply of ATP, ion pumps in the plasma membrane fail. The resulting influx of sodium, water, and calcium into the cell causes rapid swelling of neurons and glial cells. Membrane depolarization also stimulates the massive release of the amino acids glutamate and aspartate, both of which act as excitatory neurotransmitters in the brain. Glutamate further activates sodium and calcium ion channels in the neuronal cell membrane namely the well characterized N-methyl-D-aspartate (NMDA) calcium channel. Excessive calcium influx causes the disordered activation of a wide range of enzyme systems (proteases, lipases, and nucleases). These enzymes and their metabolic products, such as oxygen free radicals, damage cell membranes, genetic material, and structural proteins in the neurons, ultimately leading to the cell death of neurons (Dirnagl, U. et al. (1999) *Trends Neurosci*, 22: 391-397).

Strokes begin suddenly, develop rapidly, and cause death of brain tissue within minutes to days. In the ischemic brain, we commonly distinguish two tissue volumes—the core of the infarction and the surrounding zone, known as ischemic penumbra—the underperfused and metabolically compromised margin surrounding the irrevocably damaged core. Core and penumbra are characterized by two different kinds of cell death: necrosis and apoptosis (which is also called programmed cell death or delayed neuronal cell death). The severe perfusion deficit in the core causes a breakdown of metabolic processes, cellular energy supply and ion homeostasis, which causes the cells to lose their integrity within minutes. Thus, acute necrosis of cell and tissue prevails in the core. In the penumbra, some residual perfusion is maintained by collateral vessels, which may be unable to maintain the full functional metabolism, but prevents immediate structural disintegration. However, over time (hours to several days), the alteration of cellular homeostasis causes more and more cells to die, and the volume of the infarction increases. The penumbra has thus to be considered as tissue at risk during the materation of the infarct. In this region, apoptosis and inflammatory signaling cascades play an important role. It may initially constitute 50% of the volume that will end up as infarction. The mechanisms that lead to delayed cell death provide targets for a specific neuroprotective therapy in brain regions challenged by ischemia, but which are still viable.

Therapeutic options so far are highly disappointing: Thrombolysis with rtPA, the only therapy with proven efficacy in a major clinical trial (NINDS), is only effective within a three hour time window, limiting its application to only a few percent of patients with ischemic stroke. In other words, besides basic supportive therapy, at present more than 95% of strokes cannot be treated specifically. This is in sharp contrast to our knowledge concerning the basic pathophysiology of this disease, which has emerged over the last decade. In particular, extensive knowledge has accumulated on mechanisms of parenchymal brain damage and endogenous neuroprotection, as well as functional and structural reorganization.

Recently, attention has focused on potential therapeutic roles for endogenous brain proteins possessing neuroprotective properties. EPO, a glycoprotein hormone produced primarily by cells of the peritubular capillary endothelium of the kidney, which is a member of the growth hormone/prolacton cytokine family (Thu Y. and D'Andrea A. D: (1994) *Curr. Opin. Hernatal.* 1: 113-118) is a promising candidate. Although EPO was first characterized and is now widely known for its role as a haematopoietic hormone the detection of EPO and its receptor (EPOR) in rodent and human brain tissue as well as in cultured neurons and astrocytes expanded the search for other biological roles of EPO.

In the brain, a paracrine EPO/(Epo-R)$_2$ system exists independent of the endocrine system of adult erythropoiesis; neurones express (Epo-R)$_2$ and astrocytes produce EPO (Ruscher et al. (2002) *J. Neurosci.* 22, 10291-301; Prass et al. (2003) *Stroke* 34, 1981-1986). It was demonstrated in vitro and in vivo that EPO is a potent inhibitor of neuronal apoptosis induced by ischemia and hypoxia (Ruscher et al. (2002) *J. Neurosci,* 22, 10291-301; Bemaudin, M., et al. (1999) *J Cereb Blood Flow Metab.* 19: 643-51; Morishita, E., et al. (1997) *Neuroscience.* 76: 105-16). It was reported by several groups that addition of EPO to neuronal cultures protects against hypoxic and glutamic acid toxicity (Henn F. A: and Braus D. F. (1999) *Eur. Arch. Psychiatry Clin. Neurosci.* 249: 48-56, Vogeley K. et al. (2000) *Am. J. Psychiatry* 157: 34-39) and reduces neurologic dysfunction in rodent models of strike (Brines M. L. et al. (2000) *Proc. Natl. Acad. Sci. U.S.A.* 97: 10526-10531 and Bemaudin et al. (1999) *J. Cereb. Blood Flow Metab.* 10: 643-.651). The promising results of these experiments have been corroborated in human studies wherein it was shown that EPO therapy for acute stroke is safe and might be beneficial (Ehrenreieh H. et al. (2002) Mol. Medicine. 8: 495-505) and WO 00/35475 A2. These cell and more particular neuroprotective properties of EPO have led to further research in this area to substantiate these findings in larger trial and the use of EPO is now proposed in other indication as well including, for example, schizophrenia (Ehrenreich H et al. (2004) *Molecular Psychiatry* 9: 42-54 and WO 02/20031 A2).

For the application of EPO to prevent tissue damage the hematopoietic activity is often not required and might be detrimental if large amounts of EPO are administered to treat or atmliorate the effects of, hypoxia or ischemia induced tissue damage. Therefore, attempts have been made to create EPO variants, which only exhibit the cell protective property but not the hematopoietic properties. US 2003/0130197 describes peptide mimetics of EPO for the treatment of neurodegenerative disorders, which bear no sequence homology to naturally occurring EPO or fragments thereof. U.S. Pat. No. 6,531,121 discloses a asialoerythropoietin which is generated by complete desialylation of recombinant EPO showed an increased ability to cross the endothelial cell barrier and had a decreased hematopoietic activity. Carbamylated erythropoietin (CEPO) was also shown to exhibit a tissue protective effect but no erythropoietic effect (Leist et al. (2004) *Science* 305: 239-242 and WO 2005/025606 A1.

Finally, it was shown that a 17-mer peptide of EPO inhibited cell death of two neuronal cell lines, SK-N-MC and NS20Y (Campana W. M. et al. (1998) *Int J. Mol. Medicine* 1: 235-241), while at the same time having no hematopoietic activity. However, 1 ng/ml of the EPO peptide was needed to elicit the same antiapoptotic effect as 100 pg/ml recombinant EPO (rhEPO) in NS20Y cells and as 400 pg/ml rhEPO in SK-N-MC cells. Given the apparent molecular weight of rhEPO of about 66.000 g/mol (the calculated molecular weight is about 33.000 g/mol but does not include the weight of oligosaccharide residues comprised in rhEPO) and of about 1.900 g/mol of the EPO peptide a concentration of 1.52 pmol/l and 6.06 pmol/l, respectively, of rhEPO and 1 nmol/l of the EPO peptide elicited the same level of a cell protective effect. Consequently, the EPO peptide is between 650-fold to 165-fold less active than rhEPO in prevention of cell death. It is evident from this figures that the EPO region comprised in the 17-mer does not play a major role in the cell protective function of EPO. Therefore, all EPO variants, which have a decreased hematopoietic activity known in the prior art suffer from the disadvantage that they are not natural occurring since they have either lost their natural glycosylation or they are artificial truncations and/or they have vastly diminished cell protective activity, if compared to rhEPO. Therefore, there is a need in the prior art to provide an EPO derivative, which is close to the naturally occurring EPO and which has the same or better tissue protecting activity as rhEPO but less or no hematopoietic, in particular no erythropoietic activity.

This problem is solved by the provision of new EPO variants, which were found to occur naturally in human and mouse tissue (brain, kidney) and which exhibit a cell protective activity similar or better to rhEPO but which do not exhibit any significant hematopoietic activity.

SUMMARY OF THE INVENTION

In one aspect the present invention is concerned with an EPO variant encoding polynucleotide selected from the group consisting of:
(a) polynucleotides encoding at least the mature form of the polypeptides termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;
(b) polynucleotides having the coding sequence, as shown in SEQ ID NOs: 1, 3, 5, 7, 9, 11, 13, 15, 17, 19, and 21 encoding at least the mature form of the polypeptide;
(c) polynucleotide encoding a humanized version of the polypeptides mS, mG3, mG5, m301 and mK3 having the deduced amino acid sequence as shown in SEQ ID NOs 14, 16, 18, 20, and 22, (d) polynucleotides encoding a polypeptide comprising a fusion of an amino acid sequence selected from the group of amino acid sequences as shown in SEQ D3 NO 24, 26, 28, and 30, at the N-terminus of an amino acid sequence selected from the group of amino acid sequences as shown in SEQ ID NO 32, 34, 36, and 38;

(e) polynucleotides comprising a fusion of polynucleotide sequences selected from the group of polynucleotide sequences as shown in SEQ ID NO 23, 25, 27, and 29, 5' of a polynucleotide sequence selected from the group of polynucleotide sequences as shown in SEQ ID NO 31, 33, 35, and 37;

(f) polynucleotides encoding a derivative of a polypeptide encoded by a polynucleotide of any one of (a) to (e), wherein in said derivative between 1 and 10 amino acid residues are conservatively substituted compared to said polypeptide, and said derivative has cell protective and in particular neuroprotective activity but essentially no hematopoietic activity;

(g) polynucleotides encoding a fragment of a polypeptide encoded by a polynucleotide of any one of (a) to (f), wherein in said fragment between 1 and 10 amino acid residues are N- and/or C-terminally deleted and/or between 1 and 10 amino acids are deleted N- and or C-terminally of the junction compared to said polypeptide, and said fragment has cell protective and in particular neuroprotective activity but essentially no hematopoietic activity;

(h) polynucleotides which are at least 50% identical to a polynucleotide as defined in any one of (a) to (g) and which code for a polypeptide having cell protective and in particular neuroprotective activity but essentially no hematopoietic activity; and (i) polynucleotides the complementary strand of which hybridizes under stringent conditions to a polynucleotide as defined in any one of (a) to (h) and which code for a polypeptide having cell protective and in particular neuroprotective activity but essentially no hematopoietic activity;

or the complementary strand of such a polynucleotide.

A further aspect of the present invention is a homolog of an erythropoietin (EPO) variant encoding polynucleotide from another higher eukaryotic species.

A further aspect of the present invention is an EPO variant encoding polynucleotide selected from the group consisting of (a) polynucleotides encoding an EPO variant polypeptide, which comprises the N-terminal part of full length EPO including helix A and which lacks at least one of the following:
  (i) a fragment of at least 10 amino acids, preferably 11, 12, 13, 14, 15, 16, 17, 18, 19 or 20 amino acids between helix A and helix B;
  (ii) a fragment of at least 10 amino acids, preferably 11, 12, 13, 14, 15, 16, 17, 18, 19, 20, 21, 22, 23, 24, 25, 26, 27 or 28 amino acids of helix B;
  (iii) a fragment of at least 2 amino acids, preferably 3, 4, 5, or 6 amino acids between helix B and helix C;
  (iv) a fragment of at least 10 amino acids, preferably 11, 12, 13, 14, 15, 16, 17, 18, 19, 20, 21, 22, or 23 amino acids of helix C;
  (v) a fragment of at least 10 amino acids, preferably 11, 12, 13, 14, 15, 16, 17, 18, 19, 20, 21, 22, 23, 24, 25, 26, or 27 amino acids between helix C and D; and/or
  (vi) a fragment of at least 10 amino acids, preferably 11, 12, 13, 14, 15, 16, 17, 18, 19, 20, 21, or 22 of helix D;

wherein said variant has cell protective and in particular neuroprotective activity but essentially no hematopoietic activity.

(b) polynucleotides encoding a derivative of a polypeptide encoded by a polynucleotide of any one of (a), wherein in said derivative between 1 and 10 amino acid residues are conservatively substituted compared to said polypeptide, and said derivative has cell protective and in particular neuroprotective activity but essentially no hematopoietic activity;

(c) polynucleotides the complementary strand of which hybridizes under stringent conditions to a polynucleotide as defined in any one of (a) to (b) and which code for a polypeptide having cell protective and in particular neuroprotective activity but essentially no hematopoietic activity;

or the complementary strand of such a polynucleotide.

In a preferred aspect the polynucleotide of the present invention which is DNA, genomic DNA or RNA.

In another aspect the present invention is concerned with a vector containing the polynucleotide of the present invention. It is preferred that the polynucleotide contained in the vector is operatively linked to expression control sequences allowing expression in prokaryotic and/or eukaryotic host cells.

Another aspect of the invention is a host cell genetically engineered with the polynucleotide of the present invention or the vector of the present invention.

Another aspect of the invention is a transgenic non-human animal containing a polynucleotide of the present invention, a vector of the present invention and/or a host cell of the present invention.

Another aspect of the invention is a process for producing an EPO variant polypeptide encoded by the polynucleotide of the present invention comprising: culturing the host cell of the present invention and recovering the polypeptide encoded by said polynucleotide.

In a preferred embodiment the process of the present invention, further comprises the step of modifying said EPO variant, wherein the modification is selected from the group consisting of oxidation, sulfation, phosphorylation, addition of oligosaccharides or combinations thereof.

Another aspect of the invention is a process for producing cells capable of expressing at least one of the EPO variants comprising genetically engineering cells in vitro with the vector of the invention, wherein said EPO variant polypeptide(s) is(are) encoded by a polynucleotide of the invention.

Another aspect of the invention is a polypeptide having the amino acid sequence encoded by a polynucleotide of the present invention or obtainable by the process of the present invention.

Another aspect of the invention is an antibody specifically binding to the polypeptide of the present invention.

Another aspect of the invention is a pharmaceutical composition comprising a polynucleotide of the present invention, a vector of the present invention, a host cell of the present invention, a polypeptide of the present invention and/or an antibody of the present invention and a one or more pharmaceutically acceptable carrier.

Another aspect of the invention is the use of a polynucleotide of the present invention, a vector of the present invention, a host cell of the present invention, a polypeptide of the present invention for the manufacture of a medicament for the treatment or prevention of a condition associated with tissue damage due to cell death, e.g. apoptosis and necrosis as well as by inflammation.

In a preferred use of the present invention cell death is induced by ischemia, hypoxia, bacterial infection, viral infection, autoimmunologically, traumatically, chemically (e.g. metabolically, toxically) induced, or radiation induced.

In a preferred use of the present invention the condition is an acute neurodegenerative/neuroinflammatory disorder or a chronic neurodegenerative/neuroinflammatory disorder, is an acute or chronic disorder of the heart (e.g. myocardial infarction), lung (e.g. asthma, chronic obstructive lung disease), kidney (e.g. glomerulonephritis), liver (e.g. chronic liver failure) or pancreas (e.g. pancreatitis) or said condition is associated with an organ (e.g. kidney or liver) or cell transplantation (e.g. stem cell).

Preferably the acute neurodegenerative and/or neuroinflammatory disorder is selected from the group consisting of cerebral ischemia or infarction including embolic occlusion and thrombotic occlusion, reperfusion following acute ischemia, perinatal hypoxic-ischemic injury, cardiac arrest, intracranial hemorrhage, subarachnoidal hemorrhage and intracranial lesions (e.g. CNS trauma), spinal cord lesions, intravertebral lesions, whiplash shaken infant syndrome, infectious encephalitis (e.g. herpes encephalitis), meningitis (e.g. bacterial), headache (e.g. migraine).

Preferably the chronic neurodegenerative/neuroinflammatory disorder is selected from the group consisting of dementias (e.g. Alzheimer's disease, vascular dementias), Pick's disease, diffuse Lewy body disease, progressive supranuclear palsy (Steel-Richardson syndrome), multiple sclerosis, multiple system atrophy (including Shy-Drager syndrome), chronic epileptic conditions associated with neurodegeneration, motor neuron diseases, degenerative ataxias, cortical basal degeneration, ALS-Parkinson's Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sachs disease, Sandhoff disease, familial spastic disease, spastic paraparesis, progressive multifocal leukoencephalopathy, familial dysautonomia (Riley-Day syndrome), polyneuropathies (e.g. diabetic, alcohol-toxic, Guillain-Barré-Syndrome, chronic inflammatory demyelinating polyneuropathy), prion diseases, addiction, affective disorders (e.g. depression), schizophrenic disorders, chronic fatigue syndrome, chronic pain (e.g. lower back pain).

In a preferred use of the present invention the condition is aging.

In a preferred use of the present invention the medicament is administered prior to or after the onset of said condition.

DETAILED DESCRIPTION OF THE INVENTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The present invention is based on the surprising observation that EPO variants are expressed in neuronal tissue and the determination that the variants protected neurons from damage induced by oxygen and glucose deprivation but did not show hematopoietic activity. This behavior makes them suitable for use as therapeutics in situations where the hematopoietic function of EPO is not required or deleterious. Accordingly a first aspect of the present invention is an EPO variant encoding polynucleotide selected from the group consisting of:

(a) polynucleotides encoding at least the mature form of the polypeptides termed hs3, h1-4, h1-5, hs4, h1-1, h2-1, mS, mG3, mG5, m301 and mK3 having the deduced amino acid sequence as shown in SEQ ID NOs 2, 4, 6, 8, 10, 12, 14, 16, 18, 20, and 22, respectively;

(b) polynucleotides having the coding sequence, as shown in SEQ ID NOs: 1, 3, 5, 7, 9, 11, 13, 15, 17, 19, and 21 encoding at least the mature form of the polypeptide;

(c) polynucleotide encoding a humanized version of the polypeptides mS, mG3, mG5, m301 and mK3 having the deduced amino acid sequence as shown in SEQ ID NOs 14, 16, 18, 20, and 22;

(d) polynucleotides encoding a polypeptide comprising a fusion of an amino acid sequence selected from the group of amino acid sequences as shown in SEQ ID NO 24, 26, 28, and 30, at the N-terminus, preferably directly, i.e. without any intervening amino acids, of an amino acid sequence selected from the group of amino acid sequences as shown in SEQ ID NO 32, 34, 36, and 38;

(e) polynucleotides comprising a fusion of polynucleotide sequences selected from the group of polynucleotide sequences as shown in SEQ ID NO 23, 25, 27, and 29, 5', preferably directly 5', i.e. without any intervening polynucleotides, of a polynucleotide sequence selected from the group of polynucleotide sequences as shown in SEQ ID NO 31, 33, 35, and 37;

(f) polynucleotides encoding a derivative of a polypeptide encoded by a polynucleotide of any one of (a) to (e), wherein in said derivative between 1 and 10 amino acid residues are conservatively substituted compared to said polypeptide, and said derivative has cell protective and in particular neuroprotective activity but essentially no hematopoietic activity;

(g) polynucleotides encoding a fragment of a polypeptide encoded by a polynucleotide of any one of (a) to (I), wherein in said fragment between 1 and 10 amino acid residues are N- and/or C-terminally deleted and/or between 1 and 10 amino acids are deleted N- and or C-terminally of the junction compared to said polypeptide, and said fragment has cell protective and in particular neuroprotective activity but essentially no hematopoietic activity;

(h) polynucleotides which are at least 50% identical to a polynucleotide as defined in any one of (a) to (g) and which code for a polypeptide having cell protective and in particular neuroprotective activity but essentially no hematopoietic activity; and (i) polynucleotides the complementary strand of which hybridizes under stringent conditions to a polynucleotide as defined in any one of (a) to (h) and which code for a polypeptide having cell protective and in particular neuroprotective activity but essentially no hematopoietic activity;

or the complementary strand of such a polynucleotide.

The invention further relates to a peptide of an EPO variant encoding polynucleotide selected from the group consisting of:
(a) polynucleotides encoding the polypeptides termed ha, hAma, hAmE, hA-20 and hatransport sequence, having the deduced amino acid sequence as shown in SEQ ID NOs 50, 51, 52, 53 and 60 respectively;
(b) polynucleotides having the coding sequence, as shown in SEQ ID NOs: 55, 56, 57, 58 and 61 encoding at least the mature form of the polypeptide;
(c) polynucleotides encoding a derivative of a polypeptide encoded by a polynucleotide of any one of (a) to (b), wherein in said derivative between 1 and 10 amino acid residues are conservatively substituted compared to said polypeptide, and said derivative has cell protective and in particular neuroprotective activity but essentially no hematopoietic activity;
(d) polynucleotides encoding a fragment of a polypeptide encoded by a polynucleotide of any one of (a) to (b), wherein in said fragment between 1 and 10 amino acid residues are N- and/or C-terminally deleted and/or between 1 and 10 amino acids are deleted N- and or C-terminally of the junction compared to said polypeptide, and said fragment has cell protective and in particular neuroprotective activity but essentially no hematopoietic activity;
(e) polynucleotides which are at least 50% identical to a polynucleotide as defined in any one of (a) to (b) and which code for a polypeptide having cell protective and in particular neuroprotective activity but essentially no hematopoietic activity; and
(i) polynucleotides the complementary strand of which hybridizes under stringent conditions to a polynucleotide as defined in any one of (a) to (h) and which code for a polypeptide having cell protective and in particular neuroprotective activity but essentially no hematopoietic activity;
or the complementary strand of such a polynucleotide.

In a further aspect the polynucleotides of the present invention comprise homologs of the EPO variants of the present invention derived from another higher eukaryotic species, in particular from mammals, more preferably from non-human primates; from rodents, e.g. rat, or guinea pig; ruminant, e.g. cow; or sheep; horse; pig, rabbit; dog; or cat, which have cell protective and in particular neuroprotective activity but essentially no hematopoietic activity. In this context the term homolog refers to a polynucleotide encoding a EPO variant derived from another species, which comprises essentially the same deletion as the polynucleotides according to SEQ ID NO 1, 3, 5, 7, 9, 11, 13,1 15, 17, 19, 21, 55, 56, 57, 58 or 61. A deletion of a polynucleotide is considered to be essentially the same, if it involves the deletion of polynucleotides encoding a polypeptide, which is homologous to the respectively deleted polypeptides in the EPO variant polypeptides according to SEQ ID NO 2, 4, 6, 8, 10, 12, 14, 16, 18, 20, 22 50, 51, 52, 53 or 60. The criterions for determining homology between two peptide sequences are well established. For this purpose programs as BLASTP can be used. A deletion is still considered to be essentially the same if it involves 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 55, 56, 57, 58 or 61 more or less nucleotides as the respective deletion in SEQ ID NO 1, 3, 5, 7, 9, 11, 13, 15, 17, 19, or 21, which are also depicted in FIGS. 1 and 2.

A further aspect of the present invention is an EPO variant encoding polynucleotide selected from the group consisting of:

(a) polynucleotides encoding an EPO variant polypeptide, which comprises the N-terminal part of full length EPO including helix A and which lacks at least one of the following:
  (i) a fragment of at least 10 amino acids, preferably 11, 12, 13, 14, 15, 16, 17, 18, 19 or 20 amino acids between helix A and helix B;
  (ii) a fragment of at least 10 amino acids, preferably 11, 12, 13, 14, 15, 16, 17, 18, 19, 20, 21, 22, 23, 24, 25, 26, 27 or 28 amino acids of helix B;
  (iii) a fragment of at least 2 amino acids, preferably 3, 4, 5, or 6 amino acids between helix B and helix C;
  (iv) a fragment of at least 10 amino acids, preferably 11, 12, 13, 14, 15, 16, 17, 18, 19, 20, 21, 22, or 23 amino acids of helix C;
  (v) a fragment of at least 10 amino acids, preferably 11, 12, 13, 14, 15, 16, 17, 18, 19, 20, 21, 22, 23, 24, 25, 26, or 27 amino acids between helix C and 13; and/or
  (vi) a fragment of at least 10 amino acids, preferably 11, 12, 13, 14, 15, 16, 17, 18, 19, 20, 21, or 22 of helix 13;
  wherein said variant has cell protective and in particular neuroprotective activity but essentially no hematopoietic activity.
(b) polynucleotides encoding a derivative of a polypeptide encoded by a polynucleotide of any one of (a), wherein in said derivative between 1 and 10 amino acid residues are conservatively substituted compared to said polypeptide, and said derivative has cell protective and in particular neuroprotective activity but essentially no hematopoietic activity;
(c) polynucleotides the complementary strand of which hybridizes under stringent conditions to a polynucleotide as defined in any one of (a) to (b) and which code for a polypeptide having cell protective and in particular neuroprotective activity but essentially no hematopoietic activity;
or the complementary strand of such a polynucleotide.

In this context helix A, B, C, and D of the EPO polypeptide are regions homologous to the respective helix A, B, C, and D regions of full length EPO from mouse and human as outlined in FIG. 4. It is well known in the art how to determine homologies between two polypeptide sequences and someone of skill in the art will be capable to align a given EPO polypeptide sequence derived, e.g. from another species, and to determine the respective position of helix A, B, C, and D in this EPO polypeptide. It is preferred that the EPO variant polynucleotide is derived from a higher eukaryote, in particular a mammal or bird. Preferred mammals are humans, non-human primates; rodents, e.g. rat, or guinea pig; ruminant, e.g. cow; or sheep; horse; pig; rabbit; dog; or cat. A larger number of such full length EPO encoding polynucleotides from various species are known, including without limitation cat (Gene Bank Acc. L10606), pig (Gene Bank Acc. 10607), sheep (Gene Bank Acc. L0610), dog (Gene Bank Acc. L13027), macaque (Gene Bank Acc. M18189), rhesus monkey (Gene Bank Acc. L10609), mouse (Gene Bank Acc. 12930), rat (Gene Bank Acc. L10608), human (Gene Bank Acc. M11319) Bos taurus (Gene Bank Acc. U44762) and Bos indicus (Gene Bank Acc. 141354).

Preferably the polynucleotides encoding an EPO variant polypeptide lacks the following: (i); (ii); (iii); (iv); (v); (vi); (i) and (ii); (i) and (iii); (i) and (iv); (i) and (v); (i) and (vi); (ii) and (iii); (ii) and (iv); (ii) and (v); (ii) and (vi); (iii) and (iv); (iii) and (v); (iii) and (vi); (iv) and (v); (iv) and (vi); (v) and (vi); (i), (ii) and (iii); (i), (ii) and (iv); (i), (ii) and (v); (i), (ii), (vi); (i), (iii) and (iv); (i), (iii) and (v); (iii) and (vi); (i), (iv) and (v); (i), (iv) and (vi); (i), (v) and (vi); (ii), (iii) and (iv); (ii), (iii) and (v); (ii), (iii) and (vi); (ii), (iv) and (v); (ii), (iv) and (vi); (ii), (v) and (vi); (iii), (iv) and (v); (iii), (iv) and (vi); (iii), (v) and (vi); or (iv), (v) and (vi).

A polypeptide that exhibits cell protective activity is a polypeptide that has at least 50% (e.g., at least: 55%; 60%; 65%; 70%; 75%; 80%; 85%; 90%; 95%; 98%; 99%; 99.5%; or 100% or even more) of the ability of the respective EPO variant to protect neurons from damage by apoptosis, wherein the apoptosis is induced by oxygen or glucose deprivation, by chemical or radiation exposure or by viral or bacterial infection. Assays to determine damage to cells, in particular to neuronal cells are known in the art. A suitable assays is the oxygen glucose deprivation assay described herein below. In the described assay the readout is the amount of lactate dehydrogenase activity (LDH). However, a variety of other methods exist, which allow assessing the damage induced in a cell and in particular the amount of cell death (e.g. apoptosis, necoris). These assays include without limitation Tunnel assays, MTT-assay, life/death assay by staining (e.g. Ethidium bromide and acridine orange staining), caspase assay, electron microscopy, DNA-laddering, which are all well known in the art.

Am EPO variant polypeptide that exhibits essentially no hematopoietic activity is a polypeptide, which elicits in art known colony formation assays, an example of which is described below, at the same molar concentration as the rhEPO and wt mEPO, respectively, less than 10% of the CFU-E (Colony forming unit-erythroblast), preferably less than 9%, 8%, 7%, 6%, 5%, 4%, 3%, 2%, or 1%. The respective CFU-E numbers are calculated for a given rhEPO, wt mEPO or EPO variant by subtracting from each value the number of CFU-E observed in a control reaction (without wt or EPO variant).

In the context of the polypeptides of the present invention the term "junction" refers to the site wherein two amino acids follow each other which are not consecutive in the rhEPO or mouse wt EPO and which are potentially the result of splice events or other rearrangements in the EPO mRNA. The respective junction of the EPO variants of the present invention can be derived from FIG. 4, e.g. is ENIT|VGQQ for hS3 (SEQ ID NO: 64), VGQQ|ALLV for h1-4 (SEQ ID NO: 65), VNFY|ALLV for h1-5 (SEQ ID NO: 66), KRME|PWEP for hS4 (SEQ ID NO: 67), ITVP|GPVG for h1-1 (SEQ ID NO: 68), LNEN|NHC for h2-1 (SEQ ID NO: 69), KRME|KELM (SEQ ID NO: 70) for mS, LLAN|FLRG (SEQ ID NO: 71) for mG3, DTFC|RRGD (SEQ ID NO: 72) for mG5, KVNF|LRGK (SEQ ID NO: 73) for m301 or LSEA|VHGR (SEQ ID NO: 74) for mK3.

The polynucleotide molecules of the invention can be synthesized in vitro (for example, by phosphoramidite-based synthesis) or can be obtained from a cell, such as the cell of a mammal.

The EPO variants termed mS, mG3, mG5, m301 and mK3 having the deduced amino acid sequence as shown in SEQ ID NOs 14, 16, 18, 20, and 22, respectively were isolated from mouse The mouse sequence is highly homologous to the human sequence. An alignment of the amino acid sequences of EPO derived from humans and mouse is provided in FIG. 4. As is apparent the mouse sequence is distinguished from the human sequence by the lack of an alanine residue at position 8 and by the following 39 substitutions (the numbering is according to the respective amino acid position in the human EPO, the first amino acid indicated is the human amino acid at that position and the second is the corresponding mouse amino acid): $^4H \rightarrow ^4P$; $^6C \rightarrow ^6R$; $^9W \rightarrow ^9T$; $^{11}W \rightarrow ^{11}L$; $^{18}S \rightarrow ^{18}L$; $^{19}L \rightarrow ^{19}I$; $^{27}G \rightarrow ^{27}C$; $^{43}L \rightarrow ^{43}I$; $^{52}I \rightarrow ^{52}V$; $^{54}T \rightarrow ^{54}M$; $^{60}H \rightarrow ^{\alpha}G$; $^{61}C \rightarrow ^{61}P$; $^{62}S \rightarrow ^{62}R$; $^{64}S$; $^{84}G \rightarrow ^{84}E$; $^{85}Q \rightarrow ^{85}E$; $^{95}A \rightarrow ^{95}S$; $^{101}V \rightarrow ^{101}I$; $^{103}R \rightarrow ^{103}Q$; $^{104} \rightarrow G^{104}A$; $^{109}V \rightarrow ^{109}A$; $^{115}W \rightarrow ^{115}P$; $^{117}P \rightarrow ^{117}T$; $^{122}V \rightarrow ^{122}I$; $^{126}V \rightarrow ^{126}I$; $^{134}T \rightarrow ^{134}S$; $^{138}A \rightarrow ^{138}V$; $^{145}A \rightarrow ^{145}L$; $^{146}I \rightarrow ^{146}M$; $^{151}A \rightarrow ^{151}T$; $^{152}A \rightarrow ^{152}T$; $^{153}S \rightarrow ^{153}P$; $^{154}A \rightarrow ^{154}P$; $^{160}I \rightarrow ^{160}L$; $^{162}A \rightarrow ^{162}V$; $^{166}R \rightarrow ^{166}C$; $^{173}S \rightarrow ^{173}A$; $^{187}A \rightarrow ^{187}V$ and $^{190}T \rightarrow ^{190}R$. A humanized mS, mG3, mG5, m301 or mK3 carries the additional alanine residue at position 8 and/or at one or more preferably 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or 37 positions the human rather than the mouse amino acid sequence. It is particularly preferred that mS, mG3, m05, m301 and mK3 are fully humanized, i.e. that every amino acid at the above outlined positions, in as far as they are present in the respective variant, is of the human sequence rather than the mouse sequence. It is expected that the humanization of the mouse variants will diminish any immunological problems, which might be encountered when using in the treatment of humans.

The EPO variant nucleic acid molecules of the invention can be DNA, cDNA, genomic DNA, synthetic DNA, or, RNA, and can be double-stranded or single-stranded, the sense and/or an antisense strand. These molecules can be produced by, for example, polymerase chain reaction (PCR) or generated by treatment with one or more restriction endonucleases. A ribonucleic acid (RNA) molecule can be produced by in vitro transcription.

The polynucleotide molecules of the invention can contain naturally occurring sequences, or sequences that differ from those that occur naturally, but, due to the degeneracy of the genetic code, encode the same polypeptide, i.e. the polypeptides with SEQ ID NOs: 2, 4, 6, 8, 10, 12, 14, 16, 18, 20, and 22. In addition, these nucleic acid molecules are not limited to coding sequences, e.g., they can include some or all of the non-coding sequences that lie upstream or downstream from a coding sequence.

In addition, the isolated nucleic acid molecules of the invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In preferred embodiments the polynucleotides of the present invention also comprise nucleic acid molecules which are at least 50%, preferably 55%, 60%, 65%, 70%, 75%, 80%, 85°/a, 86%, 87%, 88%, 89%, 90%, 91%, 92%, 93%, 94%, 95%, 96%, 97%, 98%, or 99% identical to: (a) a nucleic acid molecule that encodes the polypeptide of SEQ ID NO: 2, 4, 6, 8, 10, 12, 14, 16, 18, 20, 22, 50, 51, 52, 53 or 60 and (b) the nucleotide sequence of SEQ ID NO: 1, 3, 5, 7, 9, 11, 13, 15, 17, 19, 21, 55, 56, 57, 58 or 61 respectively and which at the same time cell protective and in particular neuroprotective activity but essentially no hematopoietic activity The determination of percent identity between two sequences is accomplished using the mathematical algorithm of Karlin and Altschul (1993) *Proc. Natl. Acad. Sci. USA* 90: 5873-5877. Such an algorithm is incorporated into the BLASTN and BLASTP programs of Altschul et al. (1990) Mol. Biol. 215: 403-410. BLAST nucleotide searches are performed with the BLASTN program, score=100, word length=12, to obtain nucleotide sequences homologous to the EPO variant polypeptide encoding nucleic acids. BLAST protein searches are performed with the BLASTP program, score=50, wordlength=3, to obtain amino acid sequences homologous to the EPO variant polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding any of the EPO variants disclosed herein, or a derivative or fragment thereof, can be used as a hybridization probe according to standard hybridization techniques. The hybridization of an EPO variant probe to DNA or RNA from a test source (e.g., a mammalian cell) is an indication of the presence of the relevant EPO DNA or RNA in the test source. Hybridization conditions are known to those skilled in the art and can be found in Current Protocols in Molecular Biology, John Wiley & Sons, N.Y., 63.1-6.3.6, 1991. Stringent conditions are defined as equivalent to hybridization in 6× sodium chloride/sodium citrate (SSC) at 45° C., followed by a wash in 0.2×SSC, 0.1% SDS at 65° C. When selecting a probe specific for a variant carrying an internal deletion it is preferred that the probe used to detect homologous nucleic acids overlaps the boundaries of the deletion, e.g. hs3, h1-4, h1-5, hS4, mS, mG3, mG5 or m301. In cases where the splicing leads to an alternate C-terminus of the protein, e.g. h1-1, h2-1 or mK3 it is preferred that the probe used to detect homologous DNA sequences overlaps the boundaries between the known EPO sequence and the alternate C-terminus. For example, a probe could be designed, which comprises 10 complementary bases 5' of the splice site and 10 complementary bases 3' of the splice site.

An "isolated DNA" is either (1) a DNA that contains sequence not identical to that of any naturally occurring sequence, or (2), in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

A further aspect of the present invention is a vector containing the polynucleotide(s) of the present invention or a protein encoded by a polynucleotide of the present invention The term "vector" refers to a protein or a polynucleotide or a mixture thereof which is capable of being introduced or of introducing the proteins and/or nucleic acid comprised into a cell. It is preferred that the proteins encoded by the introduced polynucleotide are expressed within the cell upon introduction of the vector.

In a preferred embodiment the vector of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox, viruses, lentivirus (Chang, L. J. and Gay, E. B. (20001) Curr. Gene Therap. 1:237-251), herpes viruses, in particular Herpes simplex virus (HSV-1, Carlezon, W. A. et al. (2000) Crit. Rev. Neurobiol.), baculovirus, retrovirus, adeno-associated-virus (AAV, Carter, P. J. and Samulski, R. J. (2000) J. Mol. Med. 6:17-27), rhinovirus, human immune deficiency virus (HIV), filovirus and engineered versions thereof (see, for example, Cobinger G. P. et al (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3:466-76 and Springer et al. (1998) Mol. Cell. 2:549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1,2-Dioleyloxypropyl-3-trimethylammoniumbromid) and DPOE (Dioleoylphosphatidyl-ethanolamin) which both have been used on a variety of cell lines.

Nucleic acid coated particles are another means for the introduction of nucleic acids into cells using so called "gene guns", which allow the mechanical introduction of particles into the cells. Preferably the particles itself are inert, and therefore, are in a preferred embodiment made out of gold spheres.

In a further aspect the polynucleotide of the present invention is operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g., promoters for the snRNA U6 or scRNA 7SK gene, the cytomegalovirus hCMV immediate early gene, the early or late promoters of SV40 adenovirus, viral promoter and activator sequences derived from, e.g., NBV, HCV, HSV, HPV, EBV, HTLV, MMTV or HIV; which allow inducible expression like, for example, CUP-1 promoter, the tet-repressor as employed, for example, in the tet-on or tet-off systems, the lac system, the trp system; regulatory elements directing tissue specific expression, preferably nerve cell specific expression, e.g. promoter (e.g. Thy-1.2, NSE, myosin light chain II, tyrosine hydroxylase, CaMKIIalpha promoter; platelet-derived growth factor beta-chain (PDGF), dopamine beta-hydroxylase, Tau, regulatory elements (e.g. NRSE/RE-1; neuron-restrictive silencing element/repressor element 1) directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

As used herein, "operatively linked" means incorporated into a genetic construct so that expression control sequences effectively control expression of a coding sequence of interest.

Similarly, the polynucleotides of the present invention can form part of a hybrid gene encoding additional polypeptide sequences, for example, a sequence which encodes a protein that functions as a marker or reporter. The hybrid gene can lead to a fusion protein or the two or more parts can be separated by internal ribosomal entry sites (IRES) sequence, which lead to the expression of two or more separate proteins. Examples of marker and reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), green fluorescent protein (GFP) and variants thereof and xanthine guanine phosphoribosyltransferase (XGPRT). As with many of the standard procedures associated with the practice of the invention, skilled artisans will be aware of additional useful reagents, for example, additional sequences that can serve the function of a marker or reporter. If the expression of the hybrid gene leads to one polypeptide the hybrid polypeptide will usually include a first portion and a second portion; the first portion being a EPO variant polypeptide and the second portion being, for example, the reporter described above or an Ig constant region or part of an Ig constant region, e.g., the CH2 and CH3 domains of IgG2a heavy chain. Other hybrids could include a heterologous peptide sequence to facilitate purification and/or detection, e.g. an antigenic tag like, for example, a myc tag, or a tag with preferential binding to a region, e.g. chitin tag or His tag. Recombinant nucleic acid molecules can also contain a polynucleotide sequence encoding a EPO variant polypeptide operatively linked to a heterologous signal sequence. Such signal sequences can direct the protein to different compartments within the cell and are well known to someone of skill in the art. A preferred signal sequence is a sequence that facilitates secretion of the resulting protein. Preferably these signal and/or taq sequences are designed in such that they can be cleaved of the EPO variant after purification to provide an essentially pure protein without two many amino acids, preferably not more than 10 additional amino acids to the final EPO. Such cleavage sites are well known in the art and comprise, e.g endopeptidase cleavage sites and intein cleavage sites.

Another aspect of the present invention is a host cell genetically engineered with the polynucleotide or the vector as outlined above. The host cells that may be used for purposes of the invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 of Hi5 cells, which can be infected with, for example, recombinant virus expression vectors (for example, baculovirus) containing the polynucleotide molecules of the invention; *Xenopus oocytes*, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a EPO variant nucleotide sequence; or mammalian cell systems (for example, COS, CHO, BHK, HEK293, VERO, HeLa, MDCK, Wi38, Swiss 3T3 and NIH 3T3 cells), which can be transformed with recombinant expression constructs containing, for example, promoters derived, for example, from the genome of mammalian cells (for example, the metallothionein promoter) from mammalian viruses (for example, the adenovirus late promoter, CMV IE and the vaccinia virus 7.5K promoter) or from bacterial cells (for example, the tet-repressor binding is employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

Since EPO is heavily glycosylated in vivo it is desirable to chose an expression system, which provides faithful glycosylation of the protein. Consequently, it is preferred to introduce the polynucleotides encoding the EPO slice variants of the present invention into higher eukaryotic cells, in particular into mammalian cells, e.g. COS, CHO, BHK, HEK293, VERO, HeLa, MDCK, Wi38, Swiss 3T3 or NIH 3T3 cells.

A further aspect of the present invention is a transgenic non-human animal containing a polynucleotide, a vector and/or a host cell as described above. The animal can be a mosaic animal, which means that only part of the cells making up the body comprise polynucleotides, vectors, and/or cells of the present invention or the animal can be a transgenic animal which means that all cells of the animal comprise the polynucleotides and/or vectors of the present invention or are derived from a cell of the present invention. Mosaic or transgenic animals can be either homo- or heterozygous with respect to the polynucleotides of the present invention contained in the cell. In a preferred embodiment the transgenic animals are either homo- or heterozygous knock-out or knock-in animals with respect to the genes which code for the proteins of the present invention. The animals can in principal be any animal, preferably, however, it is a mammal, selected from the group of non-human primate horse, bovine, sheep, goat, pig, dog, cat, goat, rabbit, mouse, rat, guinea pig, hamster, or gerbil.

Another aspect of the present invention is a process for producing an EPO variant polypeptide encoded by a polynucleotide of the present invention comprising: culturing the host cell described above and recovering the polypeptide encoded by said polynucleotide. Preferred combinations of host cells and vectors are outlined above and further combination will be readily apparent to someone of skill in the art. Depending on the intended later use of the recovered peptide a suitable cell type can be chosen. As outlined above eukaryotic cells are preferably chosen, if it is desired that the proteins produced by the cells exhibit an essentially natural pattern of glycosylation and prokaryotic cells are chosen, if, for example, glycosylation or other modifications, which are normally introduced into proteins only in eukaryotic cells, are not desired or not needed.

It is known in the prior art that the pharmacokinetic of protein drugs can be significantly altered by modification of the protein. For full length EPO it has been described that glycosylation, in particular the presence of sialic acid residues at the end of the oligosaccharide side chains attributes to the circulation time (WO 95/05465) and that removal of sialic acid groups exposes galactose residues, which increases clearance by the liver. Therefore, one approach taken to enhance EPO circulation time was the increase in sialic acid residues. Several approaches, thus, involve the provision of additional glycosylation sites (see e.g. WO 91/05867, WO 94/09257 and WO 01/81405. Such modified EPO analogs may have at least one additional N-linked and/or O-linked carbohydrate chain. Other attempts to improve the half life of EPO involved the addition of polyethylene glycol residues (PEG) of varying length the amino acid backbone (see e.g. WO 00/32772, WO 01/02017, WO 03/029291. Another attempt used the modification of EPO molecules with at least one N-linked and/or O-linked oligosaccharide which were further modified with oxidation, sulfation, phosphorylation PEGylation or a combination thereof (see WO 2005/025606). All these approaches can equally be employed to extend the half life of the EPO variants of the present invention and accordingly in a preferred embodiment above process further comprising the step of modifying the EPO variant, wherein the modification is selected from the group consisting of oxidation, sulfation, phosphorylation, addition of oligosaccharides or combinations thereof. If the addition of further N-linked or O-linked oligonucleotides is desired it is possible to introduce them by introducing additional glycosylation sites as has been described in the prior art, e.g. at positions 30, 51, 57, 69, 88, 89, 136 and/or 138, if the respective position is present in the variant of the present invention (see WO 01/81405).

A further aspect of the invention is a process for producing cells capable of expressing at least one of the EPO variants comprising genetically engineering cells in vitro with the vector of claim 3 or 4, wherein said EPO variant polypeptide(s) is(are) encoded by a polynucleotide of the present invention.

Another aspect of the invention is a polypeptide having the amino acid sequence encoded by a polynucleotide of the invention or obtainable by the process mentioned above. The polypeptides of the invention include all those disclosed herein and fragments of these polypeptides, which carry between 1 and 10 N- and/or C-terminal deletions. Preferably, the deletions are less than 10, less than 9, less than 8, less than 7, less than 8, less than 7, less than 6, less than 5, less than 4, less than 3, less than 2, less than 1 amino acids. The polypeptides embraced by the invention also include fusion proteins that contain either the EPO slice variant as indicated in SEQ ID Nos 2, 4, 6, 8, 10, 12, 14, 16, 18, 20 and 22 or humanized version of 14, 16, 18, 20 and 22 or a fragment thereof as defined above fused to an unrelated amino acid sequence. The unrelated sequences can comprise additional functional domains or signal peptides. Signal peptides are described in greater detail and exemplified below.

The polypeptides can be any of those described above but with not more than 10 (e.g., not more than: 10, nine, eight, seven, six, five, four, three, two, or one) conservative substitutions. Conservative substitutions are known in the art and typically include substitution of, e.g. one polar amino acid with another polar amino acid and one acidic amino acid with another acidic amino acid. Accordingly, conservative substitutions preferably include substitutions within the following groups of amino acids: glycine, alanine, valine, proline, isoleucine, and leucine (non polar, aliphatic side chain); aspartic acid and glutamic acid (negatively charged side chain); asparagine, glutamine, methionine, cysteine, serine and threonine (polar uncharged side chain); lysine, histidine and arginine; and phenylalanine, tryptophane and tyrosine (aromatic side chain); and lysine, arginine an histidine (positively charged side chain). It is well known in the art how to determine the effect of a given substitution, e.g., on $pK_1$ etc. All that is required of a polypeptide having one or more conservative substitutions is that it has at least 50% (e.g., at least: 55%; 60%; 65%, 70%; 75%; 80%; 85%; 90%; 95%; 98%; 99%; 99.5%; or 100% or more) of the ability of the unaltered EPO variant to protect neurons from damage/cell death (e.g. by apoptosis or necrosis), wherein the cell death is induced by oxygen and/or glucose deprivation, by toxic, chemical, physical, mechanical, inflammatory or radiation exposure or by viral or bacterial infection.

Both polypeptides and peptides can be produced by standard in vitro recombinant DNA techniques and in vivo transgenesis, using nucleotide sequences encoding the appropriate polypeptides or peptides. Methods well-known to those skilled in the art can be used to construct expression vectors containing relevant coding sequences and appropriate transcriptional/translational control signals. See, for example, the techniques described in Sambrook et al., *Molecular Cloning: A Laboratory Manual* (2nd Ed.) [Cold Spring Harbor Laboratory, N.Y., 1989], and Ausubel et al., *Current Protocols in Molecular Biology* [Green Publishing Associates and Wiley Interscience, N.Y., 1989].

Polypeptides and fragments of the invention also include those described above, but modified for in vivo use by the addition, at the amino- and/or carboxyl-terminal ends, of blocking agents to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

The term "isolated" polypeptide or peptide fragment as used herein refers to a polypeptide or a peptide fragment which either has no naturally-occurring counterpart or has been separated or purified from components which naturally accompany it, e.g., in tissues such as tongue, pancreas, liver, spleen, ovary, testis, muscle, joint tissue, neural tissue, gastrointestinal tissue or tumor tissue, or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide is "isolated."

An isolated polypeptide (or peptide fragment) of the invention can be obtained, for example, by extraction from a natural source (e.g., from tissues or bodily fluids); by expression of a recombinant nucleic acid encoding the polypeptide; or by chemical synthesis. A polypeptide that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

A further aspect of the invention is an antibody, which specifically binds to the EPO variant polypeptide encoded by polynucleotides of the invention or obtainable by the process mentioned above. The term "antibody" comprises monoclonal and polyclonal antibodies and binding fragments thereof, in particular Fe-fragments as well as so called "single-chain-antibodies" (Bird R. E. et al (1988) Science 242:423-6), chimeric, humanized, in particular CDR-grafted antibodies, and dia or tetrabodies (Holliger P. et al (1993) Proc. Natl. Acad. Sci. U.S.A. 90:6444-8). Also comprised are immunoglobulin like proteins that are selected through techniques including, for example, phage display to specifically bind to the polypeptides of the present invention. In this context the term "specific binding" refers to antibodies raised against peptides derived from splice junctions or junctions created by other processes, e.g. ENIT|VGQQ for hS3 (SEQ ID NO: 64), VGQQ|ALLV for h1-4 (SEQ ID NO: 65), VNFY|ALLV of h1-5 (SEQ ID NO: 66), KRME|PWEP of hS4 (SEQ ID NO: 67), ITVP|GPVG of h1-1 (SEQ ID NO: 68), LNEN|NHC of h2-1 (SEQ ID NO: 69), KRME-|KELM (SEQ ID NO: 70) of mS, LLAN|FLRG (SEQ ID NO: 71) of mG3, DTFC|RRGD (SEQ ID NO: 72) of mG5, KVNF|LRGK (SEQ ID NO: 73) of m301 or LSEA|VHGR (SEQ ID NO: 74) of mK3. Such peptides can comprise additional or less N- or C-terminal amino acids. An antibody is considered to be specific to the EPO variant, if its affinity towards the variant it at leak 50-fold higher, preferably 100-fold higher, more preferably at least 1000-fold higher than towards the full length human or murine EPO. Preferably specific antibodies of the present invention do not or essentially do not bind to full length human or murine EPO. It is well known in the art how to make antibodies and to select antibodies with a given specificity.

A further aspect of the present invention concerns the use of a polynucleotide, a vector, a host cell or, a polypeptide of the present invention for the manufacture of a medicament for the treatment or prevention of a condition associated with tissue damage due to cell death (e.g. apoptosis and necrosis). The apoptosis or necrosis leads to the cell destruction, which can be prevented or ameliorated when using the polynucleotide, vector, host cell or polypeptide of the present invention. Cell death can be induced by many different internal and external stimuli and include preferably ischemic, hypoxia, bacterial or viral infection, radiation, or induced by metabolic, toxic, chemical, autoimmunologic, or traumatic stimuli. It is well known in the art how to detect cell death like, for example, using morphological criteria, a TUNNEL assay, MIT-assay, life/death assay by staining (e.g. Ethidium bromide and acridine orange staining), caspase assay, electron microscopy, DNA-laddering or the LDH release assay described below. For example, apoptosis is characterized by chromatin fragmentation, extravasation of cellular contents and eventually death of the cell. It has been recognized to play a role in many acute or chronic pathologic processes. Accordingly, a preferred use of the present invention comprises the administration of polynucleotides, vectors, host cells or polypeptides of the present invention to prevent, treat or ameliorate acute and chronic neurodegenerative or neuroinflammatory disorders, acute or chronic disorder of the heart (e.g. myocardial infarction), lung (e.g. asthma, chronic obstructive lung disease), kidney (e.g. glomerulonephritis), liver (e.g. chronic liver failure) or pancreas (e.g. pancreatitis), as well as conditions associated with cell (e.g. stem cell) or organ transplantation (e.g. kidney or liver). In this respect is also envisioned that the EPO variants of the present invention can be included in storage solutions used for storing organs or limbs for transport and/or after traumatic injury.

Acute neurodegenerative disorders include, but are not limited to, various types of acute neurodegenerative disorders associated with neuronal cell death including cerebrovascular insufficiency, focal or diffuse brain trauma, diffuse brain damage, and spinal cord injury. Examples of acute neurodegenerative disorders are: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), whiplash shaken infant syndrome infectious encephalitis (e.g. herpes encephalitis), meningitis (e.g. bacterial), headache (e.g. migraine).

Chronic neurodegenerative disorders that can be treated with the EPO variants of the present invention include, but are not limited to, dementias (e.g. Alzheimer's disease, vascular dementias), Pick's disease, diffuse Lewy body disease, progressive supranuclear palsy (Steel-Richardson syndrome), multiple sclerosis, multiple system atrophy (including Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, spastic paraparesis, progressive multifocal leukoencephalopathy, familial dysautonomia (Riley-Day syndrome), and priori diseases (including, but not limited to Creutzfeldt-Jakob, Gerstmann-Strussier-Scheitiker disease, Kuru and fatal familial insomnia), polyneuropathies (e.g. diabetic, alcohol-toxic, Guillain-Barré-Syndrome, chronic inflammatory demyelinating polyneuropathy), prion diseases, addiction, affective disorders (e.g. depression), schizophrenic disorders, chronic fatigue syndrome, chronic pain (e.g. lower back pain).

A further aspect of the present invention concerns the use of a polynucleotide, a vector, a host cell or a polypeptide of the present invention for the manufacture of an anti-aging medication. The basis for this application of the EPO variants of the present invention is the fact that the progressing deterioration of most bodily functions, which accompanies aging has been associated with cell death and it is, therefore, envisioned that the EPO variants of the present invention, which only provide the beneficial cell protective effect can be taken continuously without suffering the side effects usually associated with the continuos administration of EPO, which, however, can be attributed to the erythropoietic effect of EPO.

The inventors have astonishingly found that the nucleic acids and proteins according to the invention possess astonishing anti-inflammatory properties (see figures and experiments). Thus, these EPO variants are useful in treatment of inflammatory and degenerative diseases. Inflammatory diseases are diseases such as but not limited to multiple sclerosis, viral and bacterial infections or sepsis. Degenerative diseases are diseases such as but not limited to stroke, myocardial infarctions.

The invention also relates to all kinds of forms of in vivo expression of the nucleic acids according to the invention. It further relates to transformed cells, in particular stem cells which are used as therapeutic agents. Such cells may be stably transformed with a nucleic acid according to the invention. The nucleic acid may in a cassette where it is operably linked to a promoter. The promoter may capable of driving the expression only in particular tissues, such as but not limited to neuronal tissue or the brain or tissue which exhibits inflammation or degeneration. Respective teaching may be taken from WO 97/14307.

The activity (in units) of EPO polypeptide is traditionally defined based on its effectiveness in stimulating red cell production in rodent models (and as derived by international standards of EPO). One unit (U) of regular EPO (MW of about 34,000) is about 10 ng of protein (1 mg protein is approximately 100,000 U). However, as mentioned the invention involves the use of non-hematopoietic forms of erythropoietin, and as such, this definition based on hematopoietic activity is inappropriate. Thus, as used herein, the activity unit of EPO variant is defined as the amount of protein required to elicit the same activity in neural or other erythropoietin-responsive cellular systems as is elicited by native EPO in the same system. The skilled artisan will readily determine the units of a non-hematopoietic EPO following the guidance herein.

In a further aspect the present invention provides a pharmaceutical composition comprising a polynucleotide, a vector, a host cell, a polypeptide and/or an antibody of the present invention and a one or more pharmaceutically acceptable carrier.

In the practice of one aspect of the present invention, a pharmaceutical composition as described above may be administered to a mammal by any route which provides a sufficient level of an erythropoietin variant. It can be administered systemically or locally. Such administration may be parenterally, transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated. In cases of treating the nervous system this administration route includes, but is not limited to, the intracerebral, intraventricular, intracerebroventricular, intrathecal, intracistemal, intraspinal and/or peri-spinal routes of administration, which can employ intracranial and intravertebral needles, and catheters with or without pump devices.

In a preferred embodiment of pharmaceutical composition comprises an EPO variant polypeptide in a dosage unit form adapted for protection or enhancement of EPO-responsive cells, tissues or organs which comprises, per dosage unit, an effective non-toxic amount within the range from about 0.5 mg to 5 mg of EPO variants; 0.6 mg to 5 mg of EPO variants; 0.7 mg to 5 mg of EPO variants; 0.8 mg to 5 mg of EPO variants; 0.9 mg to 5 mg of EPO variants; 1 to 5 mg of EPO variants; 1.5 to 5 mg of EPO variants; 2 to 5 mg of EPO variants; 2.5 to 5 mg of EPO variants; 3.5 to 5 mg of EPO variants; 4 mg to 5 mg of EPO variants; or 4.5 to 5 mg of EPO variants and a pharmaceutically acceptable carrier.

In a preferred embodiment, an EPO variant polypeptide may be administered systemically at a dosage between 100 nanograms to about 50 micrograms per kg body weight, preferably about 20 micrograms to about 50 micrograms per kg-body weight. Such serum levels may be achieved at about 1, 2, 3, 4, 5, 6, 7, 8, 9, or 10 hours post-administration. Such dosages may be repeated as necessary. For example, administration may be repeated daily, or every other, third, fourth, fifth, sixth, or seventh day, as long as clinically necessary, or after an appropriate interval, e.g., every 1 to 12 weeks, preferably, every 3 to 8 weeks in one embodiment, the effective amount of EPO variant and a pharmaceutically acceptable carrier may be packaged in a single dose vial or other container. Depending on the respectively treated disease or condition the EPO variant can be administered in a single dose, for a predetermined period of time or continuously. When an acute condition or disease is treated it might be sufficient to provide the patient with a single dose of EPO variant or for a period of, e.g. for 2 days to 12 months, preferably 1 week to 6 months, more preferably 2 weeks to 3 months. If a chronic disease or condition is treated or if the EPO variant is used to prevent or reduce the deterioration associated with aging the EPO variant can be administered continuously. If the EPO variant of the present invention is administered for a given time period or continuously it is preferably administered in the intervals and preferred intervals indicated above. The intervals necessary will depend in part on the serum level of the EPO variant necessary to treat or ameliorate the respective disease and on the pharmacokinetic of the respective EPO variant, which will in part depend on modifications of EPO by, for example, PEG. It will be in the discretion of the practitioner to determine the exact duration, dose and type of EPO variant taking into consideration, e.g. the condition of the patient to be treated, the severity of the condition etc.

For other routes of administration, such as by use of a perfusate, injection into an organ, or other local administration, a pharmaceutical composition will be provided which results in similar levels of an EPO variant as described above. A level of about 10 pg/ml to about 1000 ng/ml is desired.

The pharmaceutical compositions of the invention may comprise a therapeutically effective amount of a compound, e.g. polynucleotide, polypeptide, cell or vector, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent, Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets. In one embodiment, an autoinjector comprising an injectable solution of an EPO variant may be provided for emergency use by ambulances, emergency rooms, and battlefield situations, and even for self-administration in a domestic setting, particularly where the possibility of traumatic amputation may occur, such as by imprudent use of a lawn mower. The likelihood that cells and tissues in a severed foot or toe will survive after reattachment may be increased by administering an EPO variant to multiple sites in the severed part as soon as practicable, even before the arrival of medical personnel on site, or arrival of the afflicted individual with severed toe in tow at the emergency room.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

Suppositories generally contain active ingredient in the range of 0.5% to 10% by weight; oral formulations preferably contain 10% to 95% active ingredient.

A perfusate composition may be provided for use in transplanted organ baths, for in situ perfusion, or for administration to the vasculature of an organ donor prior to organ harvesting Such pharmaceutical compositions may comprise levels of an EPO variant or a form of an EPO variant not suitable for acute or chronic, local or system administration to an individual, but will serve the functions intended herein in a cadaver, organ bath, organ perfusate, or in situ perfusate prior to removing or reducing the levels of the EPO variant contained therein before exposing or returning the treated organ or tissue to regular circulation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, EPO variant can be delivered in a controlled-release system. For example, the polypeptide may be administered using intravenous infusion, an implantable osmotic pump, a transdermal patch, liposomes, or other modes of administration. In one embodiment, a pump may be used (see Sefton (1987) *CRC Crit. Ref Biomed. Eng.* 14: 201; Buchwald et al. (1980) *Surgery* 88:507; Saudek et al, (1989) *N. Eng. J. Med.* 321: 574), In another embodiment, the compound can be delivered in a vesicle, in particular a liposome (see Langer (1990) *Science* 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et al. (1985) Science 228:190; During et al. (1989) *Ann. Neural.* 25: 351; Howard et al. (1989) *J. Neurosurg.* 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, *Science* 249: 1527-1533).

In another embodiment, EPO variant, as properly formulated, can be administered by nasal, oral, rectal, vaginal, or sublingual administration.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery; by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

In another aspect of the invention, a perfusate or perfusion solution is provided for perfusion and storage of organs for transplant, the perfusion solution including an amount of an pharmaceutic compositions effective to protect EPO variant-responsive cells and associated cells, tissues or organs.

Transplant includes but is not limited to xenotransplantation, where a organ (including cells, tissue or other bodily part) is harvested from one donor and transplanted into a different recipient; and autotransplant, where the organ is taken from one part of a body and replaced at another, including bench surgical procedures, in which an organ may be removed, and while ex vivo, resected, repaired, or otherwise manipulated, such as for tumor removal, and then returned to the original location. In one embodiment, the perfusion solution is the University of Wisconsin (UW) solution (U.S. Pat. No. 4,798,824) which contains from about 1 to about 25 U/ml erythropoietin, 5% hydroxyethyl starch (having a molecular weight of from about 200,000 to about 300,000 and substantially free of ethylene glycol, ethylene chlorohydrin, sodium chloride and acetone); 25 mM $KH_2PO_4$; 3 mM glutathione; 5 mM adenosine; 10 mM glucose; 10 mM HEPES buffer, 5 mM magnesium gluconate; 1.5 mM $CaCl_2$. 105 mM sodium gluconate; 200,000 units penicillin; 40 units insulin; 16 mg Dexamethasone; 12 mg Phenol Red; and has a pH of 7.4-7.5 and an osmolality of about 320 mOsm/l. The solution is used to maintain cadaveric kidneys and pancreases prior to transplant. Using the solution, preservation may be extended beyond the 30-hour limit recommended for cadaveric kidney preservation. This particular perfusate is merely illustrative of a number of such solutions that may be adapted for the present use by inclusion of an effective amount of the pharmaceutical composition. In a further embodiment, the perfusate solution contains the equivalent from about 5 to about 35 U/ml erythropoietin, or from about 10 to about 30 U/ml erythropoietin.

While the preferred recipient of an EPO variant for the purposes herein throughout is a human, the methods herein apply equally to other mammals, particularly domesticated animals, livestock, companion and zoo animals. However, the invention is not so limiting and the benefits may be applied to any mammal.

If a person is known to be at risk of developing a stroke a prophylactic administration of the pharmaceutical composition of the present invention is possible. In these cases the pharmaceutical compositions, in particular EPO variant polypeptide is preferably administered in above outlined preferred and particular preferred doses on a daily basis. Preferably, between 100 nanograms to about 50 micrograms per kg body weight, preferably about 20 micrograms to about 50 micrograms per kg-body weight. This administration can be continued until the risk of developing a stroke has lessened. In most instances, however, the pharmaceutical composition will be administered once a stroke has been diagnosed. In these cases it is preferred that a first dose of the pharmaceutical composition is administered for the first time within 24 hours after the first symptoms of a stroke are evident, preferably within 12, 11, 10, 9, 8, 7, 6, 5, 4, 3, 2, 1 hour or less. Preferably the administration is then continued for preferably at least 7, more preferably at least 14 and more preferably for at least 21 days. The doses are administered preferably once a day and preferably in above indicated doses.

BRIEF DESCRIPTION OF THE FIGURES AND DRAWINGS

FIG. 1: Comparison of EPO PCR products: Panel A depicts the DNA products of various PCR reactions performed with either pure plasmid comprising the different murine EPO variants or cDNA from mouse brain of kidney, which are separated on a 1.2% agarose gel. From the left to the right the lanes comprise: 1 kb molecular weight marker, the product of pure mK3, pure mG3, pure mG5, pure m301, pure mS, pure mWT, brain cDNA, kidney cDNA. Panel B depicts the DNA product of a PCR performed with cDNA from human brain. From the left to the right the lanes comprise 1 kb molecular weight standard and the PCR product of human brain cDNA.

FIG. 2: Alignment of nucleotide sequences of the EPO variants identified in murine brain cDNA (SEQ ID NOS 13, 15, 17, 19 and 21, respectively, in order of appearance) and "wild type" murine EPO (SEQ ID NO: 75), i.e. the sequence of the previously described EPO.

FIG. 3: Alignment of nucleotide sequences of the EPO variants identified in human brain cDNA (SEQ ID NOS 1, 3, 5, 7, 9 and 11, respectively, in order of appearance) and "wild type" human EPO (SEQ ID NO: 76).

FIG. 4: Alignment of the amino acid sequences of the EPO variants identified in mouse (SEQ ID NOS 14, 16, 18, 20 and 22, respectively, in order of appearance) and human (SEQ ID NOS 2, 4, 6, 8, 10 and 12, respectively, in order of appearance) with the respective "wild type" EPO ('hWT' disclosed as SEQ ID NO: 77 and 'mWT' disclosed as SEQ ID NO: 78).

FIG. 5: Hematopoietic activity of murine and human EPO and the EPO variants of the present invention. Panel A depicts the results of a colony forming assay for murine EPO and EPO variants and Panel B depicts the of a colony forming assay for human EPO and EPO variants.

Figure 6:
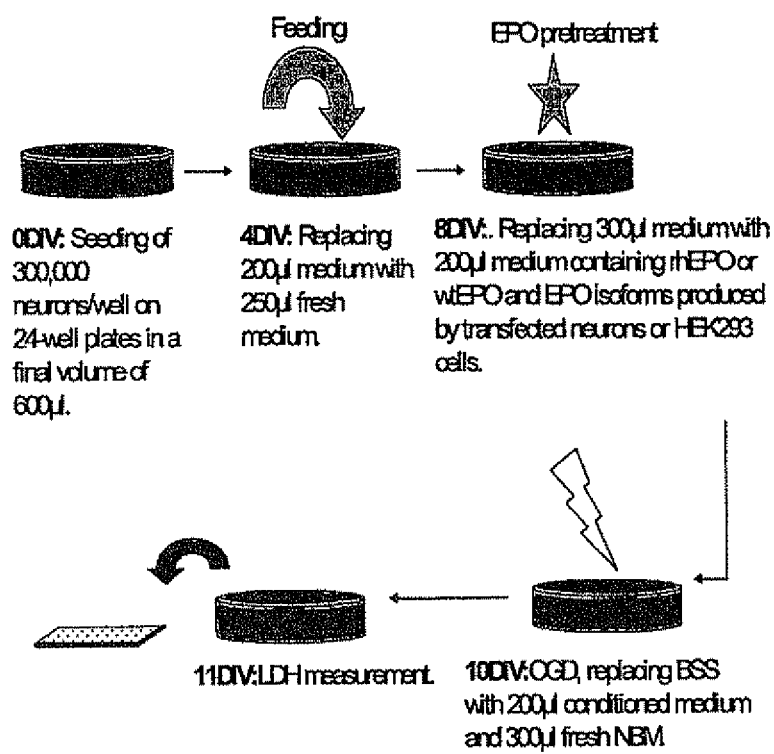

FIG. 6: Experimental setup for neuroprotection assays with rhEPO and EPO-isomers.

FIG. 7: Panel A shows an experiment with 1 h 40 min and 1 h 50 min oxygen glucose deprivation (OGD) length. At both time-points a protection rate of 40-50% for the neuroguardians, but no protection with mEPO and rhEPO was observed. Panel B shows an experiment with two different time-points (OGD length between two experiments varies according to density of neurons). At 2 h 45 min only weak protection is achieved with wtEPO (20-30%) compared to neuroguardians (60-70%). Full protection capacity of rh EPO is only observed at higher damage levels (3 h 15 min).

FIG. 8: Panel A shows an experiment with 2 h 00 min, 2 h 15 min and 2 h 20 min OGD length with a protein concentration equalling 100 U/l hEPO. At all three time-points a protection rate of 40-50% for the human, but no protection with mEPO and rhEPO. Panel B shows an experiment with two different time-points (OGD length between two experiments varies according to density of neurons). At 2 h 45 min only weak protection is achieved with wtEPO (20-30%) compared to neuroguardians (60-70%). Full protection capacity of EPO is only observed at higher damage levels (3 h 15 min).

FIG. 9: Panel A shows a Western Blot from medium of HEK293-cells transfected with peDNA3.1-V5/His-hEPO, pcDNA3.1-V5/His-hS3 or pcDNA3.1-V5/His-hS4, respectively. These media were used for experiments shown in FIG. 8. Concentration of hEPO, quantified by the mouse-EPO-ELISA (R&D) was 2 U/ml. rhEPO (=2.5 ng were loaded on the gel), hEPO (=0.4 ng were loaded on the gel), hS3 and hS4: each 20 medium (collected 2 days after transfection). Marker=5 µl BenchMark™ His-tagged Protein Standard (Invitrogen). Panel B shows a Western Blot of His-Tag-purified mouse wild type EPO (mEPO), human hS3 and hS4 EPO variants. mEPO was quantified with the EPO-mouse-ELISA. 130 pg mEPO were loaded onto the gel. (primary antibody: rabbit anti-rhEPO-Antikörper; Santa-Cruz).

Figure 10:
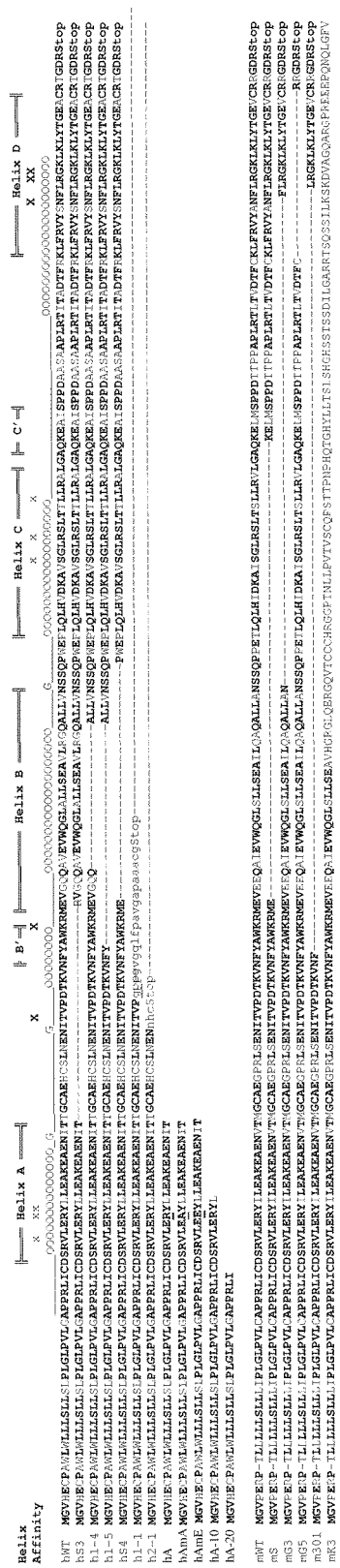

FIG. 10: Alignment of the amino acid sequences of the EPO variants created recombinantly (alpha-helix mutants) and identified in vivo. Herein residues 1-53 of SEQ ID NO 50 is the human alpha helix wild type sequence; SEQ ID NO 51 is hAmA (point mutation Alanin); SEQ ID NO 52 is hAmE (point mutation glutamic acid); SEQ ID NO 53 is hA-10 (deletion mutant) and SEQ ID NO 54 is hA-20 (deletion mutant). FIG. 10 also discloses 'hWT' as SEQ ID NO: 77, 'hS3' as SEQ. ID NO: 2, 'h1-4' as SEQ ID NO: 4, 'h1-5' as SEQ ID NO: 6, 'hS4' as SEQ ID NO: 8, 'h1-1' as SEQ ID NO: 10, 'h2-1' as SEQ ID NO: 12, 'mWT' as SEQ ID NO: 78, 'mS' as SEQ ID NO: 14, 'mG3' as SEQ ID NO: 16, 'mG5' as SEQ ID NO: 18, 'm301' as SEQ ID NO: 20 and 'mK3' as SEQ ID NO: 22.

Figure 11:
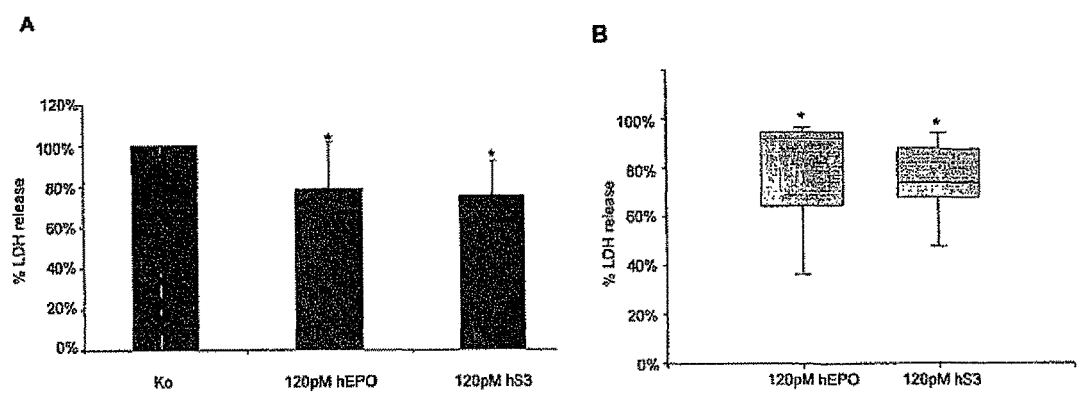

FIG. 11: hEPO and hS3 mediated cytoprotection in a model of ischemia consisting of serum deprivation and hypoxia in H9c2 cardiac myoblasts. H9c2 cells were incubated in serum-deprived DMEM-medium either in normoxic or hypoxic conditions for 24 h. Apoptosis was assessed 24 h later by LDH assay. Data were normalized by setting the delta LDH release of untreated cells in normoxic and hypoxic conditions to 100%. A: Column diagram representing the average values of normalized LDH release. B: Data were presented as box plot diagram showing the median (line across the box), the 25th percentile (lower hinge), the 75th percentile (upper hinge), the maximum and the minimum value. Number of experiments n=7. P*<0.001 (ANOVA1).

Figure 12:
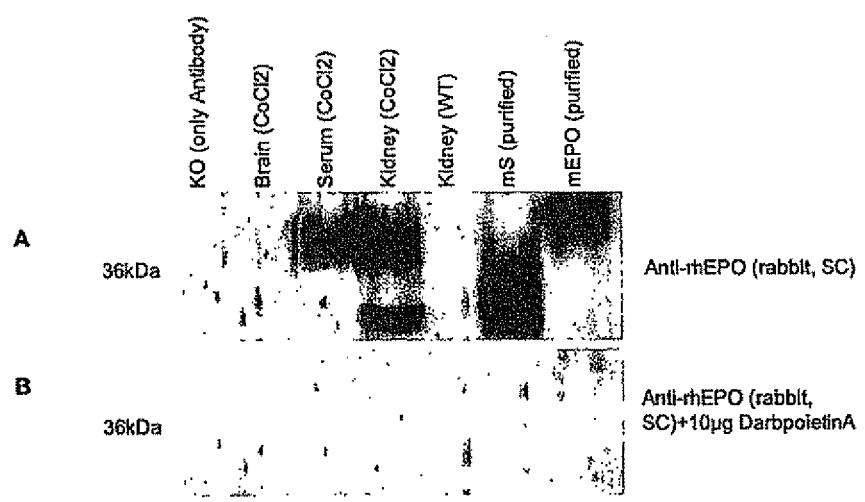

FIG. 12: Immunoprecipitation of EPO variants using an anti-mEPO antibody from R&D (goat, biotin-labelled); A: Detection of a second EPO isoform (30 kDa) in a kidney protein extract of CoCl2-treated mice (129S6). B: Blocking of the antibody-antigen interaction by DarbpoietinA.

Figure 13:
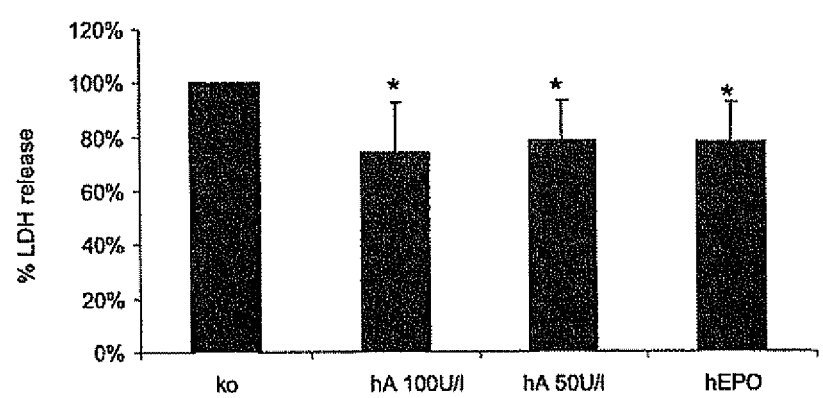

FIG. 13: Neuroprotection mediated by Erythropoietin Alpha-helix (hA; n=4). hA 100/Ul: 30 pM; hA 50 U/l: 15 pM; hEPO: 30 pM=100 U/l; P*<0.05; ANOVA1 versus control FIG. 14: Neuroprotection mediated by several human EPO-isoforms (n=6) P*<0.05; ANOVA1 versus control FIG. 15: Neuroprotection mediated by Erythropoietin Alpha-helix deletion variants (n=6) P*<0.05; ANOVA1 versus control A: column diagram showing the average values of normalized LDH release. B: Box plot showing the medians and percentiles (25%, 75%) values of normalized LDH release FIG. 16. Effects of human EPO variants and full length human EPO on LPS-induced cytokine production by human macrophages. Purified human monocytes were differentiated into macrophages in the presence of rhu M-CSF (50 ng/ml) for 6 days. Macrophages (1×106/ml) were pre-incubated with hS4, hS3 or hEPO (300 mU/ml each) for 3 h and then stimulated with 10 ng/ml endotoxin (LPS from *E. coli* 0127:138) for 4 h. Cytokine concentration in supernatants was determined by ELISA (Cytometric Beads Array, Becton Dickinson, Heidelberg, Germany). Data are shown as mean±SD, ** Results differed from Control (PBS) group (p<0.01; Mann-Whitney U test; n=3-9 per group).

FIG. 17: Alignment of nucleic acid sequences of EPO deletion variants (SEQ ID NOS 76, 23 and 56-59, respectively, in order of appearance).

FIG. 18: DNA sequences of mutants and deletion variants created recombinantly as well as wild type Helix A (hWT-EPO Helix A). Herein SEQ ID NO 55 is hA (Wild type Helix A), SEQ ID NO 56 is hAmA (deletion mutatant with Martin), SEQ ID NO 57 is hAmE (deletion mutant with glutamic acid), SEQ ID NO 58 is hA-10 (deletion mutant Helix A minus 10 aa) and SEQ ID NO 59 is hA-20 (deletion mutant Helix A minus 20 aa).

FIG. 19: A preferred embodiment wherein the leader transport sequences are deleted is depicted. A shows the hA DNA sequence without leader as SEQ ID NO 60. This is the mature exported protein. It also shows the leader-sequence (SEQ ID NO 63). 13 shows hA amino acid without leader as SEQ ID NO 61 and the amino acid sequence of the leader-sequence as SEQ ID NO 62.

EXAMPLES

Synthesis of Murine EPO cDNA

RNA was isolated from kidneys of wild type C57BL/6 or SV129S6 mice or from two different mouse brains (1 hour after stroke) by trizol extraction. The RNA was precipitated with chloroform and isopropanol and finally dissolved in DEPC-H$_2$O. DNA was digested to the RQ1 RNase-free DNase protocol from Promega. The reaction was stopped by addition of 2000 phenol/chloroform/isopropyl alcohol (25/24/1) to the reaction mix and centrifugation for 10 min at 10000 rpm and 10° C. The supernatant was mixed with 200 µl chloroform/isopropyl alcohol (24/1) and centrifuged for 10 min at 10000 rpm and 10° C. 20 µl 8 M lithium chloride and 550 µl absolute ethanol were added to the supernatant. This mix was then incubated for 1 h at −70° C. and subsequently precipitated for 30 min by centrifugation at 11000 rpm and 0° C. The resulting pellet was washed with 600 µl 75% ethanol, centrifuged at 8000 rpm (4° C., 10 min) and dried at room temperature. The RNA was dissolved in 20 µl DEPC-H2O.

Moloney murine leukemia virus reverse transcriptase (MuLV, RNase II minus, purchased from Promega) was employed in first strand cDNA synthesis in a 15 µl reaction volume with DEPC-H$_2$O comprising 3 µg RNA and 3 µl random hexamer primer (10 µM). Reverse transcription was carried out with 6 µl M-MuLV reaction buffer (5×), 21 dNTP (2.5 mM each), 1 µl RNase inhibitor (1 U/µl), 1 µl M-MuLV reverse transcriptase and 5 µl DEPC-H$_2$O in a PCR machine running the following program: 5 min at 21° C.; 1 h at 37° C.; 5 min at 95° C.

The resulting cDNA pool was used to amplify the complete EPO cDNA by a Nested PCR approach. The first step employed primers lying outside of the coding region of the EPO gene (genepo_sense (SEQ ID NO 39) gaa ctt cca agg atg aag act tgc agc and genepo_antisense; (SEQ ID NO 40): gtg gca gca gca tgt cac ctg tc). The second step used primers designed to amplify the gene from start to stop codon, with attached BamHI cleaving sites for the subsequent cloning (epo_sense (SEQ ID NO 41 tat gga tcc atg ggg gtg ccc gaa cgt ccc ac and epo_antisense (SEQ ID NO 42 tat gga tcc tca cct gtc ccc tct cct gca gac). All primers were from MWG-Biotech AG. A nested PCR was performed in a Hybaid PCR machine in two steps, first PCR (3 Min at 95° C.; 35 cycles: 30 sec at 65° C., 1 min at 72° C., 30 sec at 95° C.; 10 min at 72° C.; 4° C. hold) and second PCR (3 min at 95° C.; 5 cycles: 30 sec at 67° C., 1 min at 72° C., 30 sec at 95° C.; 15 cycles: 30 sec at 70° C., 1 min at 72° C., 30 sec at 95° C.; 10 min at 72° C.; 4° C.).

In both PCRs, Pfu Turbo Hotstart DNA Polymerase (Stratagene) was used according to the manufacturer's protocol. The PCR product of the first step was diluted 1:50 for the second PCR. A second cDNA synthesis protocol was performed using the Access RT-PCR System (Invitrogen) with the following parameters: 48° C. 5 min; 94° C. 2 min; 40 cycles: 94° C. 30 sec, 65° C. 1 min, 70° C. 2 min; 70° C. 7 min; 4° C. The second PCR was performed as described above.

The amplified full-length EPO cDNA and the EPO isomers were separated on a 1.2% TAE-agarose gel. A picture of the various PCR products is shown in FIG. 1a. The fragments were than purified using the Wizard SV-Gel Cleanup System (Promega) or the Gel Extraction Kit (Qiagen, Hilden, Germany). As Pfu Polymerase generates blunt end products, the cDNA was subcloned in the pCR-Blunt II-TOPO Vector using chemically competent Top10 One Shot Cells from (both Invitrogen).

Plasmid-DNA was isolated out of single colonies by usage of the Qiagen QIA prep Kit. Inserts were sequenced on an ALFexpress™ DNA Sequencer (Pharmacia Biotech) using the Thermo Sequenasen™ Primer Cycle Sequencing Kit (Amersham Biosciences). The primers M13FWDCY (SEQ II) NO 43: gtc gtg act ggg aaa acc ctg gcg) and M13REVCY (SEQ ID NO 44 agc gga taa caa ttt cac aca gga) were labelled with Cy5. The parameters for sequencing were: t=900 min; T=55° C.; 800V; 55 mA and 30 W. The sequence analysis revealed the existence of a novel variant of EPO lacking exon 4 and three internally deleted variants. The nucleotide sequences are depicted in FIG. 2a and FIG. 2b and the encoded peptide sequences are depicted in FIG. 4. The nucleotide and peptide sequence of the EPO variant mS corresponds to SEQ ID NO 13 and SEQ ID NO 14, respectively. The nucleotide and peptide sequence of the EPO variant mG3 corresponds to SEQ ID NO 15 and SEQ ID NO 16, respectively. The nucleotide and peptide sequence of the EPO variant mG5 corresponds to SEQ ID NO 17 and SEQ ID NO 18, respectively. The nucleotide and peptide sequence of the EPO variant m301 corresponds to SEQ ID NO 19 and SEQ ID NO 20, respectively. The nucleotide and peptide sequence of the EPO variant mK3 corresponds to SEQ ID NO 21 and SEQ ID NO 22, respectively.

Synthesis of Human EPO cDNA

Human adult kidney (male) and fetal brain (male) poly A+ RNA was purchased from Stratagene. cDNA was generated from 250 ng kidney RNA or 200 ng brain RNA according to the Moloney murine leukaemia virus reverse transcriptase (MuLV, RNase H minus) as described above. The resulting cDNA pool was used to amplify the complete EPO cDNA using Pfu Polymerase (Stratagene) with the following primers: Hepo_sense (SEQ ID NO 45): gat ggg ggt gca cga atg tcc tgc and Hepo_antisense (SEQ ID NO 46): cac acc tgg tca tct gtc ccc tgt c.

The PCR was performed in a PCR machine from Invitrogen (3 min at 95° C.; 35 cycles: 30 sec at 67° C., 1 min at 72° C., 30 sec at 95° C.; 10 min at 72° C.). In the case of the fetal brain cDNA a Nested PCR approach was used, performing a second amplifying step on the PCR product of 20 cycles. The amplified PCR products were separated on a 1.2% TAE-agarose gel (FIG. 1b) and purified using the Gel Extraction Kit (Qiagen, Hilden, Germany). The purified cDNA was subcloned in the pCR-Blunt II-TOPO Vector using chemically competent Top10 One Shot Cells (both from Invitrogen). Plasmid-DNA was isolated out of single colonies by usage of the QIA prep Kit (Qiagen, Hilden, Germany). Inserts were sequenced on an ALFexpress™ DNA sequencer (Pharmacia Biotech) using the Thermo Sequenase™ Primer Cycle Sequencing Kit (Amersham Biosciences). The primers M13FWDCY (SEQ ID NO 43) and M13REVCY (SEQ ID NO 44) were labelled with Cy5. The parameters for sequencing were: t=900 min; T=55° C.; 800 V; 55 mA and 30 W. The sequence analysis revealed the existence of two novel variants of human EPO missing exon 3 and the first half of exon 4, respectively, and a number of variants that follows the rule of repeated trimers or hexamers as detected in the mouse. The nucleotide sequences are depicted in FIG. 3a and FIG. 3b and the encoded peptide sequences are depicted in FIG. 4. The nucleotide and peptide sequence of the EPO variant hS3 corresponds to SEQ ID NO 1 and SEQ ID NO 2, respectively. The nucleotide and peptide sequence of the EPO variant h1-4 corresponds to SEQ ID NO 3 and SEQ ID NO 4, respectively. The nucleotide and peptide sequence of the EPO variant h1-5 corresponds to SEQ ID NO 5 and SEQ ID NO 6, respectively. The nucleotide and peptide sequence of the EPO variant hS4 corresponds to SEQ ID NO 7 and SEQ ID NO 8, respectively. The nucleotide and peptide sequence of the EPO variant h1-1 corresponds to SEQ ID NO 9 and SEQ ID NO 10, respectively. The nucleotide and peptide sequence of the EPO variant h2-1 corresponds to SEQ ID NO 11 and SEQ ID NO 12, respectively.

Expression of His-Tagged Proteins in HEK Cells

BamHI and EcoRI restriction sites for cloning were added to both the mouse and the human EPO variants by using overhang sense primers and overhang antisense primers without stop codon (for mouse variants: epo_sense (SEQ ID NO 41) and epoeco_antisense (SEQ ID NO 47): aaa gaa ttc cct gtc ccc tct cct gca gac etc; for human variants; hepobam_se (SEQ ID NO 48): tat gga tcc atg ggg gtg cac gaa tgt cc, hepoeco_as [SEQ ID NO 49]: aga gaa ttc tct gtc ccc tgt cct gca g). The PCR products were cloned into pcDNA-3.1-HIS/V5 A (Invitrogen) using BamHI and EcoRI restriction sites. Plasmids were amplified in XL-1 Blue Competent Cells (recA1 endA1 gyrA96 thi1 hsdR17 supE44 relA1 lac [F' proAB lac$^q$ZΔM15 Tn10 (Tet$^R$)]) (Stratagene). The XL-1 Blue Competent Cells transformation protocol was performed without β-mercaptoethanol and with a prolonged heat pulse of 60 seconds. Plasmid DNA was extracted using the QIAprep Spin Miniprep Kit (Qiagen, Hilden, Germany). For transfection into mammalian cells DNA was extracted using the EndoFree Plasmid Maxi Kit (Qiagen, Hilden, Germany). HEK 293 cells (BD biosciences) were grown for 18 days in Dulbecco's modified Eagle's medium (DMEM; Biochrom, Berlin, 1 g/l glucose, 3.7 g/l NaHCO$_3$; supplemented with 10% fetal calf serum GOLD, 1% penicillin/streptavidine and 1% L-glutamine) in tissue culture flasks (25 cm$^2$) at 37° C. and 5% CO$_2$. Cells were split every 2-3 days after reaching 80-90% confluence. At DIV18 120,000 cells were plated per well in a 12 well plate containing Dulbecco's modified Eagle's medium without antibiotics. Cells were grown for approximately 48 b till 50% confluence. Transfection was performed with Lipofectamine 2000 (Invitrogen) adapting the provided protocol for HEK cells.

Plating medium of HEK-cells was replaced 10 min before transfection by serum-free DMEM without antibiotics. Cells were incubated 5 h at 37° C. with DNA-Lipofectamine complexes. Medium was then changed to fresh serum-containing DMEM without antibiotics. At Dm cells were split and plated in Dulbecco's modified Eagle's with antibiotics.

Expression and Purification of his-Tagged EPO Variants

His-tagged proteins were transiently expressed in HEK-cells. Medium from HEK293 cells was harvested 2-6 days after transfection with pcDNA-3.1-H1S/V5 A—constructs. Cell debris was pelleted at 3500 rpm, 4° C. for 15 min. BD TALON™ Metal Affinity Resin (BD Biosciences) was used for purification of his-tag proteins. All steps (equilibration, washing and elution) were performed at pH 7.1. The provided protocol was modified to a prolonged over-night binding step at 4° C. Eluate was collected in 500 µl-fractions. Fractions were analysed by Western Blots using an anti-rhEPO antibody from Santa-Cruz or a murine EPO ELISA-Kit (R&D). Imidazole was removed from protein-containing fractions using HiTrap™ Desalting columns (5 ml) from Amersham Biosciences according to the manufactures protocol. This included a change of buffer to PBS.

Western Blot

A 16% SDS-Gel was prepared using standard-protocols and run at 110 V. Blotting was done on nitrocellulose-membranes for 45 min at 200 mA. The blot was blocked for at least one hour in blocking buffer containing 5% non-fat dry milk powder in 0.1% Tween-20. Incubation with the first antibody (EPO(H-162) se-7956 rabbit polyclonal IgG, Santa Cruz, 1:500) was performed over-night at 4° C., The secondary antibody (goat anti-rabbit HRP; 1:1000) was added for 2 hours at room-temperature. The blot was revealed by use of Luminol; photos were exposed for 2 minutes. Membranes were stained with Ponceau Red. The EPO specific antibody was capable of detection all EPO variants.

Erythroid Colony Formation Assay

Bone marrow cells were harvested from tibia and femur of male C57BL/6 mice (8-11 weeks) and resuspended in α-medium (supplemented with 10% fetal calf serum GOLD, 1% penicillium/streptavidine and 1% L-glutamine). Cells were seeded in 35 mm$^2$ Petri dishes (225.000 cells/dish) containing 8 parts Metho Cult SF 3236 methyl cellulose (StemCell Technologie Inc), 1 part cells and 2 parts α-medium mixed with HEK-cell preconditioned medium containing the EPO derivates (150 U/l in the case of murine EPO). 150 U/l of rhEPO (Roche) was used as positive control. Plates were incubated at 37° C. in a humidified atmosphere containing 5% $CO_2$ for 48 hours. For evaluation only reddish colonies containing at least 6 hemoglobinised cells were taken into account.

Hematopoietic Potential of the EPO Variants

Metho Cult SF 3236 triggers the formation of colonies (CFU-M, CFU-G or CFU-E) only after addition of the appropriate cytokines. Formation of CFU-E (Colony forming unit-erythroblast) can be observed, after addition of erythropoietin, after 2 days. The small irregular reddish colonies disappear by day 3.

In this assay, the hematopoietic potential of the variants was tested and compared to wild type form of EPO as well as rhEPO. The following conditions were prepared for comparison: medium from HEK cells transfected with pZ/EG as negative control, medium from HEK cells transfected with pZ/EG cells plus 150 U/l rhEPO (Roche) as a positive control, and medium from HEK cells transfected with either pZ/EG-EPO-IRES (150 U/l murine EPO), pZ/EG-Splice-IRES (variant S; mS) or pZ/EG-G3-IRES (variant G3; mG3). At DIV2 only reddish colonies were counted containing at least 6 hemoglobinised cells. The results of three independent experiments are depicted in FIG. 5.

In comparison to murine EPO and rhEPO the murine EPO variants (mS and mG3-variant) lacked haematopoietic potential.

Primary Neuronal Cultures

Rat primary neuronal cultures were obtained from E16 to early E19 embryos of Wistar rats (Bundesinstitut fir gesundheitlichen Verbraucherschutz and Veterinärmedizin, Berlin, Germany). Cre-expressing mouse neurons were obtained from E16 embryos of heterozygous transgenic mice expressing Cre-recombinase under the control of the tubulin α-1 promoter (provided by Dr. U. Schweitzer; Experimental Endocrinology, Charité). Murine and rat cultures were prepared according to a modified protocol from Brewer (1995). *J Neurosci Res.* 42: 674-83. Cerebral cortex was isolated after removal of meninges and rinsed twice in PBS (Biochrom, Berlin, Germany). After 15 min incubation in trypsin/EDTA (0.05/0.02% w/v in PBS) at 37° C., tissues were rinsed twice in N-Med (modified Eagle's medium from Gibco with 10% fetal calf serum, 100 U penicillin plus streptomycin from Biochrom, 2 mM L-glutamine, 100 IE insulin/l, 10 mM HEPES and 44 mM glucose) and dissociated carefully in a small volume of N-Med using a Pasteur pipette. Cells were pelleted at room temperature by 2 min centrifugation at 210 g and resuspended in NBM starter medium (Neurobasal medium from Gibco with 2% B27 supplement from Gibco, 1% Pen/Strep, 0.5 mM L-glutamine and 25 µM glutamate).

Preparation of Culture Plates 24-well plates and 6-well plates were pretreated by overnight incubation at 4° C. with poly-L-lysin from Biochrom (2.5 µg/ml in PBS). Rinsing of the wells with PBS was followed by 1 h incubation at 37° C. with coating medium (modified Eagle's medium with 5% FCS Gold from FAA, 1% Pen/Strep, 10 mM HEPES and 0.03 w/v collagen G from Biochrom), then the wells were carefully rinsed twice with PBS. Volume and type of plating medium was chosen depending on experimental procedure.

Oxygen Glucose Deprivation in Rat Primary Cortical Neurons—a Cell Culture Model of Cerebral Ischemia For OGD the culture medium was washed out by rinsing once with PBS. OGD was induced with 500 µl of a deoxygenated aglycemic solution ($BSS_0$—$O_2$; 143.8 mM $Na^+$, 5.5 mM $K^+$, 1.8 mM $Ca^{2+}$, 0.8 mM $Mg^{2+}$, 125.3 mM Cl, 26.2 mM $HCO_3^-$ and 0.8 mM $SO_4^{2-}$, pH 7.4) in a hypoxic atmosphere generated by a dedicated, humidified gas-tight incubator (Concept 400, Ruskinn Technologies, Bridgend, UK) flushed with a gas mix containing 5% $CO_2$, 85% $N_2$ and 10% $H_2$. OGD-time depended on the density and the age of the culture and varied between 2 h 30 min and 2 h 40 min. In control experiments the wells were treated with 500 µl of the oxygenated glycemic BSS solution ($BSS_0+O_2$; 143.8 mM $Na^+$, 5.5 mM $K^+$, 1.8 mM $Ca^{2+}$, 0.8 mM $Mg^{2+}$, 125.3 mM $Cl^-$, 26.2 mM $HCO_3^-$, 0.8 mM $SO_4^{2-}$, and 20 mM glucose, pH 7.4) and incubated at 37° C. in a normoxic atmosphere containing 5% $CO_2$. Immediately after OGD, treated cells and controls were changed from BSS solution to 500 µl of medium containing 40% conditioned NBM plus 60% fresh NBM. After 24 h, lactate dehydrogenase (LDH) activity was measured in the supernatants as an indicator of cell death.

For LDH measurement 25111 of medium was mixed with 100 µl fresh β-NADH solution (0.15 mg/ml in 1×LDH-buffer; Sigma, reduced form) in a 96 wells plate (Greiner). 25 µl of 22.7 mM pyruvate (Sigma) was added immediately before placing the plate into the Reader (Thermo Labsystems; $MRX^{TC}$ Revelation). Parameters were chosen as follows: filter: 340 nm, shake time: 5 see, interval: 30 see, counts: 10. LDH-concentration was calculated proportionally to the LDH-standard (Greiner, system calibrator).

Induction of Neuroprotection by Conditioned Medium from Transfected HEK293 Cells Expressing EPO Variants In the following experiments rhEPO (recombinant human EPO from Sigma Aldrich, Deisenhofen, Germany) was used as a positive control. Neuroprotection assays are schematically depicted in FIG. 6. Neurons were plated in 24-well plates at a density of 300,000 cells in a final volume of 600 µl NBM starter medium. After 4 days, 200 µl of the medium was replaced by 250 µl fresh NBM (same as NBM starter without glutamate).

For pretreatment with rhEPO, wild type mEPO, wild type hEPO or EPO variants the medium was removed to an end volume of 200 µl and filled up with 200 µl fresh NBM+B27 containing equimolar amounts (corresponding to 200 U/l rbEpo) of EPO or EPO variants, respectively. Equivalent concentrations of the various EPO variants (as well as rhEPO and hEPO) in the conditioned medium from HEK293 cells were estimated by Western blot and EPO-Elisa. Thereafter neurons were grown for 48 h under normoxic, humified conditions at 37° C. before oxygen glucose deprivation (OGD) was performed (OGD interval as indicated). Cell death was assessed 24 h after OGD by measurement of LDH release. Reduction in LDH release, compared to mock-treated neurons (medium from HEK293 cells transfected with the backbone plasmid;=ko; 100%), is a quantitative measure of neuroprotection. In all experiments we observed a more robust neuroprotective effect provided by the EPO variants, if compared to wt EPO (see FIG. 7 Panel A and B for murine EPO and variants thereof and FIG. 8 Panel A and B for human EPO and variants thereof).

The neuroprotection induced by the murine EPO variants is more robust than that induced by EPO (rhEPO as well as wild type mouse EPO). For example, neuroprotection mediated by EPO can only be observed in a clearly defined window of OGD length (corresponding to a clearly defined damage level). At low concentration the neuroprotection by hS3 and hS4 was equal or better than the neuroprotection of wt hEPO. Overall, neuroprotection induced by the variants is stronger than that induced by rhEPO. In addition, variants have an higher neuroprotective potential than both wild type forms mEPO and hEPO, which were produced by the same procedure as the EPO variants.

H9c2-Model of Ischemia

The rat BDIX heart myoblast cell line (obtained from European Collection of Cell Cultures) was cultured in DMEM (Biochrom) containing 4.5 g/l glucose supplemented with 2 mM L-glutamine, 10% inactivated fetal calf serum and 1% penicillin-streptavidin. Subconfluent cultures (70%) were subcultured 1:4. Cells were plated in 400 µl medium containing 120 pM hEPO or hS3 respectively in a density of 15,000 cells per well in 24-well plates and cultured for 48 hours. Hypoxia was achieved by culturing the cells in 400 µl serum-deficient DMEM containing 4.5 g/l glucose supplemented with 2 mM L-glutamine and 1% penicillin-streptavidin and leaving them for 24 h in an anaerobic workstation (Concept 400, Ruskinn Technologies, Bridgend, UK) saturated with a gas mix containing 5% $CO_2$, 85% $N_2$ and 10% $H_2$ at 37° C. Control cells were left in serum-deficient DMEM in a normoxic incubator. At the end of the experiment medium was replaced to 400 µl fresh serum-deficient DMEM and LDH was measured according to standard protocols 24 h later.

Immunoprecipitation

Male 129S6 mice or male C57Bl6 mice (8-10 weeks, Bundesinstituts für Risikobewertung, Berlin) having free access to food and water were used for the experiments. $CoCl_2$ was injected subcutanely in a dose of 60 mg/kg and animals were killed 18 hours later. Protein expression was measured in serum, kidney and brain protein extracts by a commercial available ELISA (R&D, mEPO).

Antibodies for immunoprecipitation were purchased from R&D (anti-mEPO antibody, goat, biotin-labelled) and Santa-Cruz (anti-rhEPO, rabbit). Immunoprecipitation was performed according to standard protocols and evaluated by western blot.

Blocking of the western blot detection antibody was achieved by two hours incubation with 10 µg DarbpoietinA at room temperature prior to blot incubation.

Generation of Alpha-Helix-Mutants (FIG. 10)

Human alpha-helix-mutants were all generated by PCR based approaches using standard protocols.

Mutant A (hAmA) and mutant E (hAmE) are variants of the alpha-helix with amino acid exchange at position 41 (arginine). cDNA sequence was changed from AGG to GCG for mutant A (alanine) or to GAG for mutant E (glutamate). −20aa and −10aa are deletion variants of the alpha-helix missing 20 amino acids or 10 amino acids respectively at the c-terminus. All mutants were generated without V5 and His-tag and expressed in HEK 293 cells. Neuroprotection experiments were performed as described previously using medium of transfected HEK cells expressing the different variants.

hEPO and hS3 Mediated Cytoprotection in a Model of Ischemia in H9c2 Cells (FIG. 11)

The cytoprotective potential of the EPO variants was shown exemplarily for purified hEPO and hS3 in a model of ischemia consisting of serum deprivation and hypoxia in H9c2 cardiac myoblasts (FIG. 1). LDH release was assessed as a marker of apoptotic cell death. We found significant cytoprotective capacities for both variants (approximately 20% and 25% for hEPO and hS3).

Immunoprecipitation Reveals EPO Splicing Isoform in Kidney Protein Extracts of CoCl2-Treated Mice (FIG. 12)

To strengthen our finding of EPO splicing isoforms in human and murine tissues by a PCR-based approach we performed immunoprecipitations on murine serum, brain and kidney protein extracts of CoCl2 treated mice using antibodies tested to recognize both isoforms. Subcutane injection of $CoCl_2$ is known to increase erythropoietin levels in several mouse tissues, namely blood, brain, liver and kidney.

We were able to precipitate erythropoietin (approximately 40 kDa) from serum, brain and kidney protein extracts of CoCl2 treated mice (FIG. 2); precipitation of erythropoietin from a kidney protein extract of an untreated mouse failed due to the low expression level. Furthermore we were able to prove the existence of a second smaller protein (approximately 30 kDa) in the kidney protein extract of CoCl2 treated mice. This protein is specifically recognized by the anti-rhEPO antibody as shown by complete blocking of the antibody-antigene interaction with Darbpoietin A. These findings strongly support the existence of a murine erythropoietin splicing isoform. These results were reproduced in a second mouse strain, namely C57Bl6.

Neuroprotection Mediated by Different Isoforms of the Erythropoietin Alpha-Helix (FIG. 13)

Analysing the neuroprotective potentials of the so far identified erythropoietin variants we suggested the alpha helix to be the functionally important domain for the neuroprotective character of erythropoietin. In order to test this hypothesis we expressed a shortened form of human erythropoietin, namely the alpha-helix domain, in HEK 293 cells and tested this peptide in our OGD-model. We found an equivalent protective potential with 30 pM and 15 pM of this peptide to 30 pM of hEPO as shown in FIG. 13.

In order to identify the functional important residues in the alpha helix domains of human erythropoietin we generated different erythropoietin mutants containing either amino acid exchanges (hAmA and hAmE) or complete domain deletions (hA-10 and hA-20).

Figure 14:
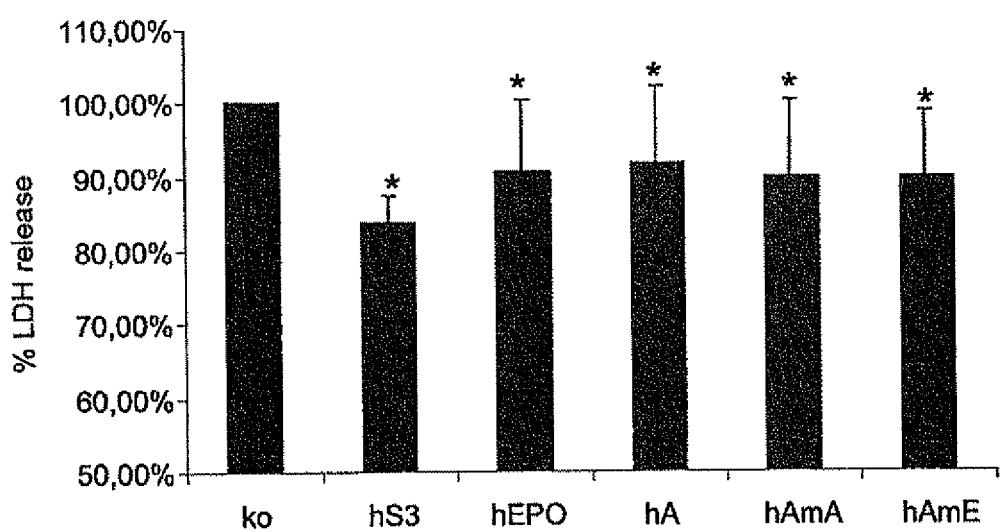

Neither the neutral nor the acidic amino acid exchange at position 41 was able to destroy the neuroprotective potential of the alpha-helix in our OGD model (FIG. 14).

Neuroprotection mediated by several human EPO-isoforms (n=6) $P^* < 0.05$; ANOVA1 versus control (FIG. 14)

Deletion variants missing 10 or 20 amino acids at the c-terminus of the alpha-helix were expressed in HEK (293 cells and also tested in the OGD-model. The deletion variant hA-10 had still neuroprotective properties comparable to the hS3 splice isoform. Deletion of 20 amino acids (EA-20) led to a peptide that was not protective anymore (FIG. 15).

Figure 16:
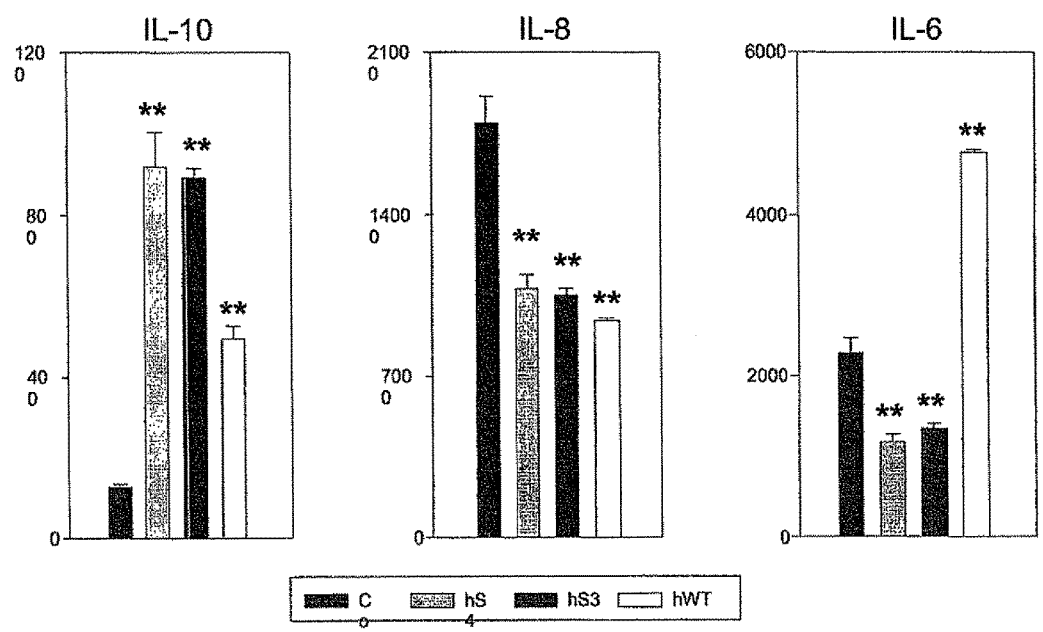

Immunomodulation by Human Erythropoietin Variants (FIG. 16)

The human EPO variants hS3 and hS4 exhibit strong immunomodulatory effects. In human macrophages stimulated with the endotoxin lipopolysaccharide (LPS) hS3 and hS4 induce the anti-inflammatory cytokine IL-10 and reduce the expression of the pro-inflammatory cytokines IL-6 and IL-8. Compared to EPO (hWT) anti-inflammatory effects of hS3 and hS4 are much more pronounced. These anti-inflammatory properties of EPO variants are useful in treatment of inflammatory (e.g. Multiple Sclerosis, viral and bacterial infections, sepsis) and degenerative diseases (e.g. stroke, myocardial infarctions).

The invention claimed is:

1. An isolated polypeptide having the amino acid sequence encoded by a polynucleotide, wherein the polynucleotide is selected from the group consisting of:
   (a) polynucleotide encoding at least the mature form of the polypeptide termed hs3 having the deduced amino acid sequence as shown in SEQ ID NO: 2;
   (b) polynucleotide having the coding sequence, as shown in SEQ ID NO: 1 encoding at least the mature form of the polypeptide;
   (c) polynucleotide encoding a humanized version of the polypeptides mS, mG3, mG5, m301 or mK3 having the deduced amino acid sequence as shown in SEQ ID NOs 14, 16, 18, 20, or 22, wherein the polypeptide has neuroprotective activity but essentially no hematopoietic activity;
   (d) polynucleotide encoding a polypeptide comprising a fusion of an amino acid sequence selected from the group of amino acid sequences as shown in SEQ ID NO 24, 26, 28, and 30, at the N-terminus of an amino acid sequence selected from the group of amino acid sequences as shown in SEQ ID NO 32, 34, 36, and 38, wherein the polypeptide has neuroprotective activity but essentially no hematopoietic activity; and
   (e) polynucleotide comprising a fusion of polynucleotide sequence selected from the group of polynucleotide sequences as shown in SEQ ID NO 23, 25, 27, and 29, 5' of a polynucleotide sequence selected from the group of polynucleotide sequences as shown in SEQ ID NO 31, 33, 35, and 37, wherein the polypeptide encoded by the polynucleotide has neuroprotective activity but essentially no hematopoietic activity.

2. A composition comprising a polypeptide of claim 1.

* * * * *

SEQUENCE LISTING

<160> NUMBER OF SEQ ID NOS: 81

<210> SEQ ID NO 1
<211> LENGTH: 495
<212> TYPE: DNA
<213> ORGANISM: Homo sapiens

<400> SEQUENCE: 1

| | | |
|---|---|---|
| atggggtgc acgaatgtcc tgcctggctg tggcttctcc tgtccctgct gtcgctccct | 60 |
| ctgggcctcc cagtcctggg cgccccacca cgcctcatct gtgacagccg agtcctggag | 120 |
| aggtacctct tggaggccaa ggaggccgag aatatcacgg tcgggcagca ggccgtagaa | 180 |
| gtctggcagg gcctggccct gctgtcggaa gctgtcctgc ggggccaggc cctgttggtc | 240 |
| aactcttccc agccgtggga gccctgcag ctgcatgtgg ataaagccgt cagtggcctt | 300 |
| cgcagcctca ccactctgct tcgggctctg cgagcccaga aggaagccat ctcccctcca | 360 |
| gatgcggcct cagctgctcc actccgaaca atcactgctg acactttccg caaactcttc | 420 |
| cgagtctact ccaatttcct ccggggaaag ctgaagctgt acacagggga ggcctgcagg | 480 |
| acagggaca gatga | 495 |

<210> SEQ ID NO 2
<211> LENGTH: 164
<212> TYPE: PRT
<213> ORGANISM: Homo sapiens

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Val Gly Gln Gln Ala Val Glu Val Trp Gln Gly
    50                  55                  60

Leu Ala Leu Leu Ser Glu Ala Val Leu Arg Gly Gln Ala Leu Leu Val
65                  70                  75                  80

Asn Ser Ser Gln Pro Trp Glu Pro Leu Gln Leu His Val Asp Lys Ala
                85                  90                  95

Val Ser Gly Leu Arg Ser Leu Thr Thr Leu Leu Arg Ala Leu Gly Ala
            100                 105                 110

Gln Lys Glu Ala Ile Ser Pro Pro Asp Ala Ala Ser Ala Ala Pro Leu
        115                 120                 125

Arg Thr Ile Thr Ala Asp Thr Phe Arg Lys Leu Phe Arg Val Tyr Ser
    130                 135                 140

Asn Phe Leu Arg Gly Lys Leu Lys Leu Tyr Thr Gly Glu Ala Cys Arg
145                 150                 155                 160

Thr Gly Asp Arg

<210> SEQ ID NO 3
<211> LENGTH: 525
<212> TYPE: DNA
<213> ORGANISM: Homo sapiens

<400> SEQUENCE: 3

| | | |
|---|---|---|
| atggggtgc acgaatgtcc tgcctggctg tggcttctcc tgtccctgct gtcgctccct | 60 |
| ctgggcctcc cagtcctggg cgccccacca cgcctcatct gtgacagccg agtcctggag | 120 |

```
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cctgttggtc aactcttccc agccgtggga gcccctgcag    300
ctgcatgtgg ataaagccgt cagtggcctt cgcagcctca ccactctgct tcgggctctg    360
ggagcccaga aggaagccat ctcccctcca gatgcggcct cagctgctcc actccgaaca    420
atcactgctg acactttccg caaactcttc cgagtctact ccaatttcct ccggggaaag    480
ctgaagctgt acacagggga ggcctgcagg acagggaca gatga                     525
```

```
<210> SEQ ID NO 4
<211> LENGTH: 174
<212> TYPE: PRT
<213> ORGANISM: Homo sapiens

<400> SEQUENCE: 4
```

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Leu Leu Val Asn Ser Ser Gln Pro Trp
                85                  90                  95

Glu Pro Leu Gln Leu His Val Asp Lys Ala Val Ser Gly Leu Arg Ser
            100                 105                 110

Leu Thr Thr Leu Leu Arg Ala Leu Gly Ala Gln Lys Glu Ala Ile Ser
        115                 120                 125

Pro Pro Asp Ala Ala Ser Ala Ala Pro Leu Arg Thr Ile Thr Ala Asp
    130                 135                 140

Thr Phe Arg Lys Leu Phe Arg Val Tyr Ser Asn Phe Leu Arg Gly Lys
145                 150                 155                 160

Leu Lys Leu Tyr Thr Gly Glu Ala Cys Arg Thr Gly Asp Arg
                165                 170

```
<210> SEQ ID NO 5
<211> LENGTH: 495
<212> TYPE: DNA
<213> ORGANISM: Homo sapiens

<400> SEQUENCE: 5
atgggggtgc acgaatgtcc tgcctggctg tggcttctcc tgtccctgct gtcgctccct     60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctgttggtc    240 aactcttccc agccgtggga gcccctgcag ctgcatgtgg ataaagccgt cagtggcctt    300
cgcagcctca ccactctgct tcgggctctg ggagcccaga aggaagccat ctcccctcca    360
gatgcggcct cagctgctcc actccgaaca atcactgctg acactttccg caaactcttc    420
```

```
cgagtctact ccaatttcct ccggggaaag ctgaagctgt acacagggga ggcctgcagg    480 acagggggaca gatga                                                    495
```

<210> SEQ ID NO 6
<211> LENGTH: 164
<212> TYPE: PRT
<213> ORGANISM: Homo sapiens

<400> SEQUENCE: 6

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Leu Leu Val
65                  70                  75                  80

Asn Ser Ser Gln Pro Trp Glu Pro Leu Gln Leu His Val Asp Lys Ala
                85                  90                  95

Val Ser Gly Leu Arg Ser Leu Thr Thr Leu Leu Arg Ala Leu Gly Ala
            100                 105                 110

Gln Lys Glu Ala Ile Ser Pro Pro Asp Ala Ala Ser Ala Ala Pro Leu
        115                 120                 125

Arg Thr Ile Thr Ala Asp Thr Phe Arg Lys Leu Phe Arg Val Tyr Ser
    130                 135                 140

Asn Phe Leu Arg Gly Lys Leu Lys Leu Tyr Thr Gly Glu Ala Cys Arg
145                 150                 155                 160

Thr Gly Asp Arg
```

<210> SEQ ID NO 7
<211> LENGTH: 489
<212> TYPE: DNA
<213> ORGANISM: Homo sapiens

<400> SEQUENCE: 7

```
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggagccgt gggagcccct gcagctgcat gtggataaag ccgtcagtgg ccttcgcagc   300
ctcaccactc tgcttcgggc tctgggagcc cagaaggaag ccatctcccc tccagatgcg   360
gcctcagctg ctccactccg aacaatcact gctgacactt tccgcaaact cttccgagtc   420
tactccaatt tcctccgggg aaagctgaag ctgtacacag ggaggcctg caggacaggg   480 gacagatga                                                           489
```

<210> SEQ ID NO 8
<211> LENGTH: 162
<212> TYPE: PRT
<213> ORGANISM: Homo sapiens

<400> SEQUENCE: 8

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Pro Trp Glu Pro Leu Gln Leu His Val Asp Lys Ala Val Ser
                85                  90                  95

Gly Leu Arg Ser Leu Thr Thr Leu Leu Arg Ala Leu Gly Ala Gln Lys
            100                 105                 110

Glu Ala Ile Ser Pro Pro Asp Ala Ala Ser Ala Ala Pro Leu Arg Thr
            115                 120                 125

Ile Thr Ala Asp Thr Phe Arg Lys Leu Phe Arg Val Tyr Ser Asn Phe
130                 135                 140

Leu Arg Gly Lys Leu Lys Leu Tyr Thr Gly Glu Ala Cys Arg Thr Gly
145                 150                 155                 160

Asp Arg
```

<210> SEQ ID NO 9
<211> LENGTH: 475
<212> TYPE: DNA
<213> ORGANISM: Homo sapiens

<400> SEQUENCE: 9

```
atggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc    180
agcttgaatg agaatatcac tgtcccaggc cctgttggtc aactcttccc agccgtggga   240
gccctgcag ctgcatgtgg ataaagccgt cagtggcctt cgcagcctca ccactctgct   300
tcgggctctg ggagcccaga aggaagccat ctcccctcca gatgcggcct cagctgctcc   360
actccgaaca atcactgctg acactttccg caaactcttc cgagtctact ccaatttcct   420
ccggggaaag ctgaagctgt acacagggga ggcctgcagg acagggacag atga        475
```

<210> SEQ ID NO 10
<211> LENGTH: 87
<212> TYPE: PRT
<213> ORGANISM: Homo sapiens

<400> SEQUENCE: 10

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                  60
```

Asn Ile Thr Val Pro Gly Pro Val Gly Gln Leu Phe Pro Ala Val Gly
65                  70                  75                  80

Ala Pro Ala Ala Ala Cys Gly
                85

<210> SEQ ID NO 11
<211> LENGTH: 301
<212> TYPE: DNA
<213> ORGANISM: Homo sapiens

<400> SEQUENCE: 11

```
atggggtgc acgaatgtcc tgcctggctg tggcttctcc tgtccctgct gtcgctccct      60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaacaatca ctgctgacac tttccgcaaa ctcttccgag tctactccaa    240
tttcctccgg ggaaagctga agctgtacac aggggaggcc tgcaggacag ggacagatg    300
a                                                                    301
```

<210> SEQ ID NO 12
<211> LENGTH: 68
<212> TYPE: PRT
<213> ORGANISM: Homo sapiens

<400> SEQUENCE: 12

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Asn His Cys
65

<210> SEQ ID NO 13
<211> LENGTH: 399
<212> TYPE: DNA
<213> ORGANISM: Mus musculus

<400> SEQUENCE: 13

```
atggggtgc ccgaacgtcc caccctgctg cttttactct ccttgctact gattcctctg      60
ggcctcccag tcctctgtgc tcccccacgc ctcatctgcg acagtcgagt tctggagagg    120
tacatcttag aggccaagga ggcagaaaat gtcacgatgg ttgtgcagag aggtcccaga    180
ctgagtgaaa atattacagt cccagatacc aaagtcaact ctatgcttg gaaaagaatg     240
gagaaggaat tgatgtcgcc tccagatacc accccacctg ctccactccg aacactcaca    300
gtggatactt tctgcaagct cttccgggtc tacgccaact tcctccgggg gaaactgaag    360
ctgtacacgg gagaggtctg caggagaggg acaggtga                            399
```

<210> SEQ ID NO 14
<211> LENGTH: 132
<212> TYPE: PRT
<213> ORGANISM: Mus musculus

<400> SEQUENCE: 14

```
Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Lys Glu Leu Met Ser Pro Pro Asp Thr Thr Pro Pro Ala Pro Leu
                85                  90                  95

Arg Thr Leu Thr Val Asp Thr Phe Cys Lys Leu Phe Arg Val Tyr Ala
            100                 105                 110

Asn Phe Leu Arg Gly Lys Leu Lys Leu Tyr Thr Gly Glu Val Cys Arg
        115                 120                 125

Arg Gly Asp Arg
    130
```

<210> SEQ ID NO 15
<211> LENGTH: 387
<212> TYPE: DNA
<213> ORGANISM: Mus musculus

<400> SEQUENCE: 15

```
atgggggtgc cgaacgtcc caccctgctg cttttactct ccttgctact gattcctctg      60
ggcctcccag tcctctgtgc tcccccacgc tcatctgcg acagtcgagt tctggagagg     120
tacatcttag aggccaagga ggcagaaaat gtcacgatgg gttgtgcaga aggtcccaga    180
ctgagtgaaa atattacagt cccagatacc aaagtcaact tctatgcttg gaaaagaatg    240
gaggtggaag aacaggccat agaagtttgg caaggcctgt ccctgctctc agaagccatc    300
ctgcaggccc aggccctgct agccaacttc ctccggggga aactgaagct gtacacggga    360
gaggtctgca ggagagggga caggtga                                        387
```

<210> SEQ ID NO 16
<211> LENGTH: 128
<212> TYPE: PRT
<213> ORGANISM: Mus musculus

<400> SEQUENCE: 16

```
Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95
```

Ser Glu Ala Ile Leu Gln Ala Gln Ala Leu Leu Ala Asn Phe Leu Arg
            100                 105                 110

Gly Lys Leu Lys Leu Tyr Thr Gly Glu Val Cys Arg Arg Gly Asp Arg
        115                 120                 125

<210> SEQ ID NO 17
<211> LENGTH: 513
<212> TYPE: DNA
<213> ORGANISM: Mus musculus

<400> SEQUENCE: 17
atgggggtgc ccgaacgtcc caccctgctg cttttactct ccttgctact gattcctctg      60
ggcctcccag tcctctgtgc tcccccacgc ctcatctgcg acagtcgagt tctggagagg     120
tacatcttag aggccaagga ggcagaaaat gtcacgatgg gttgtgcaga aggtcccaga     180
ctgagtgaaa atattacagt cccagatacc aaagtcaact tctatgcttg gaaaagaatg     240
gaggtggaag aacaggccat agaagtttgg caaggcctgt ccctgctctc agaagccatc     300
ctgcaggccc aggccctgct agccaattcc tcccagccac cagagaccct tcagcttcat     360
atagacaaag ccatcagtgg tctacgtagc ctcacttcac tgcttcgggt actgggagct     420
cagaaggaat tgatgtcgcc tccagatacc accccacctg ctccactccg aacactcaca     480
gtggatactt tctgcaggag agggacagg tga                                    513

<210> SEQ ID NO 18
<211> LENGTH: 170
<212> TYPE: PRT
<213> ORGANISM: Mus musculus

<400> SEQUENCE: 18

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn Ser Ser Gln
            100                 105                 110

Pro Pro Glu Thr Leu Gln Leu His Ile Asp Lys Ala Ile Ser Gly Leu
        115                 120                 125

Arg Ser Leu Thr Ser Leu Leu Arg Val Leu Gly Ala Gln Lys Glu Leu
    130                 135                 140

Met Ser Pro Pro Asp Thr Thr Pro Pro Ala Pro Leu Arg Thr Leu Thr
145                 150                 155                 160

Val Asp Thr Phe Cys Arg Arg Gly Asp Arg
                165                 170

<210> SEQ ID NO 19
<211> LENGTH: 279
<212> TYPE: DNA
<213> ORGANISM: Mus musculus

<400> SEQUENCE: 19

```
atggggtgc ccgaacgtcc caccctgctg cttttactct ccttgctact gattcctctg    60
ggcctcccag tcctctgtgc tccccacgc ctcatctgcg acagtcgagt tctggagagg   120
tacatcttag aggccaagga ggcagaaaat gtcacgatgg gttgtgcaga aggtcccaga   180
ctgagtgaaa atattacagt cccagatacc aaagtcaact tcctccgggg gaaactgaag   240
ctgtacacgg gagaggtctg caggagaggg gacaggtga                         279
```

<210> SEQ ID NO 20
<211> LENGTH: 92
<212> TYPE: PRT
<213> ORGANISM: Mus musculus

<400> SEQUENCE: 20

```
Met Gly Val Pro Glu Arg Pro Thr Leu Leu Leu Leu Ser Leu Leu
1               5                   10                  15
Leu Ile Pro Leu Gly Leu Pro Val Leu Cys Ala Pro Arg Leu Ile
                20                  25                  30
Cys Asp Ser Arg Val Leu Glu Arg Tyr Ile Leu Glu Ala Lys Glu Ala
            35                  40                  45
Glu Asn Val Thr Met Gly Cys Ala Glu Gly Pro Arg Leu Ser Glu Asn
        50                  55                  60
Ile Thr Val Pro Asp Thr Lys Val Asn Phe Leu Arg Gly Lys Leu Lys
65                  70                  75                  80
Leu Tyr Thr Gly Glu Val Cys Arg Arg Gly Asp Arg
                85                  90
```

<210> SEQ ID NO 21
<211> LENGTH: 591
<212> TYPE: DNA
<213> ORGANISM: Mus musculus

<400> SEQUENCE: 21

```
atggggtgc ccgaacgtcc caccctgctg cttttactct ccttgctact gattcctctg    60
ggcctcccag tcctctgtgc tccccacgc ctcatctgcg acagtcgagt tctggagagg   120
tacatcttag aggccaagga ggcagaaaat gtcacgatgg gttgtgcaga aggtcccaga   180
ctgagtgaaa atattacagt cccagatacc aaagtcaact tctatgcttg aaaagaatg    240
gaggtggaag aacaggccat agaagtttgg caaggcctgt ccctgctctc agaagctgta   300
cacgggagag gtctgcagga gggggacag gtgacatgct gctgccaccg tggtggaccg   360
acgaacttgc tccccgtcac tgtgtcatgc aaccctcca ccactcccaa ccctcatcaa    420
acgggtcatt accttcttac cagtctgtcc catggacact ccagcaccag cagtgacatc   480
ctcggggcca agaaacttc ccagagctcc attctgaaat ctaaagatgt cgctggacaa    540
gcccgaggcc cagagaaga agagcctcag aatcagctcg gatttgttta g             591
```

<210> SEQ ID NO 22
<211> LENGTH: 196
<212> TYPE: PRT
<213> ORGANISM: Mus musculus

<400> SEQUENCE: 22

```
Met Gly Val Pro Glu Arg Pro Thr Leu Leu Leu Leu Ser Leu Leu
1               5                   10                  15
Leu Ile Pro Leu Gly Leu Pro Val Leu Cys Ala Pro Arg Leu Ile
                20                  25                  30
```

```
Cys Asp Ser Arg Val Leu Glu Arg Tyr Ile Leu Glu Ala Lys Glu Ala
            35                  40                  45

Glu Asn Val Thr Met Gly Cys Ala Glu Gly Pro Arg Leu Ser Glu Asn
 50                  55                  60

Ile Thr Val Pro Asp Thr Lys Val Asn Phe Tyr Ala Trp Lys Arg Met
 65                  70                  75                  80

Glu Val Glu Glu Gln Ala Ile Glu Val Trp Gln Gly Leu Ser Leu Leu
                85                  90                  95

Ser Glu Ala Val His Gly Arg Gly Leu Gln Glu Arg Gly Gln Val Thr
                100                 105                 110

Cys Cys Cys His Arg Gly Gly Pro Thr Asn Leu Leu Pro Val Thr Val
                115                 120                 125

Ser Cys Gln Pro Ser Thr Thr Pro Asn Pro His Gln Thr Gly His Tyr
            130                 135                 140

Leu Leu Thr Ser Leu Ser His Gly His Ser Ser Thr Ser Ser Asp Ile
145                 150                 155                 160

Leu Gly Ala Arg Arg Thr Ser Gln Ser Ser Ile Leu Lys Ser Lys Asp
                165                 170                 175

Val Ala Gly Gln Ala Arg Gly Pro Arg Glu Glu Pro Gln Asn Gln
            180                 185                 190

Leu Gly Phe Val
        195

<210> SEQ ID NO 23
<211> LENGTH: 159
<212> TYPE: DNA
<213> ORGANISM: Homo sapiens

<400> SEQUENCE: 23 atggggggtgc acgaatgtcc tgcctggctg tggcttctcc tgtccctgct gtcgctccct        60
ctgggcctcc cagtcctggg cgccccacca cgcctcatct gtgacagccg agtcctggag       120
aggtacctct tggaggccaa ggaggccgag aatatcacg                               159

<210> SEQ ID NO 24
<211> LENGTH: 53
<212> TYPE: PRT
<213> ORGANISM: Homo sapiens

<400> SEQUENCE: 24

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr
    50

<210> SEQ ID NO 25
<211> LENGTH: 225
<212> TYPE: DNA
<213> ORGANISM: Homo sapiens

<400> SEQUENCE: 25 atggggggtgc acgaatgtcc tgcctggctg tggcttctcc tgtccctgct gtcgctccct        60
ctgggcctcc cagtcctggg cgccccacca cgcctcatct gtgacagccg agtcctggag       120
```

```
aggtacctct tggaggccaa ggaggccgag aatatcacga cgggctgtgc tgaacactgc    180
agcttgaatg agaatatcac tgtcccagac accaaagtta atttc                    225
```

<210> SEQ ID NO 26
<211> LENGTH: 82
<212> TYPE: PRT
<213> ORGANISM: Homo sapiens

<400> SEQUENCE: 26

```
Met Gly Val His Glu Cys Pro Ala Trp Leu Trp Leu Leu Ser Leu
1               5                  10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu
```

<210> SEQ ID NO 27
<211> LENGTH: 243
<212> TYPE: DNA
<213> ORGANISM: Mus musculus

<400> SEQUENCE: 27

```
atgggggtgc ccgaacgtcc caccctgctg cttttactct ccttgctact gattcctctg    60
ggcctcccag tcctctgtgc tccccacgc ctcatctgcg acagtcgagt tctggagagg    120
tacatcttag aggccaagga ggcagaaaat gtcacgatgg gttgtgcaga aggtcccaga    180
ctgagtgaaa atattacagt cccagatacc aaagtcaact tctatgcttg gaaaagaatg    240
gag                                                                   243
```

<210> SEQ ID NO 28
<211> LENGTH: 81
<212> TYPE: PRT
<213> ORGANISM: Mus musculus

<400> SEQUENCE: 28

```
Met Gly Val Pro Glu Arg Pro Thr Leu Leu Leu Leu Ser Leu Leu
1               5                  10                  15

Leu Ile Pro Leu Gly Leu Pro Val Leu Cys Ala Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu
```

<210> SEQ ID NO 29
<211> LENGTH: 326
<212> TYPE: DNA
<213> ORGANISM: Mus musculus -continued

<400> SEQUENCE: 29

| atggggtgc | ccgaacgtcc | caccctgctg | cttttactct | ccttgctact | gattcctctg | 60 |
| ggcctcccag | tcctctgtgc | tccccacgc | ctcatctgcg | acagtcgagt | tctggagagg | 120 |
| tacatcttag | aggccaagga | ggcagaaaat | gtcacgatgg | gttgtgcaga | aggtcccaga | 180 |
| ctgagtgaaa | atattacagt | cccagatacc | aaagtcaact | tctatgcttg | gaaaagaatg | 240 |
| gaggtggaag | aacaggccat | agaagtttgg | caaggcctgt | ccctgctctc | agaagccatc | 300 |
| ctgcaggccc | aggccctgct | agccaa | | | | 326 |

<210> SEQ ID NO 30
<211> LENGTH: 109
<212> TYPE: PRT
<213> ORGANISM: Mus musculus

<400> SEQUENCE: 30

Met Gly Val Pro Glu Arg Pro Thr Leu Leu Leu Leu Ser Leu Leu
1               5                   10                  15

Leu Ile Pro Leu Gly Leu Pro Val Leu Cys Ala Pro Arg Leu Ile
                20                  25                  30

Cys Asp Ser Arg Val Leu Glu Arg Tyr Ile Leu Glu Ala Lys Glu Ala
            35                  40                  45

Glu Asn Val Thr Met Gly Cys Ala Glu Gly Pro Arg Leu Ser Glu Asn
        50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
                85                  90                  95

Ser Glu Ala Ile Leu Gln Ala Gln Ala Leu Leu Ala Asn
            100                 105

<210> SEQ ID NO 31
<211> LENGTH: 336
<212> TYPE: DNA
<213> ORGANISM: Homo sapiens

<400> SEQUENCE: 31

| gtcgggcagc | aggccgtaga | agtctggcag | ggcctggccc | tgctgtcgga | agctgtcctg | 60 |
| cggggccagg | ccctgttggt | caactcttcc | cagccgtggg | agcccctgca | gctgcatgtg | 120 |
| gataaagccg | tcagtggcct | tcgcagcctc | accactctgc | ttcgggctct | gggagcccag | 180 |
| aaggaagcca | tctcccctcc | agatgcggcc | tcagctgctc | cactccgaac | aatcactgct | 240 |
| gacactttcc | gcaaactctt | ccgagtctac | tccaatttcc | tccggggaaa | gctgaagctg | 300 |
| tacacagggg | aggcctgcag | gacaggggac | agatga | | | 336 |

<210> SEQ ID NO 32
<211> LENGTH: 111
<212> TYPE: PRT
<213> ORGANISM: Homo sapiens

<400> SEQUENCE: 32

Val Gly Gln Gln Ala Val Glu Val Trp Gln Gly Leu Ala Leu Leu Ser
1               5                   10                  15

Glu Ala Val Leu Arg Gly Gln Ala Leu Leu Val Asn Ser Ser Gln Pro
                20                  25                  30

Trp Glu Pro Leu Gln Leu His Val Asp Lys Ala Val Ser Gly Leu Arg
            35                  40                  45

```
Ser Leu Thr Thr Leu Leu Arg Ala Leu Gly Ala Gln Lys Glu Ala Ile
    50                  55                  60

Ser Pro Pro Asp Ala Ala Ser Ala Ala Pro Leu Arg Thr Ile Thr Ala
 65                  70                  75                  80

Asp Thr Phe Arg Lys Leu Phe Arg Val Tyr Ser Asn Phe Leu Arg Gly
                 85                  90                  95

Lys Leu Lys Leu Tyr Thr Gly Glu Ala Cys Arg Thr Gly Asp Arg
                100                 105                 110
```

<210> SEQ ID NO 33
<211> LENGTH: 234
<212> TYPE: DNA
<213> ORGANISM: Homo sapiens

<400> SEQUENCE: 33

```
cccctgcagc tgcatgtgga taaagccgtc agtggccttc gcagcctcac cactctgctt      60
cgggctctgg gagcccagaa ggaagccatc tcccctccag atgcggcctc agctgctcca     120
ctccgaacaa tcactgctga cactttccgc aaactcttcc gagtctactc caatttcctc     180
cggggaaagc tgaagctgta cacggggag gcctgcagga caggggacag atga            234
```

<210> SEQ ID NO 34
<211> LENGTH: 80
<212> TYPE: PRT
<213> ORGANISM: Homo sapiens

<400> SEQUENCE: 34

```
Pro Trp Glu Pro Leu Gln Leu His Val Asp Lys Ala Val Ser Gly Leu
 1               5                  10                  15

Arg Ser Leu Thr Thr Leu Leu Arg Ala Leu Gly Ala Gln Lys Glu Ala
                20                  25                  30

Ile Ser Pro Pro Asp Ala Ala Ser Ala Ala Pro Leu Arg Thr Ile Thr
             35                  40                  45

Ala Asp Thr Phe Arg Lys Leu Phe Arg Val Tyr Ser Asn Phe Leu Arg
     50                  55                  60

Gly Lys Leu Lys Leu Tyr Thr Gly Glu Ala Cys Arg Thr Gly Asp Arg
 65                  70                  75                  80
```

<210> SEQ ID NO 35
<211> LENGTH: 156
<212> TYPE: DNA
<213> ORGANISM: Mus musculus

<400> SEQUENCE: 35

```
aaggaattga tgtcgcctcc agataccacc ccacctgctc cactccgaac actcacagtg      60
gatactttct gcaagctctt ccgggtctac gccaacttcc tccgggggaa actgaagctg     120
tacacgggag aggtctgcag gagagggac aggtga                                156
```

<210> SEQ ID NO 36
<211> LENGTH: 51
<212> TYPE: PRT
<213> ORGANISM: Mus musculus

<400> SEQUENCE: 36

```
Lys Glu Leu Met Ser Pro Pro Asp Thr Thr Pro Pro Ala Pro Leu Arg
 1               5                  10                  15

Thr Leu Thr Val Asp Thr Phe Cys Lys Leu Phe Arg Val Tyr Ala Asn
                20                  25                  30
```

Phe Leu Arg Gly Lys Leu Lys Leu Tyr Thr Gly Glu Val Cys Arg Arg
            35                  40                  45

Gly Asp Arg
    50

<210> SEQ ID NO 37
<211> LENGTH: 61
<212> TYPE: DNA
<213> ORGANISM: Mus musculus

<400> SEQUENCE: 37
cttcctccgg gggaaactga agctgtacac gggagaggtc tgcaggagag gggacaggtg      60
a                                                                     61

<210> SEQ ID NO 38
<211> LENGTH: 19
<212> TYPE: PRT
<213> ORGANISM: Mus musculus

<400> SEQUENCE: 38

Phe Leu Arg Gly Lys Leu Lys Leu Tyr Thr Gly Glu Val Cys Arg Arg
1               5                   10                  15

Gly Asp Arg

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaacttccaa ggatgaagac ttgcagc                                          27

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtggcagcag catgtcacct gtc                                              23

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tatggatcca tggggtgcc cgaacgtccc ac                                     32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatggatcct cacctgtccc ctctcctgca gac                                33

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtcgtgactg ggaaaaccct ggcg                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agcggataac aatttcacac agga                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45 gatggggtg cacgaatgtc ctgc                                           24

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cacacctggt catctgtccc ctgtc                                         25

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaagaattcc ctgtcccctc tcctgcagac ctc                                33

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tatggatcca tggggtgca cgaatgtcc                                29

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agagaattct ctgtcccctg tcctgcag                                28

<210> SEQ ID NO 50
<211> LENGTH: 53
<212> TYPE: PRT
<213> ORGANISM: Homo sapiens

<400> SEQUENCE: 50

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr
    50

<210> SEQ ID NO 51
<211> LENGTH: 53
<212> TYPE: PRT
<213> ORGANISM: Artificial Sequence
<220> FEATURE:
<223> OTHER INFORMATION: Description of Artificial Sequence: Synthetic
      Homo sapiens point mutation polypeptide

<400> SEQUENCE: 51

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Ala Tyr Leu Leu Glu Ala Lys Glu
        35                  40                  45

Ala Glu Asn Ile Thr
    50

<210> SEQ ID NO 52
<211> LENGTH: 53
<212> TYPE: PRT
<213> ORGANISM: Artificial Sequence
<220> FEATURE:
<223> OTHER INFORMATION: Description of Artificial Sequence: Synthetic
      Homo sapiens point mutation polypeptide

<400> SEQUENCE: 52

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Glu Tyr Leu Leu Glu Ala Lys Glu
        35                  40                  45

Ala Glu Asn Ile Thr
    50

<210> SEQ ID NO 53
<211> LENGTH: 43
<212> TYPE: PRT
<213> ORGANISM: Artificial Sequence
<220> FEATURE:
<223> OTHER INFORMATION: Description of Artificial Sequence: Synthetic
      Homo sapiens ha-10 deletion mutant polypeptide

<400> SEQUENCE: 53

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu
        35                  40

<210> SEQ ID NO 54
<211> LENGTH: 33
<212> TYPE: PRT
<213> ORGANISM: Artificial Sequence
<220> FEATURE:
<223> OTHER INFORMATION: Description of Artificial Sequence: Synthetic
      Homo sapiens hA-20 deletion mutant polypeptide

<400> SEQUENCE: 54

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile

<210> SEQ ID NO 55
<211> LENGTH: 159
<212> TYPE: DNA
<213> ORGANISM: Homo sapiens

<400> SEQUENCE: 55
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
aggtacctct tggaggccaa ggaggccgag aatatcacg                          159

<210> SEQ ID NO 56
<211> LENGTH: 159
<212> TYPE: DNA
<213> ORGANISM: Artificial Sequence
<220> FEATURE:
<223> OTHER INFORMATION: Description of Artificial Sequence: Synthetic
      hAmA (Mutant Alanin hwT-EPO Helix A) polynucleotide

<400> SEQUENCE: 56
atgggggtgc acgaatgtcc tgcctggctg tggcttctcc tgtccctgct gtcgctccct    60
ctgggcctcc cagtcctggg cgccccacca cgcctcatct gtgacagccg agtcctggag   120
gcgtacctct tggaggccaa ggaggccgag aatatcacg                          159

<210> SEQ ID NO 57
<211> LENGTH: 159
<212> TYPE: DNA
<213> ORGANISM: Artificial Sequence
<220> FEATURE:
<223> OTHER INFORMATION: Description of Artificial Sequence: Synthetic
      hAmE (Mutant Glutamic-Acid hwT-EPO Helix A) polynucleotide

<400> SEQUENCE: 57
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
gagtacctct tggaggccaa ggaggccgag aatatcacg                            159

<210> SEQ ID NO 58
<211> LENGTH: 129
<212> TYPE: DNA
<213> ORGANISM: Artificial Sequence
<220> FEATURE:
<223> OTHER INFORMATION: Description of Artificial Sequence: Synthetic
      hA-10 (hwT-EPO Helix A minus 10aa) polynucleotide

<400> SEQUENCE: 58
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
gagtacctc                                                             129

<210> SEQ ID NO 59
<211> LENGTH: 99
<212> TYPE: DNA
<213> ORGANISM: Artificial Sequence
<220> FEATURE:
<223> OTHER INFORMATION: Description of Artificial Sequence: Synthetic
      hA-20 (hwT-EPO Helix A minus 20aa) polynucleotide

<400> SEQUENCE: 59
atgggggtgc acgaatgtcc tgcctggctg tggcttctcc tgtccctgct gtcgctccct      60
ctgggcctcc cagtcctggg cgccccacca cgcctcatc                             99

<210> SEQ ID NO 60
<211> LENGTH: 78
<212> TYPE: DNA
<213> ORGANISM: Homo sapiens

<400> SEQUENCE: 60
gccccaccac gcctcatctg tgacagccga gtcctggaga ggtacctctt ggaggccaag      60
gaggccgaga atatcacg                                                    78

<210> SEQ ID NO 61
<211> LENGTH: 16
<212> TYPE: PRT
<213> ORGANISM: Homo sapiens

<400> SEQUENCE: 61

Ala Pro Pro Arg Leu Ile Cys Asp Ser Arg Val Leu Glu Arg Tyr Leu
1               5                   10                  15

<210> SEQ ID NO 62
<211> LENGTH: 27
<212> TYPE: PRT
<213> ORGANISM: Homo sapiens

<400> SEQUENCE: 62

Met Gly Val His Glu Cys Pro Ala Trp Leu Trp Leu Leu Ser Leu
1               5                   10                  15

Leu Ser Leu Pro Leu Gly Leu Pro Val Leu Gly
            20                  25

<210> SEQ ID NO 63
<211> LENGTH: 81
<212> TYPE: DNA
<213> ORGANISM: Homo sapiens

<400> SEQUENCE: 63
atgggggtgc acgaatgtcc tgcctggctg tggcttctcc tgtccctgct gtcgctccct      60
ctgggcctcc cagtcctggg c                                                81

<210> SEQ ID NO 64
<211> LENGTH: 8
<212> TYPE: PRT
<213> ORGANISM: Homo sapiens

<400> SEQUENCE: 64

Glu Asn Ile Thr Arg Val Gly Gln
1               5

<210> SEQ ID NO 65
<211> LENGTH: 8
<212> TYPE: PRT
<213> ORGANISM: Homo sapiens

<400> SEQUENCE: 65

Val Gly Gln Gln Ala Leu Leu Val
1               5

<210> SEQ ID NO 66
<211> LENGTH: 8
<212> TYPE: PRT
<213> ORGANISM: Homo sapiens

<400> SEQUENCE: 66

Val Asn Phe Tyr Ala Leu Leu Val
1               5

<210> SEQ ID NO 67
<211> LENGTH: 8
<212> TYPE: PRT
<213> ORGANISM: Homo sapiens

<400> SEQUENCE: 67

Lys Arg Met Glu Pro Trp Glu Pro
1               5

<210> SEQ ID NO 68
<211> LENGTH: 8
<212> TYPE: PRT
<213> ORGANISM: Homo sapiens

<400> SEQUENCE: 68

Ile Thr Val Pro Gly Pro Val Gly
1               5

```
<210> SEQ ID NO 69
<211> LENGTH: 7
<212> TYPE: PRT
<213> ORGANISM: Homo sapiens

<400> SEQUENCE: 69

Leu Asn Glu Asn Asn His Cys
1               5

<210> SEQ ID NO 70
<211> LENGTH: 8
<212> TYPE: PRT
<213> ORGANISM: Mus musculus

<400> SEQUENCE: 70

Lys Arg Met Glu Lys Glu Leu Met
1               5

<210> SEQ ID NO 71
<211> LENGTH: 8
<212> TYPE: PRT
<213> ORGANISM: Mus musculus

<400> SEQUENCE: 71

Leu Leu Ala Asn Phe Leu Arg Gly
1               5

<210> SEQ ID NO 72
<211> LENGTH: 8
<212> TYPE: PRT
<213> ORGANISM: Mus musculus

<400> SEQUENCE: 72

Asp Thr Phe Cys Arg Arg Gly Asp
1               5

<210> SEQ ID NO 73
<211> LENGTH: 8
<212> TYPE: PRT
<213> ORGANISM: Mus musculus

<400> SEQUENCE: 73

Lys Val Asn Phe Leu Arg Gly Lys
1               5

<210> SEQ ID NO 74
<211> LENGTH: 8
<212> TYPE: PRT
<213> ORGANISM: Mus musculus

<400> SEQUENCE: 74

Leu Ser Glu Ala Val His Gly Arg
1               5

<210> SEQ ID NO 75
<211> LENGTH: 579
<212> TYPE: DNA
<213> ORGANISM: Mus musculus

<400> SEQUENCE: 75
atgggggtgc ccgaacgtcc caccctgctg cttttactct ccttgctact gattcctctg     60
ggcctcccag tcctctgtgc tcccccacgc ctcatctgcg acagtcgagt tctggagagg    120
tacatcttag aggccaagga ggcagaaaat gtcacgatgg gttgtgcaga aggtcccaga    180
```

```
ctgagtgaaa atattacagt cccagatacc aaagtcaact tctatgcttg gaaaagaatg      240
gaggtggaag aacaggccat agaagtttgg caaggcctgt ccctgctctc agaagccatc      300
ctgcaggccc aggccctgct agccaattcc tcccagccac cagagaccct tcagcttcat      360
atagacaaag ccatcagtgg tctacgtagc ctcacttcac tgcttcgggt actgggagct      420
cagaaggaat tgatgtcgcc tccagatacc accccacctg ctccactccg aacactcaca      480
gtggatactt tctgcaagct cttccgggtc tacgccaact tcctccgggg gaaactgaag      540
ctgtacacgg gagaggtctg caggagaggg gacaggtga                            579
```

<210> SEQ ID NO 76
<211> LENGTH: 582
<212> TYPE: PRT
<213> ORGANISM: Homo sapiens

<400> SEQUENCE: 76

```
Ala Thr Gly Gly Gly Gly Thr Gly Cys Ala Cys Gly Ala Ala Thr
1               5                   10                  15

Gly Thr Cys Cys Thr Gly Cys Cys Thr Gly Gly Cys Thr Gly Thr Gly
            20                  25                  30

Gly Cys Thr Thr Cys Thr Cys Thr Gly Thr Cys Cys Cys Thr Gly
        35                  40                  45

Cys Thr Gly Thr Cys Gly Cys Thr Cys Cys Cys Thr Cys Thr Gly Gly
    50                  55                  60

Gly Cys Cys Thr Cys Cys Cys Ala Gly Thr Cys Cys Thr Gly Gly Gly
65                  70                  75                  80

Cys Gly Cys Cys Cys Cys Ala Cys Cys Ala Gly Cys Gly Cys Thr Cys
                85                  90                  95

Ala Thr Cys Thr Gly Thr Gly Ala Cys Ala Gly Cys Cys Gly Ala Gly
            100                 105                 110

Thr Cys Cys Thr Gly Gly Ala Gly Ala Gly Gly Thr Ala Cys Cys Thr
        115                 120                 125

Cys Thr Thr Gly Gly Ala Gly Gly Cys Cys Ala Ala Gly Gly Ala Gly
    130                 135                 140

Gly Cys Cys Gly Ala Gly Ala Ala Thr Ala Thr Cys Ala Cys Gly Ala
145                 150                 155                 160

Cys Gly Gly Gly Cys Thr Gly Thr Gly Cys Thr Gly Ala Ala Cys Ala
                165                 170                 175

Cys Thr Gly Cys Ala Gly Cys Thr Gly Ala Ala Thr Gly Ala Gly
            180                 185                 190

Ala Ala Thr Ala Thr Cys Ala Cys Thr Gly Thr Cys Cys Ala Gly
        195                 200                 205

Ala Cys Ala Cys Cys Ala Ala Ala Gly Thr Thr Ala Ala Thr Thr Thr
    210                 215                 220

Cys Thr Ala Thr Gly Cys Cys Thr Gly Gly Ala Ala Gly Ala Gly Gly
225                 230                 235                 240

Ala Thr Gly Gly Ala Gly Gly Thr Cys Gly Gly Cys Ala Gly Cys
                245                 250                 255

Ala Gly Gly Cys Cys Gly Thr Ala Gly Ala Ala Gly Thr Cys Thr Gly
            260                 265                 270

Gly Cys Ala Gly Gly Cys Cys Thr Gly Cys Cys Cys Thr Gly
        275                 280                 285

Cys Thr Gly Thr Cys Gly Gly Ala Ala Gly Cys Thr Gly Thr Cys Cys
    290                 295                 300
```

```
Thr Gly Cys Gly Gly Gly Cys Cys Ala Gly Cys Cys Cys Thr
305                 310                 315                 320
Gly Thr Thr Gly Thr Cys Ala Ala Cys Thr Cys Thr Thr Cys Cys
                325                 330                 335
Cys Ala Gly Cys Cys Gly Thr Gly Gly Ala Gly Cys Cys Cys
                340                 345                 350
Thr Gly Cys Ala Gly Cys Thr Gly Cys Ala Thr Gly Thr Gly Ala
                355                 360                 365
Thr Ala Ala Gly Cys Cys Gly Thr Cys Ala Gly Thr Gly Gly Cys
        370                 375                 380
Cys Thr Thr Cys Gly Cys Ala Gly Cys Cys Thr Cys Ala Cys Ala
385                 390                 395                 400
Cys Thr Cys Thr Gly Cys Thr Thr Cys Gly Gly Cys Thr Cys Thr
                405                 410                 415
Gly Gly Gly Ala Gly Cys Cys Ala Gly Ala Ala Gly Gly Ala Ala
                420                 425                 430
Gly Cys Cys Ala Thr Cys Thr Cys Cys Cys Thr Cys Cys Ala Gly
        435                 440                 445
Ala Thr Gly Cys Gly Gly Cys Cys Thr Cys Ala Gly Cys Gly Cys
    450                 455                 460
Thr Cys Cys Ala Cys Thr Cys Cys Gly Ala Ala Cys Ala Ala Thr Cys
465                 470                 475                 480
Ala Cys Thr Gly Cys Thr Gly Ala Cys Ala Cys Thr Thr Cys Cys
                485                 490                 495
Gly Cys Ala Ala Ala Cys Thr Cys Thr Thr Cys Cys Gly Ala Gly Thr
        500                 505                 510
Cys Thr Ala Cys Thr Cys Cys Ala Ala Thr Thr Thr Cys Cys Thr Cys
    515                 520                 525
Cys Gly Gly Gly Ala Ala Ala Gly Cys Thr Gly Ala Ala Gly Cys
        530                 535                 540
Thr Gly Thr Ala Cys Ala Cys Ala Gly Gly Gly Ala Gly Gly Cys
545                 550                 555                 560
Cys Thr Gly Cys Ala Gly Gly Ala Cys Ala Gly Gly Gly Ala Cys
                565                 570                 575
Ala Gly Ala Thr Gly Ala
            580

<210> SEQ ID NO 77
<211> LENGTH: 193
<212> TYPE: PRT
<213> ORGANISM: Homo sapiens

<400> SEQUENCE: 77

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80
```

Met Glu Val Gly Gln Ala Val Glu Val Trp Gln Gly Leu Ala Leu
            85                  90                  95

Leu Ser Glu Ala Val Leu Arg Gly Gln Ala Leu Leu Val Asn Ser Ser
        100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 78
<211> LENGTH: 192
<212> TYPE: PRT
<213> ORGANISM: Mus musculus

<400> SEQUENCE: 78

Met Gly Val Pro Glu Arg Pro Thr Leu Leu Leu Leu Leu Ser Leu Leu
1               5                   10                  15

Leu Ile Pro Leu Gly Leu Pro Val Leu Cys Ala Pro Pro Arg Leu Ile
            20                  25                  30

Cys Asp Ser Arg Val Leu Glu Arg Tyr Ile Leu Glu Ala Lys Glu Ala
        35                  40                  45

Glu Asn Val Thr Met Gly Cys Ala Glu Gly Pro Arg Leu Ser Glu Asn
    50                  55                  60

Ile Thr Val Pro Asp Thr Lys Val Asn Phe Tyr Ala Trp Lys Arg Met
65                  70                  75                  80

Glu Val Glu Glu Gln Ala Ile Glu Val Trp Gln Gly Leu Ser Leu Leu
            85                  90                  95

Ser Glu Ala Ile Leu Gln Ala Gln Ala Leu Leu Ala Asn Ser Ser Gln
        100                 105                 110

Pro Pro Glu Thr Leu Gln Leu His Ile Asp Lys Ala Ile Ser Gly Leu
        115                 120                 125

Arg Ser Leu Thr Ser Leu Leu Arg Val Leu Gly Ala Gln Lys Glu Leu
    130                 135                 140

Met Ser Pro Pro Asp Thr Thr Pro Pro Ala Pro Leu Arg Thr Leu Thr
145                 150                 155                 160

Val Asp Thr Phe Cys Lys Leu Phe Arg Val Tyr Ala Asn Phe Leu Arg
                165                 170                 175

Gly Lys Leu Lys Leu Tyr Thr Gly Glu Val Cys Arg Arg Gly Asp Arg
            180                 185                 190

<210> SEQ ID NO 79
<211> LENGTH: 16
<212> TYPE: PRT
<213> ORGANISM: Homo sapiens

<400> SEQUENCE: 79

Ala Pro Pro Arg Leu Ile Cys Asp Ser Arg Val Leu Glu Arg Tyr Leu
1               5                   10                  15

-continued

```
<210> SEQ ID NO 80
<211> LENGTH: 16
<212> TYPE: PRT
<213> ORGANISM: Mus musculus

<400> SEQUENCE: 80

Ala Pro Pro Arg Leu Ile Cys Asp Ser Arg Val Leu Glu Arg Tyr Ile
1               5                   10                  15

<210> SEQ ID NO 81
<211> LENGTH: 582
<212> TYPE: DNA
<213> ORGANISM: Homo sapiens

<400> SEQUENCE: 81
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata aagccgtcag tggccttcgc agcctcacca ctctgcttcg ggctctgcga     420
gcccagaagg aagccatctc ccctccagat gcggcctcag ctgctccact ccgaacaatc     480
actgctgaca ctttccgcaa actcttccga gtctactcca atttcctccg gggaaagctg     540
aagctgtaca caggggaggc ctgcaggaca ggggacagat ga                        582
```